US012559458B2

(12) United States Patent
Knight et al.

(10) Patent No.: US 12,559,458 B2
(45) Date of Patent: Feb. 24, 2026

(54) CO-CRYSTALS OR SALTS OF PSILOCIN AND METHODS OF TREATMENT THEREWITH

(71) Applicant: RESET PHARMACEUTICALS, INC., New York, NY (US)

(72) Inventors: John Knight, Hereford (GB); Talbir Austin, Loughborough (GB)

(73) Assignee: RESET PHARMACEUTICALS, INC., New York, NY (US)

( * ) Notice: Subject to any disclaimer, the term of this patent is extended or adjusted under 35 U.S.C. 154(b) by 0 days.

(21) Appl. No.: 18/116,891

(22) Filed: Mar. 3, 2023

(65) Prior Publication Data

US 2023/0202978 A1 Jun. 29, 2023

Related U.S. Application Data

(60) Provisional application No. 63/322,697, filed on Mar. 23, 2022, provisional application No. 63/322,701, filed on Mar. 23, 2022, provisional application No. 63/322,703, filed on Mar. 23, 2022, provisional application No. 63/316,621, filed on Mar. 4, 2022, provisional application No. 63/316,627, filed on Mar. 4, 2022, provisional application No. 63/316,612, filed on Mar. 4, 2022.

(51) Int. Cl.
*C07D 209/16* (2006.01)
*A61P 25/00* (2006.01)

(52) U.S. Cl.
CPC ............ *C07D 209/16* (2013.01); *A61P 25/00* (2018.01); *C07B 2200/13* (2013.01)

(58) Field of Classification Search
CPC .......................... C07D 209/16; C07B 2200/13
See application file for complete search history.

(56) References Cited

U.S. PATENT DOCUMENTS 3,072,530 A 1/1963 Hofmann et al.
8,512,748 B2 8/2013 Pearnchob et al.
8,795,720 B2 8/2014 Madit
8,883,233 B2 11/2014 Gillessen et al.
8,907,153 B2 12/2014 Zhang et al.
9,044,402 B2 6/2015 Tygesen
9,050,343 B2 6/2015 Peters et al.
9,226,925 B1 1/2016 King et al.
9,421,266 B2 8/2016 King et al.
9,517,254 B2 12/2016 Sitchon et al.
9,522,120 B2 12/2016 Tengler et al.
9,549,901 B2 1/2017 Xiao et al.
9,554,989 B2 1/2017 Kaplan et al.
10,085,995 B2 10/2018 Lozinsky et al.
10,092,609 B2 10/2018 Wieser et al.
10,183,001 B1 1/2019 King et al.
10,188,083 B2 1/2019 Leo
10,478,429 B2 11/2019 Hughey et al.
10,519,175 B2 12/2019 Londesbrough et al.
10,596,378 B2 3/2020 Rustick
10,881,607 B2 1/2021 Schmitz et al.
10,947,257 B2 3/2021 Londesbrough et al.
10,954,259 B1 3/2021 Londesbrough et al.
11,000,534 B1 5/2021 Sippy
11,149,044 B2 10/2021 Londesbrough et al.
11,180,517 B2 11/2021 Londesbrough et al.
11,312,684 B1 4/2022 Nichols et al.
11,344,564 B1 5/2022 Sippy
11,447,510 B2 9/2022 Londesbrough et al.
11,505,564 B2 11/2022 Londesbrough et al.
11,629,159 B2 4/2023 Londesbrough et al.
11,667,607 B1 6/2023 Silverstone
11,707,447 B1 7/2023 Hagel et al.
2004/0116410 A1 6/2004 Cho et al.
2008/0293695 A1 11/2008 Bristol et al.
2011/0111029 A1 5/2011 Schmitz et al.
2012/0028960 A1 2/2012 King et al.
2012/0108510 A1 5/2012 Young et al.
2014/0178480 A1 6/2014 King et al.
2014/0275113 A1 9/2014 Wu et al.
2015/0366798 A1 12/2015 Lozinsky et al.
2016/0303361 A1 10/2016 Sameti et al.
(Continued)

FOREIGN PATENT DOCUMENTS

CA 3088384 A1 10/2020
CN 108619214 A 10/2018
(Continued)

OTHER PUBLICATIONS

Adwas et al., "Anxiety: Insights into Signs, Symptoms, Etiology, Pathophysiology, and Treatment", 2019, East African Scholars Journal of Medical Sciences, 2, pp. 580-591 (Year: 2019).*
Bains et al., "Major Depressive Disorder", 2023, StatPearls, pp. 1-7 (Year: 2023).*
Pohanka, "D-Lactic Acid as a Metabolite: Toxicology, Diagnosis, and Detection", 2020, Biomed Research International, 2020, pp. 1-9 (Year: 2020).*
Abramov et al., "Rational Coformer or Solvent Selection for Pharmaceutical Cocrystallization or Desolvation", Journal of Pharmaceutical Sciences, vol. 101, Oct. 2012, pp. 3687-3697.
Allen, "The Cambridge Structural Database: A Quarter of a Million Crystal Structures and Rising", Acta. Crystallogr. Section B, vol. 58, 2002, pp. 380-388.
Alvarez et al., "Polymorph Screening: Comparing a Semi-Automated Approach with a High Throughput Method", Crystal Growth and Design, vol. 9, 2009, pp. 4181-4188.
(Continued)

*Primary Examiner* — Brenda L Coleman
*Assistant Examiner* — Madeline E Braun
(74) *Attorney, Agent, or Firm* — MH2 Technology Law Group, LLP

(57) ABSTRACT

The invention relates to a co-crystal or salt comprising psilocin and a co-former. The co-crystal or salt is useful in methods of treating or preventing a disease or condition selected from depression, anxiety, death anxiety, demoralization, adjustment disorders, hopelessness, suicidal ideation, desire for hastened death, cocaine-related disorders, opioid-related disorders and stimulant-related disorders in a patient. A kit comprising the co-crystal or salt is also described.

6 Claims, 10 Drawing Sheets

(56) References Cited

U.S. PATENT DOCUMENTS

| | | | |
|---|---|---|---|
| 2017/0056347 A1 | 3/2017 | Glick et al. | |
| 2017/0313666 A1 | 11/2017 | Wu et al. | |
| 2018/0021326 A1 | 1/2018 | Stamets | |
| 2018/0055791 A1 | 3/2018 | Nichols et al. | |
| 2018/0343806 A1 | 12/2018 | Leo | |
| 2018/0360739 A1 | 12/2018 | Lorenz et al. | |
| 2019/0119310 A1 | 4/2019 | Londesbrough et al. | |
| 2019/0142851 A1 | 5/2019 | Chadeayne | |
| 2019/0167750 A1 | 6/2019 | Damaj | |
| 2019/0246591 A1 | 8/2019 | Leo | |
| 2019/0254988 A1 | 8/2019 | Archibald | |
| 2020/0060997 A1 | 2/2020 | Goren et al. | |
| 2020/0147038 A1 | 5/2020 | Russ et al. | |
| 2020/0179349 A1 | 6/2020 | Yun et al. | |
| 2020/0222656 A1 | 7/2020 | Rustick | |
| 2020/0370073 A1 | 11/2020 | Leo | |
| 2020/0390746 A1 | 12/2020 | Rands et al. | |
| 2020/0397752 A1 | 12/2020 | Perez Castillo et al. | |
| 2021/0015738 A1 | 1/2021 | Larosa et al. | |
| 2021/0015833 A1 | 1/2021 | Larosa et al. | |
| 2021/0236523 A1 | 8/2021 | Schindler et al. | |
| 2021/0275618 A1 | 9/2021 | Davidson et al. | |
| 2021/0292278 A1 | 9/2021 | Chadeayne | |
| 2021/0392933 A1 | 12/2021 | Lilly | |
| 2022/0007604 A1 | 1/2022 | Tudela | |
| 2022/0040106 A1 | 2/2022 | Malcolm et al. | |
| 2022/0054402 A1 | 2/2022 | Kaufman | |
| 2022/0125091 A1 | 4/2022 | Cave et al. | |
| 2022/0151993 A1* | 5/2022 | Ross | A61P 25/22 |
| 2022/0249591 A1 | 8/2022 | Mousset et al. | |
| 2022/0296720 A1 | 9/2022 | Reed et al. | |
| 2022/0323378 A1 | 10/2022 | Joseph | |
| 2022/0331344 A1 | 10/2022 | Greenbaum et al. | |
| 2022/0362320 A1 | 11/2022 | Ahvazi et al. | |
| 2022/0370413 A1 | 11/2022 | Barrow et al. | |
| 2022/0409584 A1 | 12/2022 | Bilai et al. | |
| 2023/0083927 A1 | 3/2023 | Gray | |
| 2023/0097076 A1 | 3/2023 | Raibar | |
| 2023/0112459 A1 | 4/2023 | Anand et al. | |
| 2023/0119714 A1 | 4/2023 | Londesbrough et al. | |
| 2023/0138974 A1 | 5/2023 | Jeganatth | |
| 2023/0202978 A1 | 6/2023 | Knight et al. | |

FOREIGN PATENT DOCUMENTS

| | | | |
|---|---|---|---|
| CN | 109350724 | A | 2/2019 |
| CN | 112300050 | A | 2/2021 |
| CZ | 307719 | B6 | 3/2019 |
| DE | 1156077 | B | 10/1963 |
| DE | 202020105085 | Y1 | 11/2020 |
| EP | 1605973 | A1 | 12/2005 |
| EP | 1389466 | B1 | 2/2007 |
| EP | 2136844 | B1 | 10/2018 |
| EP | 2768537 | B1 | 2/2019 |
| EP | 2611466 | B1 | 6/2019 |
| EP | 3603656 | A1 | 2/2020 |
| EP | 2654864 | B1 | 10/2020 |
| EP | 3277271 | B1 | 7/2021 |
| EP | 3862019 | A1 | 8/2021 |
| EP | 3957726 | A1 | 2/2022 |
| GB | 911946 | A | 12/1962 |
| GB | 912714 | A | 12/1962 |
| GB | 912715 | A | 12/1962 |
| GB | 2571696 | B | 5/2020 |
| GB | 2572023 | C | 2/2022 |
| GB | 2576059 | B | 6/2022 |
| GB | 2588506 | B | 7/2022 |
| GB | 2588505 | A | 8/2022 |
| WO | 2000044350 | A1 | 8/2000 |
| WO | 2002024865 | A2 | 3/2002 |
| WO | 2002085370 | A1 | 10/2002 |
| WO | 2003024481 | A2 | 3/2003 |
| WO | 2003026797 | A2 | 4/2003 |
| WO | 2004084939 | A2 | 10/2004 |
| WO | 2005039531 | A1 | 5/2005 |
| WO | 2005039546 | A2 | 5/2005 |
| WO | 2006007848 | A2 | 1/2006 |
| WO | 2006034343 | A2 | 3/2006 |
| WO | 2007054818 | A2 | 5/2007 |
| WO | 2008011051 | A1 | 1/2008 |
| WO | 2008128126 | A1 | 10/2008 |
| WO | 2008156707 | A1 | 12/2008 |
| WO | 2009021055 | A1 | 2/2009 |
| WO | 2009051837 | A2 | 4/2009 |
| WO | 2009089494 | A2 | 7/2009 |
| WO | 2009100384 | A2 | 8/2009 |
| WO | 2009149252 | A1 | 12/2009 |
| WO | 2009153019 | A1 | 12/2009 |
| WO | 2010089132 | A1 | 8/2010 |
| WO | 2010124089 | A2 | 10/2010 |
| WO | 2010138192 | A2 | 12/2010 |
| WO | 2011049954 | A2 | 4/2011 |
| WO | 2011106076 | A1 | 9/2011 |
| WO | 2011116189 | A1 | 9/2011 |
| WO | 2011143242 | A2 | 11/2011 |
| WO | 2011150240 | A1 | 12/2011 |
| WO | 2012064667 | A2 | 5/2012 |
| WO | 2012074588 | A2 | 6/2012 |
| WO | 2012085919 | A2 | 6/2012 |
| WO | 2013068949 | A1 | 5/2013 |
| WO | 2013113325 | A1 | 8/2013 |
| WO | 2013185032 | A1 | 12/2013 |
| WO | 2014165679 | A1 | 10/2014 |
| WO | 2015081166 | A1 | 6/2015 |
| WO | 2014140925 | A3 | 7/2015 |
| WO | 2015168022 | A1 | 11/2015 |
| WO | 2016001921 | A2 | 1/2016 |
| WO | 2017013031 | A1 | 1/2017 |
| WO | 2017141104 | A2 | 8/2017 |
| WO | 2018022664 | A1 | 2/2018 |
| WO | 2018025089 | A2 | 2/2018 |
| WO | 2018135943 | A1 | 7/2018 |
| WO | 2018141063 | A1 | 8/2018 |
| WO | 2018148605 | A1 | 8/2018 |
| WO | 2018170596 | A1 | 9/2018 |
| WO | 2018183115 | A1 | 10/2018 |
| WO | 2018195455 | A1 | 10/2018 |
| WO | 2018200959 | A1 | 11/2018 |
| WO | 2018209341 | A1 | 11/2018 |
| WO | 2019025763 | A1 | 2/2019 |
| WO | 2019064031 | A1 | 4/2019 |
| WO | 2019071213 | A1 | 4/2019 |
| WO | 2019073379 | A1 | 4/2019 |
| WO | 2019079742 | A1 | 4/2019 |
| WO | 2019081764 | A1 | 5/2019 |
| WO | 2019092569 | A1 | 5/2019 |
| WO | 2019109124 | A1 | 6/2019 |
| WO | 2019122525 | A1 | 6/2019 |
| WO | 2019140403 | A1 | 7/2019 |
| WO | 2019144140 | A1 | 7/2019 |
| WO | 2019161050 | A1 | 8/2019 |
| WO | 2019161231 | A1 | 8/2019 |
| WO | 2019173797 | A1 | 9/2019 |
| WO | 2019175290 | A1 | 9/2019 |
| WO | 2019178360 | A1 | 9/2019 |
| WO | 2019180309 | A1 | 9/2019 |
| WO | 2019195813 | A1 | 10/2019 |
| WO | 2019200482 | A1 | 10/2019 |
| WO | 2019207319 | A1 | 10/2019 |
| WO | 2019246532 | A2 | 12/2019 |
| WO | 2020023084 | A1 | 1/2020 |
| WO | 2020041329 | A1 | 2/2020 |
| WO | 2020097320 | A1 | 5/2020 |
| WO | 2020142259 | A1 | 7/2020 |
| WO | 2020157569 | A1 | 8/2020 |
| WO | 2020169850 | A1 | 8/2020 |
| WO | 2020169851 | A1 | 8/2020 |
| WO | 2020176599 | A1 | 9/2020 |
| WO | 2020181194 | A1 | 9/2020 |
| WO | 2020185581 | A2 | 9/2020 |
| WO | 2020185711 | A1 | 9/2020 |
| WO | 2020185712 | A1 | 9/2020 |
| WO | 2020212948 | A | 10/2020 |
| WO | 2020212948 | A1 | 10/2020 |

(56) References Cited

FOREIGN PATENT DOCUMENTS

| | | | |
|---|---|---|---|
| WO | 2020212951 A1 | 10/2020 | |
| WO | 2020212952 A1 | 10/2020 | |
| WO | 2020241958 A1 | 12/2020 | |
| WO | 2020245133 A1 | 12/2020 | |
| WO | 2020263941 A1 | 12/2020 | |
| WO | 2021003467 A1 | 1/2021 | |
| WO | 2021016423 A1 | 1/2021 | |
| WO | 2021005310 A1 | 2/2021 | |
| WO | 2021016710 A1 | 2/2021 | |
| WO | 2021019023 A1 | 2/2021 | |
| WO | 2021030571 A1 | 2/2021 | |
| WO | 2021041407 A1 | 3/2021 | |
| WO | 2021052989 A1 | 3/2021 | |
| WO | 2021067626 A2 | 4/2021 | |
| WO | 2021067961 A1 | 4/2021 | |
| WO | 2021072530 A1 | 4/2021 | |
| WO | 2021074448 A1 | 4/2021 | |
| WO | 2021076849 A1 | 4/2021 | |
| WO | 2021081138 A1 | 4/2021 | |
| WO | 2021086513 A1 | 5/2021 | |
| WO | 2021089872 A1 | 5/2021 | |
| WO | 2021092515 A1 | 5/2021 | |
| WO | 2021097452 A2 | 5/2021 | |
| WO | 2021101926 A1 | 5/2021 | |
| WO | 2021108911 A1 | 6/2021 | |
| WO | 2021113986 A1 | 6/2021 | |
| WO | 2021116503 A2 | 6/2021 | |
| WO | 2021138564 A1 | 7/2021 | |
| WO | 2021139874 A1 | 7/2021 | |
| WO | 2021155467 A1 | 8/2021 | |
| WO | 2021155468 A1 | 8/2021 | |
| WO | 2021158888 A1 | 8/2021 | |
| WO | 2021159213 A1 | 8/2021 | |
| WO | 2021168082 A1 | 8/2021 | |
| WO | 2021173273 A1 | 9/2021 | |
| WO | 2021173989 A1 | 9/2021 | |
| WO | 2021178579 A1 | 9/2021 | |
| WO | 2021179091 A1 | 9/2021 | |
| WO | 2021183490 A2 | 9/2021 | |
| WO | 2021188782 A1 | 9/2021 | |
| WO | 2021188812 A1 | 9/2021 | |
| WO | 2021188870 A1 | 9/2021 | |
| WO | 2021194796 A1 | 9/2021 | |
| WO | 2021202730 A1 | 10/2021 | |
| WO | 2021207137 A1 | 10/2021 | |
| WO | 2021207824 A1 | 10/2021 | |
| WO | 2021209815 A1 | 10/2021 | |
| WO | 2021211358 A1 | 10/2021 | |
| WO | 2021216489 A1 | 10/2021 | |
| WO | 2021-226416 A1 | 11/2021 | |
| WO | 2021222885 A1 | 11/2021 | |
| WO | 2021225796 A1 | 11/2021 | |
| WO | 2021226041 A1 | 11/2021 | |
| WO | 2021226542 A1 | 11/2021 | |
| WO | 2021236759 A2 | 11/2021 | |
| WO | 2021243460 A1 | 12/2021 | |
| WO | 2021243461 A1 | 12/2021 | |
| WO | 2021248087 A2 | 12/2021 | |
| WO | 2021250434 A1 | 12/2021 | |
| WO | 2021252538 A2 | 12/2021 | |
| WO | 2021253116 A1 | 12/2021 | |
| WO | 2021257586 A1 | 12/2021 | |
| WO | 2021262871 A1 | 12/2021 | |
| WO | 2022000091 A1 | 1/2022 | |
| WO | 2022010937 A1 | 1/2022 | |
| WO | 2022011350 A1 | 1/2022 | |
| WO | 2022016289 A1 | 1/2022 | |
| WO | 2022018709 A1 | 1/2022 | |
| WO | 2022023812 A1 | 2/2022 | |
| WO | 2022031551 A1 | 2/2022 | |
| WO | 2022031552 A1 | 2/2022 | |
| WO | 2022031566 A1 | 2/2022 | |
| WO | 2022031907 A1 | 2/2022 | |
| WO | 2022032147 A1 | 2/2022 | |
| WO | 2022038170 A1 | 2/2022 | |
| WO | 2022038299 A1 | 2/2022 | |
| WO | 2022040802 A1 | 3/2022 | |
| WO | 2022043227 A1 | 3/2022 | |
| WO | 2022047579 A1 | 3/2022 | |
| WO | 2022047580 A1 | 3/2022 | |
| WO | 2022047583 A1 | 3/2022 | |
| WO | 2022049574 A | 3/2022 | |
| WO | 2022051578 A1 | 3/2022 | |
| WO | 2022051670 A1 | 3/2022 | |
| WO | 2022053892 A2 | 3/2022 | |
| WO | 2022061196 A1 | 3/2022 | |
| WO | 2022061242 A1 | 3/2022 | |
| WO | 2022069690 A2 | 4/2022 | |
| WO | 2022072808 A1 | 4/2022 | |
| WO | 2022079574 A1 | 4/2022 | |
| WO | 2022081549 A1 | 4/2022 | |
| WO | 2022084480 A1 | 4/2022 | |
| WO | 2022094054 A1 | 5/2022 | |
| WO | 2022094719 A1 | 5/2022 | |
| WO | 2022104475 A1 | 5/2022 | |
| WO | 2022106947 A1 | 5/2022 | |
| WO | 2022115796 A1 | 6/2022 | |
| WO | 2022115798 A2 | 6/2022 | |
| WO | 2022115944 A1 | 6/2022 | |
| WO | 2022115960 | 6/2022 | |
| WO | 2022120181 A1 | 6/2022 | |
| WO | 2022120289 A1 | 6/2022 | |
| WO | 2022120475 A1 | 6/2022 | |
| WO | 2022123232 A1 | 6/2022 | |
| WO | 2022125616 A1 | 6/2022 | |
| WO | 2022125949 A1 | 6/2022 | |
| WO | 2022132691 A1 | 6/2022 | |
| WO | 2022137107 A1 | 6/2022 | |
| WO | 2022140841 A1 | 7/2022 | |
| WO | 2022150530 A1 | 7/2022 | |
| WO | 2022150563 A1 | 7/2022 | |
| WO | 2022150675 A1 | 7/2022 | |
| WO | 2022150840 A1 | 7/2022 | |
| WO | 2022150854 A1 | 7/2022 | |
| WO | 2022155284 A1 | 7/2022 | |
| WO | 2022155352 A1 | 7/2022 | |
| WO | 2022155591 A1 | 7/2022 | |
| WO | 2022155751 A1 | 7/2022 | |
| WO | 2022165387 A1 | 8/2022 | |
| WO | 2022170438 A1 | 8/2022 | |
| WO | 2022170442 A1 | 8/2022 | |
| WO | 2022173584 A1 | 8/2022 | |
| WO | 2022173888 A1 | 8/2022 | |
| WO | 2022175821 A1 | 8/2022 | |
| WO | 2022177716 A1 | 8/2022 | |
| WO | 2022182527 A1 | 9/2022 | |
| WO | 2022183292 A1 | 9/2022 | |
| WO | 2022187973 A1 | 9/2022 | |
| WO | 2022189855 A1 | 9/2022 | |
| WO | 2022192215 A1 | 9/2022 | |
| WO | 2022195011 A1 | 9/2022 | |
| WO | 2022195489 A2 | 9/2022 | |
| WO | WO-2022192097 A1 * | 9/2022 | ......... A61K 31/4045 |
| WO | 2022204802 A2 | 10/2022 | |
| WO | 2022207746 A1 | 10/2022 | |
| WO | 2022212585 A1 | 10/2022 | |
| WO | 2022212789 A1 | 10/2022 | |
| WO | 2022212854 A1 | 10/2022 | |
| WO | 2022221554 A2 | 10/2022 | |
| WO | 2022221942 A1 | 10/2022 | |
| WO | 2022226493 A1 | 10/2022 | |
| WO | 2022232933 A1 | 11/2022 | |
| WO | 2022235500 A1 | 11/2022 | |
| WO | 2022235514 A1 | 11/2022 | |
| WO | 2022235529 A1 | 11/2022 | |
| WO | 2022235531 A1 | 11/2022 | |
| WO | 2022235912 A1 | 11/2022 | |
| WO | 2022236130 A1 | 11/2022 | |
| WO | 2022236407 A1 | 11/2022 | |
| WO | 2022240853 A1 | 11/2022 | |
| WO | 2022243285 A1 | 11/2022 | |
| WO | 2022246572 A1 | 12/2022 | |
| WO | 2022248635 A2 | 12/2022 | |
| WO | 2022251699 A1 | 12/2022 | |

(56) References Cited

FOREIGN PATENT DOCUMENTS

| | | | | | |
|---|---|---|---|---|---|
| WO | 2022256720 | A2 | 12/2022 | | |
| WO | 2022259046 | A1 | 12/2022 | | |
| WO | 2022261058 | A1 | 12/2022 | | |
| WO | 2022261263 | A1 | 12/2022 | | |
| WO | 2022261761 | A1 | 12/2022 | | |
| WO | 2022265878 | A1 | 12/2022 | | |
| WO | 2022269264 | A1 | 12/2022 | | |
| WO | 2022269265 | A1 | 12/2022 | | |
| WO | 2022269266 | A1 | 12/2022 | | |
| WO | 2022269267 | A1 | 12/2022 | | |
| WO | 2022271841 | A1 | 12/2022 | | |
| WO | 2022272176 | A1 | 12/2022 | | |
| WO | WO-2022251169 | A1 * | 12/2022 | ........... | C07D 209/16 |
| WO | 2023278131 | A1 | 1/2023 | | |
| WO | 2023278403 | A2 | 1/2023 | | |
| WO | 2023283386 | A2 | 1/2023 | | |
| WO | 2023287283 | A1 | 1/2023 | | |
| WO | 2023010203 | A1 | 2/2023 | | |
| WO | 2023012524 | A2 | 2/2023 | | |
| WO | 2023012691 | A1 | 2/2023 | | |
| WO | 2023023347 | A1 | 2/2023 | | |
| WO | 2023023857 | A1 | 3/2023 | | |
| WO | 2023028086 | A1 | 3/2023 | | |
| WO | 2023043794 | A1 | 3/2023 | | |
| WO | 2023043826 | A1 | 3/2023 | | |
| WO | 2023044135 | A1 | 3/2023 | | |
| WO | 2023044169 | A2 | 3/2023 | | |
| WO | 2023044556 | A1 | 3/2023 | | |
| WO | 2023044577 | A1 | 3/2023 | | |
| WO | 2023053090 | A1 | 4/2023 | | |
| WO | 2023055860 | A1 | 4/2023 | | |
| WO | 2023055992 | A1 | 4/2023 | | |
| WO | 2023056561 | A1 | 4/2023 | | |
| WO | 2023060302 | A1 | 4/2023 | | |
| WO | 2023064840 | A1 | 4/2023 | | |
| WO | 2023065012 | A1 | 4/2023 | | |
| WO | 2023067509 | A1 | 4/2023 | | |
| WO | 2023077234 | A1 | 5/2023 | | |
| WO | 2023077245 | A1 | 5/2023 | | |
| WO | 2023081109 | A1 | 5/2023 | | |
| WO | 2023081829 | A2 | 5/2023 | | |
| WO | 2023081833 | A1 | 5/2023 | | |
| WO | 2023081837 | A2 | 5/2023 | | |
| WO | 2023081842 | A2 | 5/2023 | | |
| WO | 2023081892 | A1 | 5/2023 | | |
| WO | 2023086252 | A1 | 5/2023 | | |
| WO | 2023086962 | A1 | 5/2023 | | |
| WO | 2023091717 | A1 | 5/2023 | | |
| WO | 2023091721 | A1 | 5/2023 | | |
| WO | 2023108164 | A2 | 6/2023 | | |
| WO | 2023108167 | A1 | 6/2023 | | |
| WO | 2023108260 | A1 | 6/2023 | | |
| WO | 2023108277 | A1 | 6/2023 | | |
| WO | 2023114097 | A1 | 6/2023 | | |
| WO | 2023114529 | A2 | 6/2023 | | |
| WO | 2023115060 | A1 | 6/2023 | | |
| WO | 2023122320 | A1 | 6/2023 | | |
| WO | 2023130075 | A2 | 7/2023 | | |
| WO | 2023130191 | A1 | 7/2023 | | |
| WO | 2023135595 | A1 | 7/2023 | | |
| WO | 2023137094 | A1 | 7/2023 | | |
| WO | 2023137325 | A1 | 7/2023 | | |
| WO | 2023146579 | A1 | 8/2023 | | |

OTHER PUBLICATIONS

Anderson et al., "Occurrence and Use of Hallucinogenic Mushrooms Containing Psilocybin Alkaloids", Nordic Council of Ministers, Copenhagen, 2009, 124 pages.
Baker et al., "Molecular Structures of Hallucinogenic Substances: Lysergic Acid Diethylamide, Psilocybin, and 2,4,5-Trimethoxyamphetamine", Molecular Pharmacology, 1973, vol. 9, pp. 23-32.
Beck et al., "An Inventory for Measuring Depression", Archives of General Psychiatry, vol. 4, Jun. 1961, 11 Pages.
Becke, "Density-Functional Exchange-Energy Approximation With Correct Asymptotic Behavior", The American Physical Society, vol. 38, No. 6, Sep. 15, 1988, pp. 3098-3100.
Breeksema et al., "Treatment With Psilocybin: Applications for Patients With Psychiatric Disorders", Nederlands Tijdschrift voor Geneeskunde; vol. 165; No. 4; Jan. 25, 2021, 2 pages (Reaxys database extract, database accession No. XRN = 37140626).
Cashman et al., "A Specific Microcrystalline Test for Indolamine Derivatives", Michrochemical Journal, vol. 20, 1975, pp. 511-518.
Datta et al., "Crystal Structures of Drugs: Advances in Determination, Prediction and Engineering", Nature, vol. 3, Jan. 2004, pp. 42-57.
Greenan et al., "Preparation and Characterization of Novel Crystalline Solvates and Polymorphs of Psilocybin and Identification of Solid Forms Suitable for Clinical Development", 2020, 29 pages (https://www.researchgate.net/publication/339238710_Preparation_and_Characterization_of_Novel_Crystalline_Solvates_and_Polymorphs_of_Psilocybin_and_Identification_of_Solid_Forms_Suitable_for_Clinical_Development).
Hofmann, et al., "Psilocybin, A Psychotropic Agent From the Mexican Intoxicating Mushroom *Psilocybe mexicana* Home", Exerientia, vol. 14, 1958, pp. 107-109 (with machine English translation).
Hofmann, "Psychotomimetic Drugs Chemical and Pharmacological Aspects", Acta Physiol. Pharmacol. Neerlandica, vol. 8, 1959, pp. 240-258.
Jones et al., "Pharmaceutical Cocrystals: An Emerging Approach to Physical Property Enhancement", MRS Bulletin, vol. 31, Nov. 2006, pp. 875-879.
Kargbo et al., "Direct Phosphorylation of Psilocin Enables Optimized cGMP Kilogram-Scale Manufacture of Psilocybin", ACS Omega, 2020, vol. 5, pp. 16959-16966.
Kuhnert-Brandstatter et al., "Polymorphic modifications and solvates of psilocin and psilocybin", Arch Pharm., vol. 309, No. 76, 1976 (with machine English translation) pp. 625-631.
Liaw et al., "Classification and Regression by RandomForest", M. R. News, vol. 2, No. 3, Dec. 2022, pp. 18-22.
Loschen et al., "Solubility Prediction, Solvate and Cocrystal Screening as Tools for Rational Crystal Engineering: Solubility Prediction, Solvate and Cocrystal Screening", Journal of Pharmacy and Pharmacology, vol. 67, Jun. 2015, pp. 803-811.
Loschen et al., "New Developments in Prediction of Solid-state Solubility and Cocrystallization Using Cosmo-rs Theory", Computational Pharmaceutical Solid State Chemistry, 2016, pp. 211-234.
McNamara et al., "Use of a Glutaric Acid Cocrystal to Improve Oral Bioavailability of a Low Solubility API", Pharmaceutical Research, vol. 23, No. 8, Aug. 2006, 11 pages.
Meltzer et al., "Stimulation of Rat Prolactin Secretion by Indolealkylamine Hallucinogens", Psychopharmacology, vol. 56, 1978, pp. 255-259.
Migliaccio et al., "Comparison of Solution Conformational Preferences for the Hallucinogens Bufotenin and Psilocin Using 360-MHz Proton NMR Spectroscopy", J. Med. Chem., vol. 24, 1981, pp. 206-209.
Nichols et al., "Improvements to the Synthesis of Psilocybin and a Facile Method for Preparing the O-Acetyl Prodrug of Psilocin", Synthesis, No. 6, 1999, pp. 935-938.
Ono et al., "Studies on Hallucinogens. V Synthesis of Psilocybin", Bulletin of National Institute of Hygienic Sciences, vol. 92, 1974, pp. 41-43 (with machine English Translation).
Perdew, "Density-Functional Approximation for the Correlation Energy ofthe Inhomogeneous Electron Gas", Physical Review B, vol. 33, No. 12, Jun. 15, 1986, pp. 8822-8824.
Perdew, "Erratum: Density-Functional Approximation for the Correlation Energy of the Inhomogeneous Electron Gas", Physical Review B, vol. 34, No. 10, Nov. 15, 1986, p. 7406.
Petcher et al., "Crystal Structures of the Teonanácatl Hallucinogens. Part II. Psilocin, C12 H15N20", J. Chem. Soc., Perkin Trans., 1974, pp. 946-948.
Rager et al., "Cocrystal Formation from Solvent Mixtures", Crystal Growth & Design, vol. 10, No. 7, 2010, pp. 3237-3241.

(56) References Cited

OTHER PUBLICATIONS

Repke et al., "Psilocin Analogs 11. Synthesis of 3-[2-(Dialkylamino)ethyl]-, 3-[2-(N-Methyl-N-alkylamino)ethyl]-, and 3-[2-(Cycloalkylamino)ethyl]indol-4-ols", Journal of Hetrocyclic Chemistry, vol. 18, No. 185, Jan. 1981, pp. 175-179.
Rodríguez-Spong et al., "General Principles of Pharmaceutical Solid Polymorphism: A Supramolecular Perspective", Advanced Drug Delivery Reviews, vol. 56, 2004, pp. 241-274.
Rosenfeld et al., "Assessing Hopelessness in Terminally Ill Cancer Patients: Development of the Hopelessness Assessment in Illness Questionnaire", Psychol Assess, vol. 23, No. 2, Jun. 2011, pp. 325-336.
Schäfer et al., "Fully optimized contracted Gaussian basis sets of triple zeta valence quality for atoms Li to Kr", J. Chem. Phys., vol. 100, No. 8, Apr. 15, 1994, pp. 5829-5835.
Schultheiss et al., "Pharmaceutical Cocrystals and Their Physicochemical Properties", Crystal Growth & Design, vol. 9, No. 6, 2009, pp. 2950-2967.
Stahl et al., "Monographs on Acids and Bases", Handbook of Pharmaceutical Salts Properties, Selection, and Use, 2002, pp. 329-335.
Stahl et al., "Appendix", Handbook of Pharmaceutical Salts Properties, Selection, and Use, 2002, pp. 265-327.
Stahl et al., "Handbook of Pharmaceutical Salts Properties, Selection, and Use", 2008, pp. 103-170.
Steinbeck et al., "Recent Developments of the Chemistry Development Kit (CDK)—An Open-Source Java Library for Chemo- and Bioinformatics", J. Chem. Inf. Comput. Sci. Curr Pharm Des., vol. 12, No. 17, 2006, pp. 2110-2120.
Stockwatch Business Reporter, "Shell Summary for Jan. 7, 2021", Stockwatch Daily, Jan. 8, 2021, 3 pages.
Szegezdi et al., "Prediction of Dissociation Constant Using Microconstants", American Chemical Society National Meeting, Mar. 28-Apr. 1, 2001, updaed Apr. 15, 2004, 2 pages.
Templer, "The Construction and Validation of a Death Anxiety Scale" The Journal of General Psychology, 1970, vol. 82, No. 2, pp. 165-177.
Troxler et al., "Modification products of psilocybin and psilocin", Communication on Synthetic Indole Compounds, vol. XLII, File VI, No. 226, 1959, pp. 2073-2103 (with machine English translation).
Weber et al., "Crystal Structures of the Teonanácatl Hallucinogens. Part 1. Psilocybin C12H17N2O4P", J. C. S. Perkin II, Jan. 1, 1974, pp. 942-946.
Zigmond et al., "The Hospital Anxiety and Depression Scale", Acta. Psychiatr. Scand., vol. 67, 1983, pp. 361-370.
Eberhard, Michael, International Search Report and Written Opinion dated May 25, 2023 for corresponding International Application No. PCT/US2023/014417, 11 pages.
Beck, "Psychometric Properties of the Beck Depression Inventory: Twenty-Five Ye ars of Evaluation", Clinical Psychology Review, 1988, vol. 8, pp. 77-100.
Sherwood et al., "An Improved, Practical, and Scalable Five-Step Synthesis of Psilocybin", Synthesis, 2020, vol. 52, pp. 688-694.
Kang et al., "Theoretical Studies on the Conformations of Psilocin and Mescaline", Molecular Pharmacology, 1973, vol. 9, 9 pp. 640-648.
Kissane et al., "The Demoralization Scale: A Report of Its Development and Preliminary Validation", Journal of Palliative Care, 2004, vol. 20, No. 4, pp. 269-276.
David et al., (2012) Impact of the counterion on the solubility and physicochemical properties of salts of carboxylic acid drugs, Drug Development and Industrial Pharmacy, 38:1, 93-103, DOI: 10.3109/03639045.2011.592530 (Year: 2012).
Liu et al. Parkinsonism Caused by Viral Encephalitis Affecting the Bilateral Substantia Nigra., Clinical Neurology, 2019, 29:571-573 (Year: 2019).
Jicha et al. (Hippocampal Sclerosis . . . , American Academy of Neurology, 2019, p. 208-233 (Year: 2019).
Teylan et al., Clinical diagnoses, Laboratory investigation, 2019, 99:1049-1055 (Year: 2019).
Bauer, The Pharmacology of Psilocybin and Psilocin, Psychedelic Science Review, 2019, p. 1-6 (Year: 2019).
Yan et al. Crystal Structures, Stability, and Solubility Evaluation, Cryst. Growth Des., 2020, p. 1079-1087 (Year: 2020).
Cambridge Med Chem Consulting. Bioisosteric Replacements, CMC, 2021, p. 1-9 (Year: 2021).
Harvard Health Publishing. What Causes Depression?, Harvard Medical School, 2022, p. 1-10 (Year: 2022).
Stahl et al., "Handbook of Pharmaceutical Salts (2nd ed.)", 2011, 5 pages.

* cited by examiner

CO-CRYSTALS OR SALTS OF PSILOCIN AND METHODS OF TREATMENT THEREWITH

CROSS-REFERENCE TO RELATED APPLICATIONS

This application claims the benefit of, and relies on the filing date of, U.S. Provisional Patent Application No. 63/316,612, filed 4 Mar. 2022, U.S. Provisional Patent Application No. 63/316,621, filed 4 Mar. 2022, U.S. Provisional Patent Application No. 63/316,627, filed 4 Mar. 2022, U.S. Provisional Patent Application No. 63/322,697, filed 23 Mar. 2022, U.S. Provisional Patent Application No. 63/322,701, filed 23 Mar. 2022, and U.S. Provisional Patent Application No. 63/322,703, filed 23 Mar. 2022, the entire disclosures of which are hereby incorporated by reference in their entirety.

FIELD OF THE INVENTION

The present invention relates to co-crystals or salts comprising psilocin. Methods of treating and preventing conditions using the co-crystals or salts are also described.

BACKGROUND OF THE INVENTION

Psilocin (4-hydroxy-N,N-dimethyltryptamine) is a tryptamine serotoninergic psychedelic. The IUPAC name of psilocin is 3-(2-(dimethylamino)ethyl)-1H-indol-4-ol. The structure of psilocin is shown below.

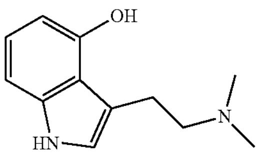

Pharmaceutical compounds may exist in a number of different solid forms. This includes crystalline forms, salts, hydrates and solvates, and amorphous phases. Different solid forms of a pharmaceutical compound have different properties, for instance in relation to crystallinity, chemical and physical stability, and processability. WO 2022/251169 describes solid forms of psilocin, including solid forms comprising stearic acid or DL-lactic acid.

Psilocin is currently being investigated as a potential treatment for various psychiatric disorders (for example, demoralization, depression, anxiety and adjustment disorders) in a variety of clinical settings. There is accordingly a need to develop new forms of psilocin with particularly advantageous properties for use in such treatments.

SUMMARY OF THE INVENTION

It is a finding of the invention that a co-crystal comprising psilocin and a co-former provides a crystalline form with favourable properties such as high crystallinity and/or beneficial morphology. The co-crystal also has good physical and chemical stability, as well as suitability for secondary processing (including improved flowability and compaction). The use of the co-crystal may also provide modulation of the dissolution rate and kinetic solubility, which can be useful in pharmaceutical settings.

In particular, the inventors have found that co-crystals or salts of psilocin formed with a co-former selected from L-lactic acid, decanoic acid, ethyl maltol, oleic acid, palmitic acid, p-coumaric acid, propyl gallate and stearic acid are well suited to pharmaceutical formulation.

The present invention accordingly provides a co-crystal comprising psilocin and a co-former, wherein the co-former is selected from L-lactic acid, decanoic acid, ethyl maltol, oleic acid, palmitic acid, p-coumaric acid, propyl gallate and stearic acid. The invention alternatively provides a salt comprising psilocin and a co-former, wherein the co-former is selected from L-lactic acid, decanoic acid, ethyl maltol, oleic acid, palmitic acid, p-coumaric acid, propyl gallate and stearic acid.

The invention further provides a pharmaceutical composition comprising a co-crystal or salt as described herein; and a pharmaceutically acceptable excipient or diluent.

The invention also provides a method of treating or preventing a disease or condition selected from psychological, neurological and central nervous system disorders in a patient, the method comprising administering a therapeutically effective amount of a co-crystal or salt as described herein to the patient.

Also provided by the invention is a kit comprising a co-crystal, salt or a pharmaceutical composition as described herein; and instructions for use of the co-crystal, salt or pharmaceutical composition in a method of treating or preventing a disease or condition as described herein.

DETAILED DESCRIPTION OF THE INVENTION

Figure 1:
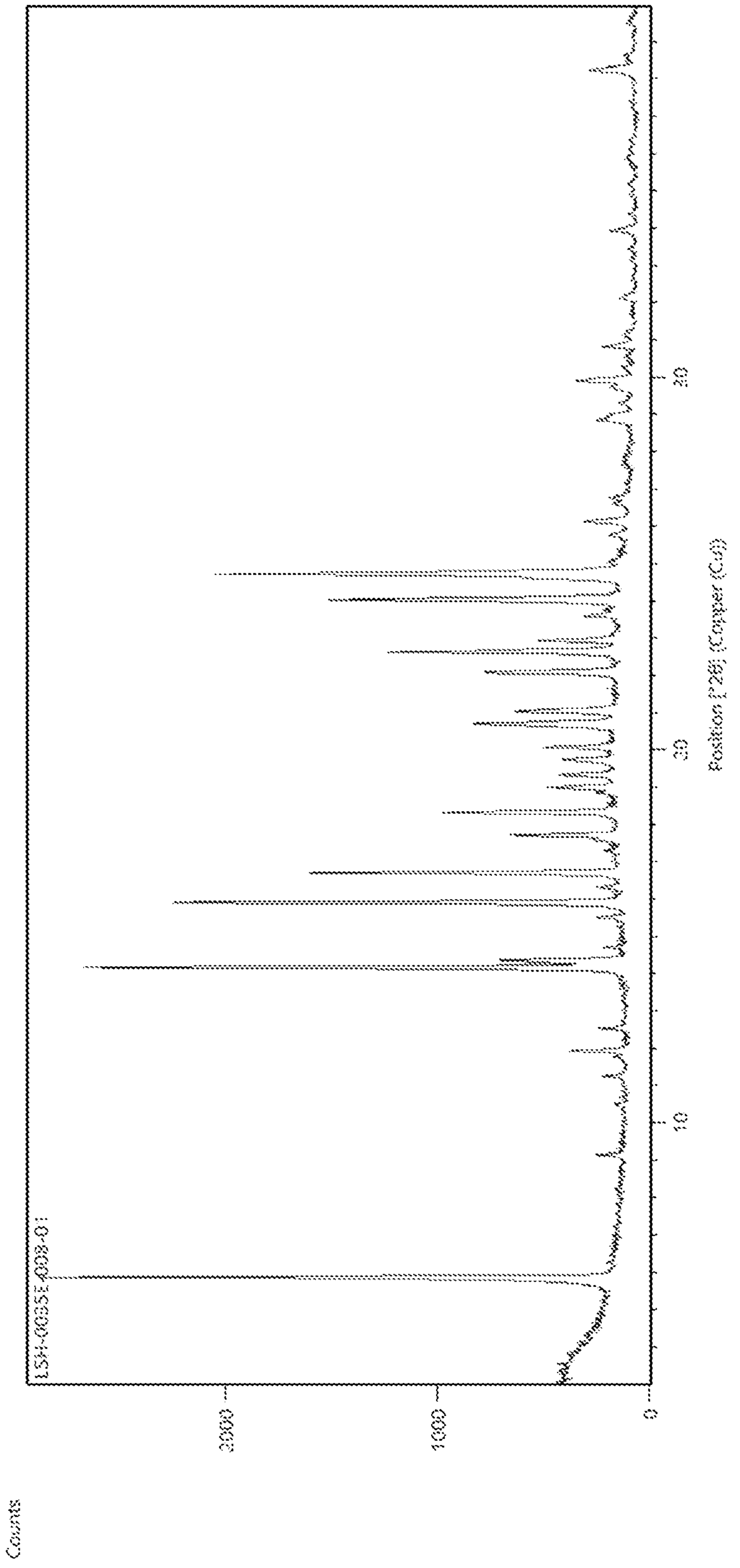
FIG. 1 shows the XRPD 2θ diffractogram of Pattern 1 of a co-crystal comprising psilocin and decanoic acid.

The co-crystal according to the invention comprises psilocin and a co-former.

A co-crystal is a solid crystalline material comprising two or more different molecular and/or ionic compounds, for instance an active agent and a co-former. The active agent and the co-former are in the same crystal lattice. A co-crystal is typically neither a solvate nor a simple salt, although a co-crystal may additionally be hydrated or solvated (i.e. it may comprise the active agent, the co-former and water or solvent molecules) or one of the components in the co-crystal (e.g. the co-former) may itself be a salt.

A co-crystal may comprise an active agent and a co-former. The active agent and co-former are typically arranged in a regular repeating crystal structure. A co-crystal has a different crystal structure to that of either the active agent or co-former alone.

The co-crystal may consist essentially of psilocin and the co-former and, optionally, water or a solvent. If the co-crystal comprises a co-former and one or more additional co-formers, the co-crystal may consist essentially of psilocin and the co-formers and, optionally water or a solvent. The co-crystal may comprise at least 90% by weight, at least 95% by weight or at least 99% by weight of psilocin, the co-former(s) and optionally water or a solvent. The co-crystal may consist essentially of psilocin and the co-former(s). The co-crystal may comprise at least 90% by weight, at least 95% by weight or at least 99% by weight of psilocin and the co-former(s). The co-crystal may consist of psilocin and the co-former(s). The term "consist essentially of" as used here means that the co-crystal contains only the specified components (i.e. psilocin, the co-former(s) and, optionally, water or a solvent) and any additional component which does not materially affect the essential characteristics or function of the specified components.

The co-former is typically selected from L-lactic acid, decanoic acid, ethyl maltol, oleic acid, palmitic acid, p-coumaric acid, propyl gallate and stearic acid. Preferably, the co-former is selected from L-lactic acid, decanoic acid and propyl gallate. More preferably, the co-former is L-lactic acid.

In one embodiment, the co-crystal is a co-crystal comprising psilocin and decanoic acid, wherein the molar ratio of psilocin:decanoic acid is about 1:1.2. The molar ratio may be 1:1.2. In one embodiment, the molar ratio is about 1:1. The molar ratio may be 1:1. Alternatively, the molar ratio may be about 1:0.5, 1:1.5 or 1:2.

In one embodiment, the co-crystal is a co-crystal comprising psilocin and ethyl maltol, wherein the molar ratio of psilocin:ethyl maltol is about 1:0.8. The molar ratio may be 1:0.8. Alternatively, the molar ratio may be about 1:0.5, 1:1, 1:1.5 or 1:2.

In one embodiment, the co-crystal is a co-crystal comprising psilocin and L-lactic acid, wherein the molar ratio of psilocin:L-lactic acid is about 1:1. The molar ratio may be 1:1. Alternatively, the molar ratio may be about 1:0.5, 1:1.5 or 1:2.

In one embodiment, the co-crystal is a co-crystal comprising psilocin and oleic acid, wherein the molar ratio of psilocin:oleic acid is about 1:1.1. The molar ratio may be 1:1 or 1:1.1. Alternatively, the molar ratio may be about 1:0.5, 1:1.5 or 1:2.

In one embodiment, the co-crystal is a co-crystal comprising psilocin and palmitic acid, wherein the molar ratio of psilocin:palmitic acid is about 1:1. The molar ratio may be 1:1. Alternatively, the molar ratio may be about 1:0.5, 1:1.5 or 1:2.

In one embodiment, the co-crystal is a co-crystal comprising psilocin and p-coumaric acid, wherein the molar ratio of psilocin:p-coumaric acid is about 1:1. The molar ratio may be 1:1. Alternatively, the molar ratio may be about 1:0.5, 1:1.5 or 1:2.

In one embodiment, the co-crystal is a co-crystal comprising psilocin and propyl gallate, wherein the molar ratio of psilocin:propyl gallate is about 1:0.6. The molar ratio may be 1:0.5 or 1:0.6. Alternatively, the molar ratio may be about 1:1, 1:1.5 or In one embodiment, the co-crystal is a co-crystal comprising psilocin and stearic acid, wherein the molar ratio of psilocin:stearic acid is about 1:1.6. The molar ratio may be 1:1.5 or 1:1.6. In one embodiment, the molar ratio of psilocin:stearic acid is about 1:1. The molar ratio may be 1:1. Alternatively, the molar ratio may be about 1:0.5 or 1:2.

As stated herein, values of °2θ are as measured using an x-ray wavelength of CuK $\alpha_1$ radiation (λ=1.54060 Å). If an x-ray powder diffraction pattern comprises a peak, the relative intensity of that peak is typically at least 5% or at least 10%. Error margins for the values of °2θ are typically ±0.2°2θ, but the error margin may alternatively be ±0.1°2θ.

The co-crystal comprising psilocin and decanoic acid may be in the form of the crystalline form designated as Pattern 1. Pattern 1 of the co-crystal comprising psilocin and decanoic acid typically has an x-ray powder diffraction (XRPD) pattern comprising peaks at 5.9°, 14.2° and 15.9°±0.2°2θ.

The XRPD pattern of Pattern 1 of the co-crystal comprising psilocin and decanoic acid typically further comprises one or more peaks selected from 16.7°, 24.0°, and 24.7°±0.2°2θ. Pattern 1 of the co-crystal comprising psilocin and decanoic acid may further comprise peaks at 16.7°, 24.0° and 24.7°±0.2°2θ.

The XRPD pattern of Pattern 1 of the co-crystal comprising psilocin and decanoic acid may comprise five or more peaks selected from 5.9°, 14.2°, 15.9°, 16.7°, 18.3°, 20.7°, 22.6°, 24.0° and 24.7°±0.2°2θ. The XRPD pattern may comprise seven or more of these peaks. The XRPD pattern may comprise all of these peaks. The XRPD pattern of Pattern 1 of the co-crystal comprising psilocin and decanoic acid may comprise the following peaks.

Pattern 1 of the co-crystal of psilocin and decanoic acid

| Angle. [°2θ] | Rel. Int. [%] |
|---|---|
| 5.9 | 100 |
| 14.2 | 96 |
| 14.4 | 22 |
| 15.9 | 79 |
| 16.7 | 56 |
| 17.7 | 18 |
| 18.3 | 30 |
| 19.0 | 11 |
| 19.3 | 10 |
| 20.1 | 12 |
| 20.7 | 25 |
| 21.0 | 17 |
| 22.1 | 23 |
| 22.6 | 41 |
| 22.9 | 14 |
| 24.0 | 52 |
| 24.6 | 12 |
| 24.7 | 72 |
| 29.9 | 10 |

The XRPD pattern of Pattern 1 of the co-crystal comprising psilocin and decanoic acid may be substantially as shown in FIG. 1.

The co-crystal comprising psilocin and decanoic acid may be in the form of the crystalline form designated as Pattern 2. Pattern 2 of the co-crystal comprising psilocin and decanoic acid typically has an x-ray powder diffraction (XRPD) pattern comprising peaks at 6.4°, 16.9° and 25.2°±0.2°2θ.

The XRPD pattern of Pattern 2 of the co-crystal comprising psilocin and decanoic acid typically further comprises one or more peaks selected from 22.3°, 23.6° and 23.7°±0.2°2θ. Pattern 2 of the co-crystal comprising psilocin and decanoic acid may further comprise peaks at 22.3°, 23.6°, and 23.7°±0.2°2θ.

The XRPD pattern of Pattern 2 of the co-crystal comprising psilocin and decanoic acid may comprise five or more peaks selected from 6.4°, 16.9°, 17.8°, 19.2°, 19.6°, 22.3°, 23.6°, 23.7° and 25.2°±0.2°2θ. The XRPD pattern may comprise seven or more of these peaks. The XRPD pattern may comprise all of these peaks. The XRPD pattern of Pattern 2 of the co-crystal comprising psilocin and decanoic acid may comprise the following peaks.

Pattern 2 of the co-crystal of psilocin and decanoic acid

| Angle [°2θ] | Rel. Int. [%] |
|---|---|
| 6.4 | 100 |
| 16.9 | 43 |
| 17.4 | 11 |
| 17.8 | 14 |
| 19.2 | 17 |
| 19.6 | 16 |
| 20.6 | 12 |
| 22.0 | 14 |
| 22.3 | 18 |
| 22.5 | 13 |
| 23.6 | 28 |
| 23.7 | 23 |
| 24.8 | 12 |
| 25.2 | 33 |
| 25.8 | 13 |
| 26.0 | 12 |

Figure 2:
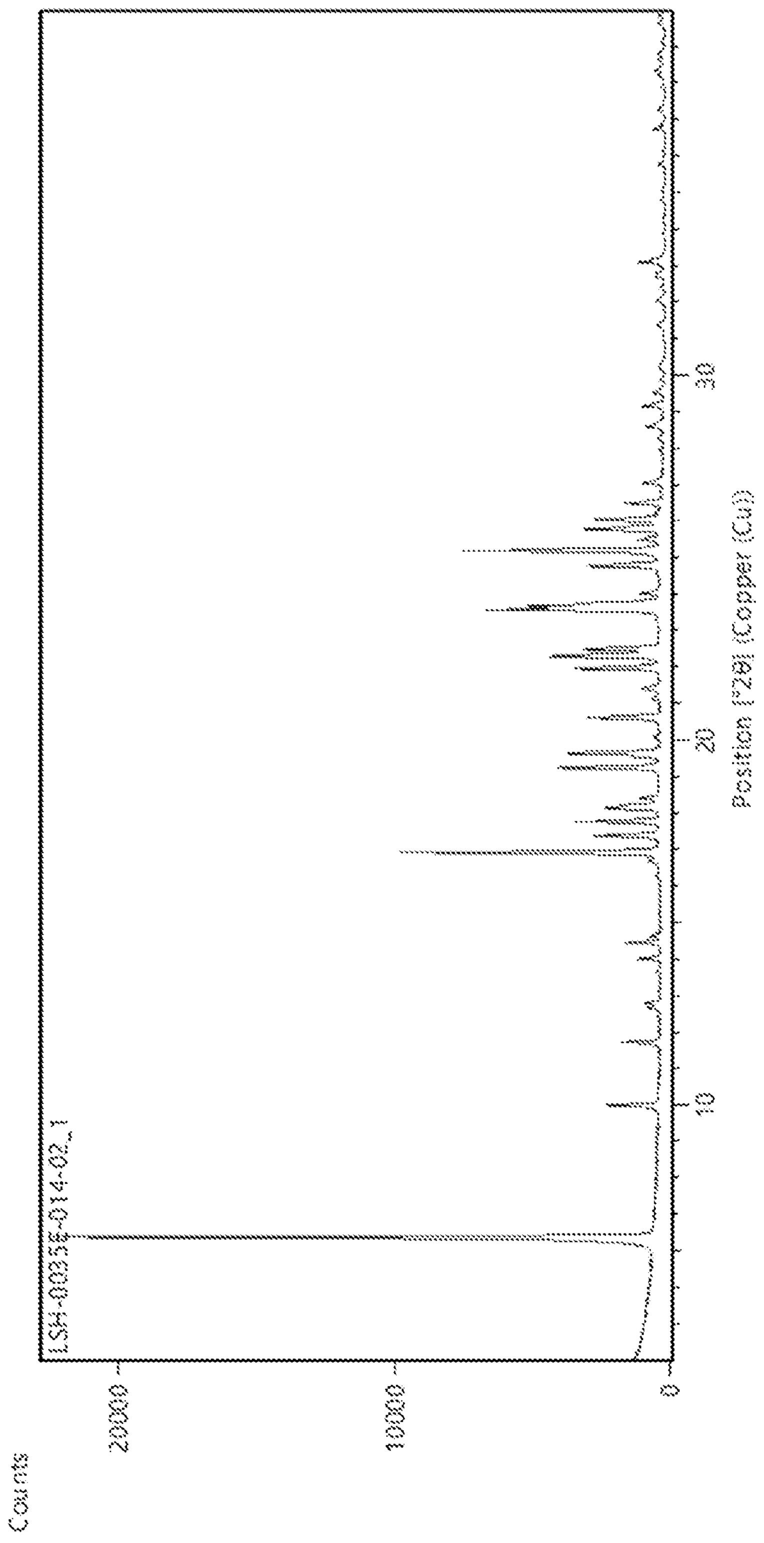
FIG. 2 shows the XRPD 2θ diffractogram of Pattern 2 of a co-crystal comprising psilocin and decanoic acid.

The XRPD pattern of Pattern 2 of the co-crystal comprising psilocin and decanoic acid may be substantially as shown in FIG. 2.

The co-crystal comprising psilocin and ethyl maltol may be in the form of the crystalline form designated as Pattern 1. Pattern 1 of the co-crystal comprising psilocin and ethyl maltol typically has an x-ray powder diffraction (XRPD) pattern comprising peaks at 5.0°, 15.1° and 18.0°±0.2°2θ.

The XRPD pattern of Pattern 1 of the co-crystal comprising psilocin and ethyl maltol typically further comprises one or more peaks selected from 21.7°, 26.1° and 26.7°±0.2°2θ. Pattern 1 of the co-crystal comprising psilocin and ethyl maltol may further comprise peaks at 21.7°, 26.1°, and 26.7°±0.2°2θ.

The XRPD pattern of Pattern 1 of the co-crystal comprising psilocin and ethyl maltol may comprise five or more peaks selected from 5.0°, 14.8°, 15.1°, 18.0°, 18.5°, 20.2°, 21.7°, 26.1° and 26.7°±0.2°2θ. The XRPD pattern may comprise seven or more of these peaks. The XRPD pattern may comprise all of these peaks. The XRPD pattern of Pattern 1 of the co-crystal comprising psilocin and ethyl maltol may comprise the following peaks.

Pattern 1 of the co-crystal of psilocin and ethyl maltol

| Angle [°2θ] | Rel. Int. [%] |
|---|---|
| 5.0 | 100 |
| 9.2 | 21 |
| 9.5 | 24 |
| 13.1 | 13 |
| 13.9 | 12 |
| 14.8 | 25 |
| 15.1 | 73 |
| 15.5 | 13 |
| 16.4 | 16 |
| 18.0 | 63 |
| 18.5 | 33 |
| 20.2 | 25 |
| 21.1 | 22 |
| 21.4 | 22 |
| 21.7 | 36 |
| 22.2 | 17 |
| 22.3 | 12 |
| 26.1 | 52 |
| 26.5 | 10 |
| 26.7 | 38 |
| 27.8 | 16 |

Figure 3:
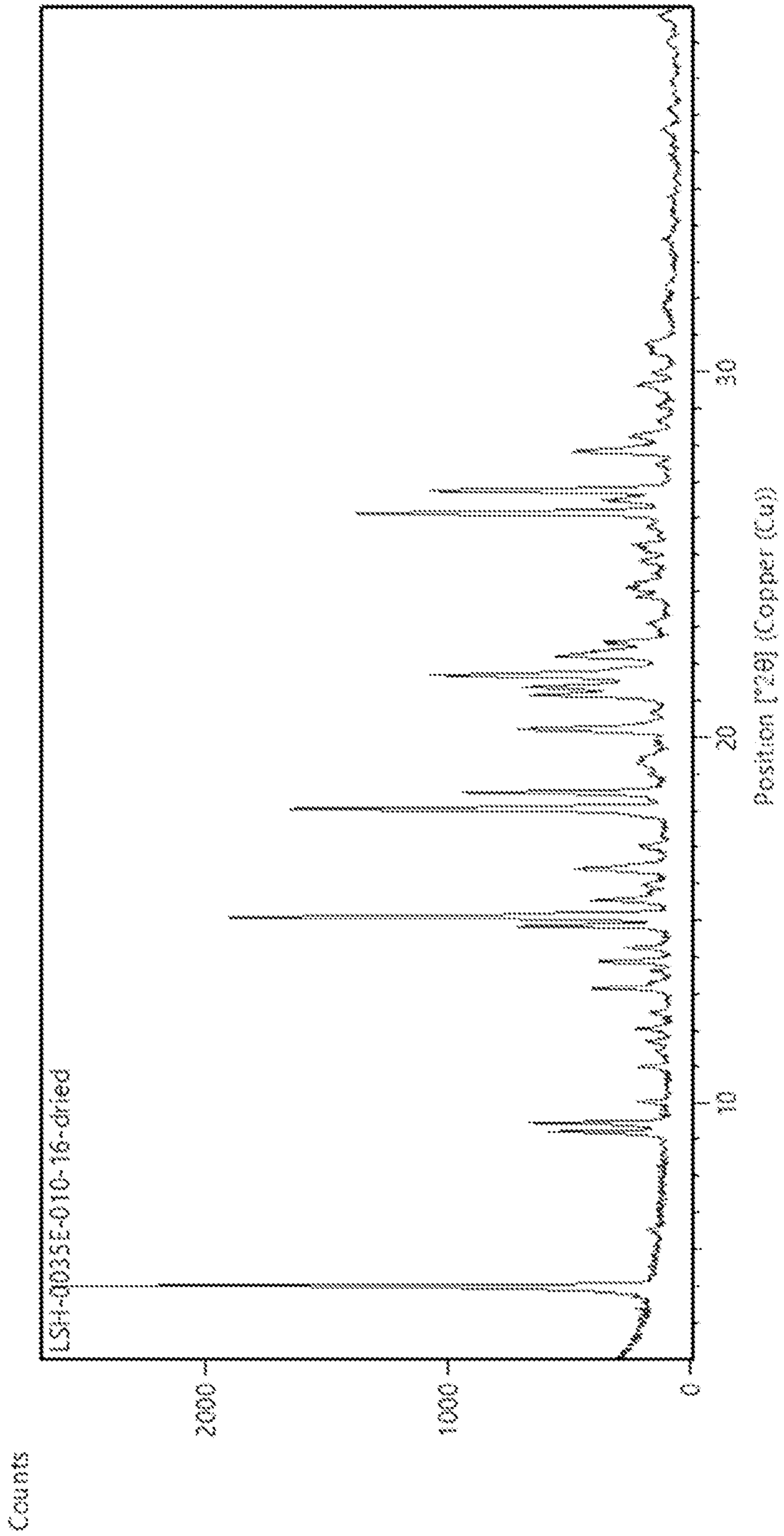
FIG. 3 shows the XRPD 2θ diffractogram of Pattern 1 of a co-crystal comprising psilocin and ethyl maltol.

The XRPD pattern of Pattern 1 of the co-crystal comprising psilocin and ethyl maltol may be substantially as shown in FIG. 3.

The co-crystal comprising psilocin and L-lactic acid may be in the form of the crystalline form designated as Pattern 1. Pattern 1 of the co-crystal comprising psilocin and L-lactic acid typically has an x-ray powder diffraction (XRPD) pattern comprising peaks at 13.4°, 16.8° and 19.5°±0.2°2θ.

The XRPD pattern of Pattern 1 of the co-crystal comprising psilocin and L-lactic acid typically further comprises one or more peaks selected from 16.7°, 23.0° and 24.3°±0.2°2θ. Pattern 1 of the co-crystal comprising psilocin and L-lactic acid may further comprise peaks at 16.7°, 23.0° and 24.3°±0.2°2θ.

The XRPD pattern of Pattern 1 of the co-crystal comprising psilocin and L-lactic acid may comprise five or more peaks selected from 13.4°, 14.9°, 16.7°, 16.8°, 19.5°, 20.6°, 23.0°, 24.3° and 26.3°±0.2°2θ. The XRPD pattern may comprise seven or more of these peaks. The XRPD pattern may comprise all of these peaks. The XRPD pattern of Pattern 1 of the co-crystal comprising psilocin and L-lactic acid may comprise the following peaks.

Pattern 1 of the co-crystal of psilocin and L-lactic acid

| Angle [°2θ] | Rel. Int. [%] |
|---|---|
| 11.0 | 30 |
| 13.4 | 96 |
| 14.2 | 14 |
| 14.9 | 47 |
| 16.7 | 55 |
| 16.8 | 89 |
| 19.5 | 100 |
| 20.1 | 10 |
| 20.3 | 22 |
| 20.6 | 38 |
| 22.2 | 17 |
| 22.5 | 11 |
| 22.8 | 18 |
| 23.0 | 52 |
| 24.3 | 77 |
| 24.4 | 33 |
| 26.3 | 39 |
| 29.1 | 16 |
| 34.0 | 10 |

Figure 4:
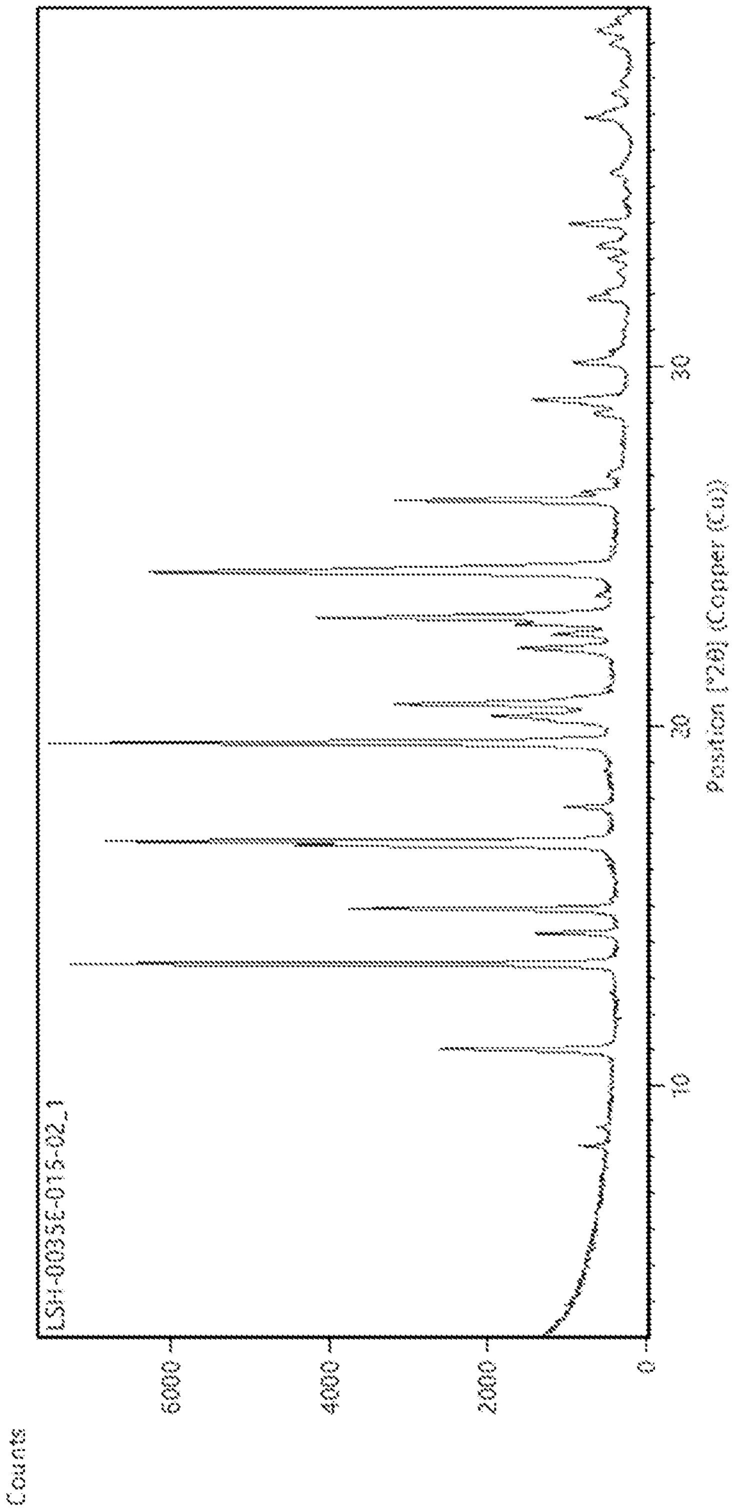
FIG. 4 shows the XRPD 2θ diffractogram of Pattern 1 of a co-crystal comprising psilocin and L-lactic acid.

The XRPD pattern of Pattern 1 of the co-crystal comprising psilocin and L-lactic acid may be substantially as shown in FIG. 4.

The co-crystal comprising psilocin and oleic acid may be in the form of the crystalline form designated as Pattern 1. Pattern 1 of the co-crystal comprising psilocin and oleic acid typically has an x-ray powder diffraction (XRPD) pattern comprising peaks at 4.6°, 15.9° and 19.4°±0.2°2θ.

The XRPD pattern of Pattern 1 of the co-crystal comprising psilocin and oleic acid typically further comprises one or more peaks selected from 19.6°, 20.4° and 23.5°±0.2°2θ. Pattern 1 of the co-crystal comprising psilocin and oleic acid may further comprise peaks at 19.6°, 20.4° and 23.5°±0.2°2θ.

The XRPD pattern of Pattern 1 of the co-crystal comprising psilocin and oleic acid may comprise five or more peaks selected from 4.6°, 15.9°, 19.4°, 19.6°, 20.4°, 21.1°, 21.9°, 22.1° and 23.5°±0.2°2θ. The XRPD pattern may comprise seven or more of these peaks. The XRPD pattern may comprise all of these peaks. The XRPD pattern of Pattern 1 of the co-crystal comprising psilocin and oleic acid may comprise the following peaks.

Pattern 1 of the co-crystal of psilocin and oleic acid

| Angle [°2θ] | Rel. Int. [%] |
|---|---|
| 4.6 | 100 |
| 15.9 | 23 |
| 18.2 | 14 |
| 18.5 | 15 |
| 19.4 | 23 |
| 19.6 | 16 |
| 20.4 | 17 |
| 21.1 | 16 |
| 21.9 | 16 |
| 22.1 | 15 |
| 23.5 | 19 |
| 24.3 | 10 |
| 24.5 | 32 |
| 25.7 | 12 |

Figure 5:
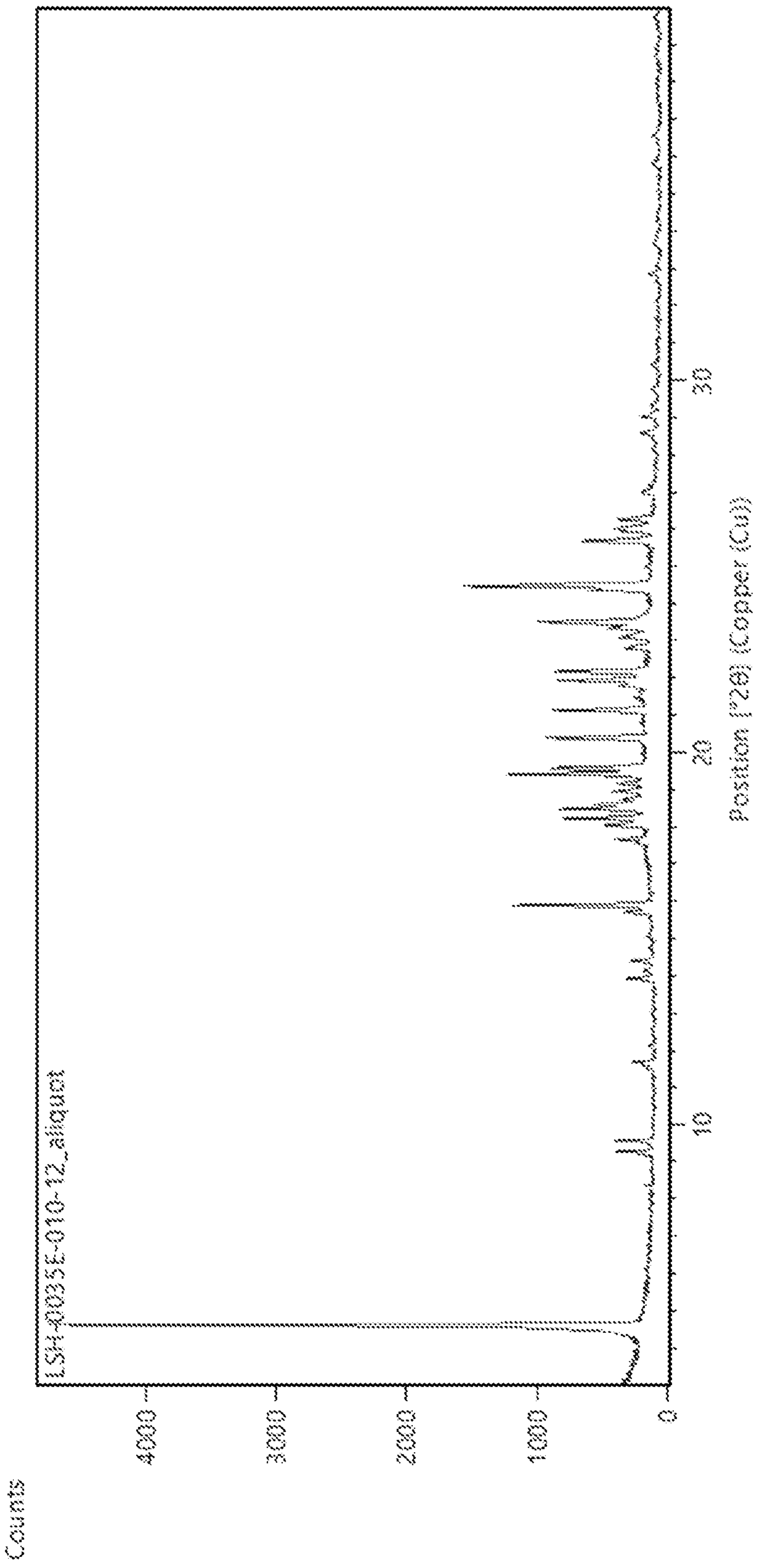
FIG. 5 shows the XRPD 2θ diffractogram of Pattern 1 of a co-crystal comprising psilocin and oleic acid.

The XRPD pattern of Pattern 1 of the co-crystal comprising psilocin and oleic acid may be substantially as shown in FIG. 5.

The co-crystal comprising psilocin and palmitic acid may be in the form of the crystalline form designated as Pattern 1. Pattern 1 of the co-crystal comprising psilocin and palmitic acid typically has an x-ray powder diffraction (XRPD) pattern comprising peaks at 4.7°, 23.0° and 23.8°±0.2°2θ.

The XRPD pattern of Pattern 1 of the co-crystal comprising psilocin and palmitic acid typically further comprises one or more peaks selected from 14.4°, 16.1° and 20.3°±0.2°2θ. Pattern 1 of the co-crystal comprising psilocin and palmitic acid may further comprise peaks at 14.4°, 16.1° and 20.3°±0.2°2θ.

The XRPD pattern of Pattern 1 of the co-crystal comprising psilocin and palmitic acid may comprise five or more peaks selected from 4.7°, 14.4°, 14.7°, 16.1°, 17.0°, 20.3°, 22.9°, 23.0° and 23.8°±0.2°2θ. The XRPD pattern may comprise seven or more of these peaks. The XRPD pattern may comprise all of these peaks. The XRPD pattern of Pattern 1 of the co-crystal comprising psilocin and palmitic acid may comprise the following peaks.

Pattern 1 of the co-crystal of psilocin and palmitic acid

| Angle [°2θ] | Rel. Int. [%] |
|---|---|
| 4.7 | 100 |
| 14.4 | 35 |
| 14.7 | 24 |
| 14.9 | 11 |
| 16.1 | 30 |
| 17.0 | 24 |
| 17.9 | 15 |
| 18.9 | 14 |
| 19.8 | 14 |
| 20.3 | 28 |
| 21.2 | 18 |

-continued

Pattern 1 of the co-crystal of psilocin and palmitic acid

| Angle [°2θ] | Rel. Int. [%] |
|---|---|
| 21.5 | 17 |
| 22.9 | 26 |
| 23.0 | 47 |
| 23.8 | 37 |
| 27.1 | 20 |

Figure 6:
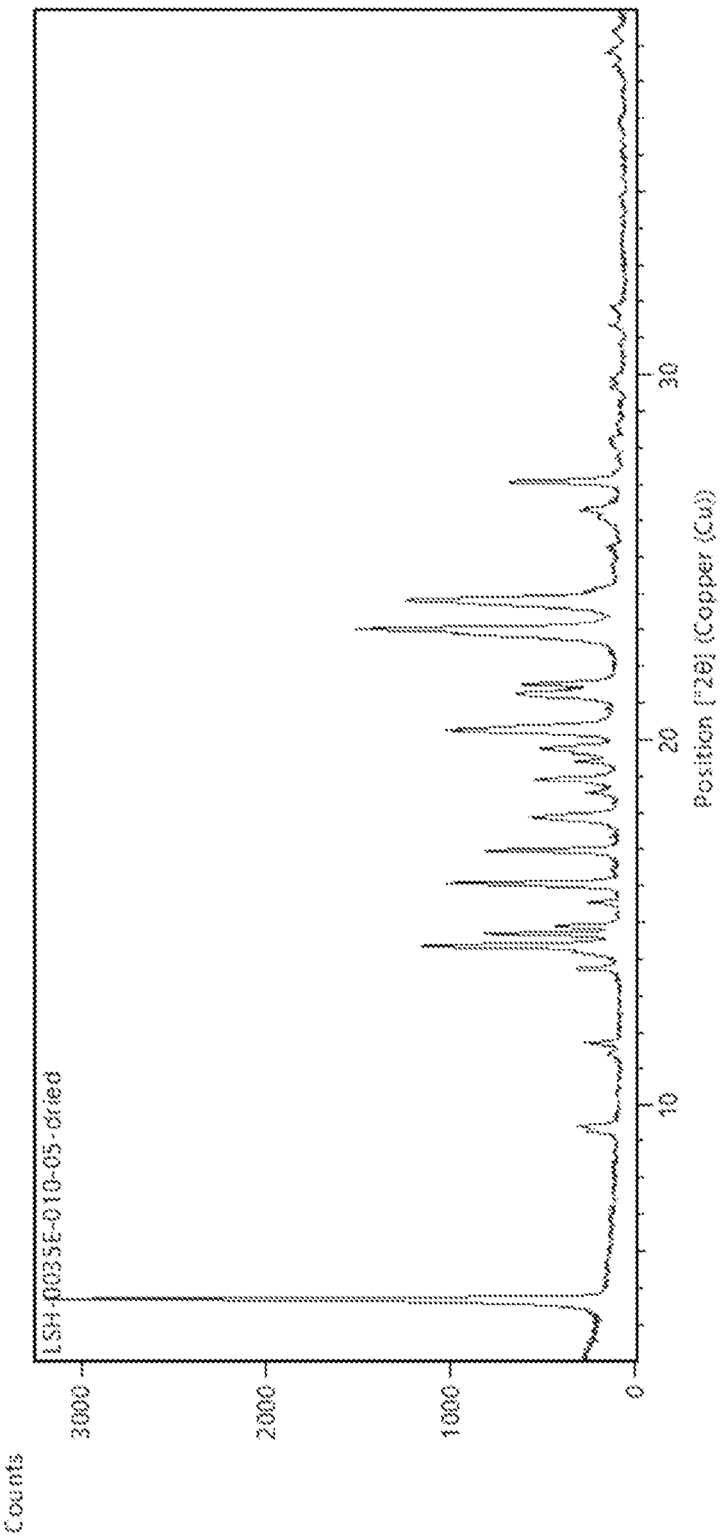
FIG. 6 shows the XRPD 2θ diffractogram of Pattern 1 of a co-crystal comprising psilocin and palmitic acid.

The XRPD pattern of Pattern 1 of the co-crystal comprising psilocin and palmitic acid may be substantially as shown in FIG. 6.

The co-crystal comprising psilocin and p-coumaric acid may be in the form of the crystalline form designated as Pattern 1. Pattern 1 of the co-crystal comprising psilocin and p-coumaric acid typically has an x-ray powder diffraction (XRPD) pattern comprising peaks at 5.4°, 15.5° and 20.5°±0.2°2θ.

The XRPD pattern of Pattern 1 of the co-crystal comprising psilocin and p-coumaric acid typically further comprises one or more peaks selected from 6.5°, 16.4° and 19.7°±0.2°2θ. Pattern 1 of the co-crystal comprising psilocin and p-coumaric acid may further comprise peaks at 6.5°, 16.4° and 19.7°±0.2°2θ.

The XRPD pattern of Pattern 1 of the co-crystal comprising psilocin and p-coumaric acid may comprise five or more peaks selected from 5.4°, 6.5°, 7.0°, 15.5°, 16.4°, 17.3°, 19.7°, 20.5° and 21.9°±0.2°2θ. The XRPD pattern may comprise seven or more of these peaks. The XRPD pattern may comprise all of these peaks. The XRPD pattern of Pattern 1 of the co-crystal comprising psilocin and p-coumaric acid may comprise the following peaks.

Pattern 1 of the co-crystal comprising psilocin and p-coumaric acid

| Angle [°2θ] | Rel. Int. [%] |
|---|---|
| 5.4 | 100 |
| 6.5 | 17 |
| 7.0 | 12 |
| 15.0 | 8 |
| 15.5 | 35 |
| 16.4 | 22 |
| 17.0 | 8 |
| 17.3 | 12 |
| 17.9 | 9 |
| 18.2 | 9 |
| 18.4 | 8 |
| 19.3 | 9 |
| 19.7 | 21 |
| 20.5 | 29 |
| 21.9 | 12 |
| 22.8 | 11 |
| 23.7 | 9 |

Figure 7:
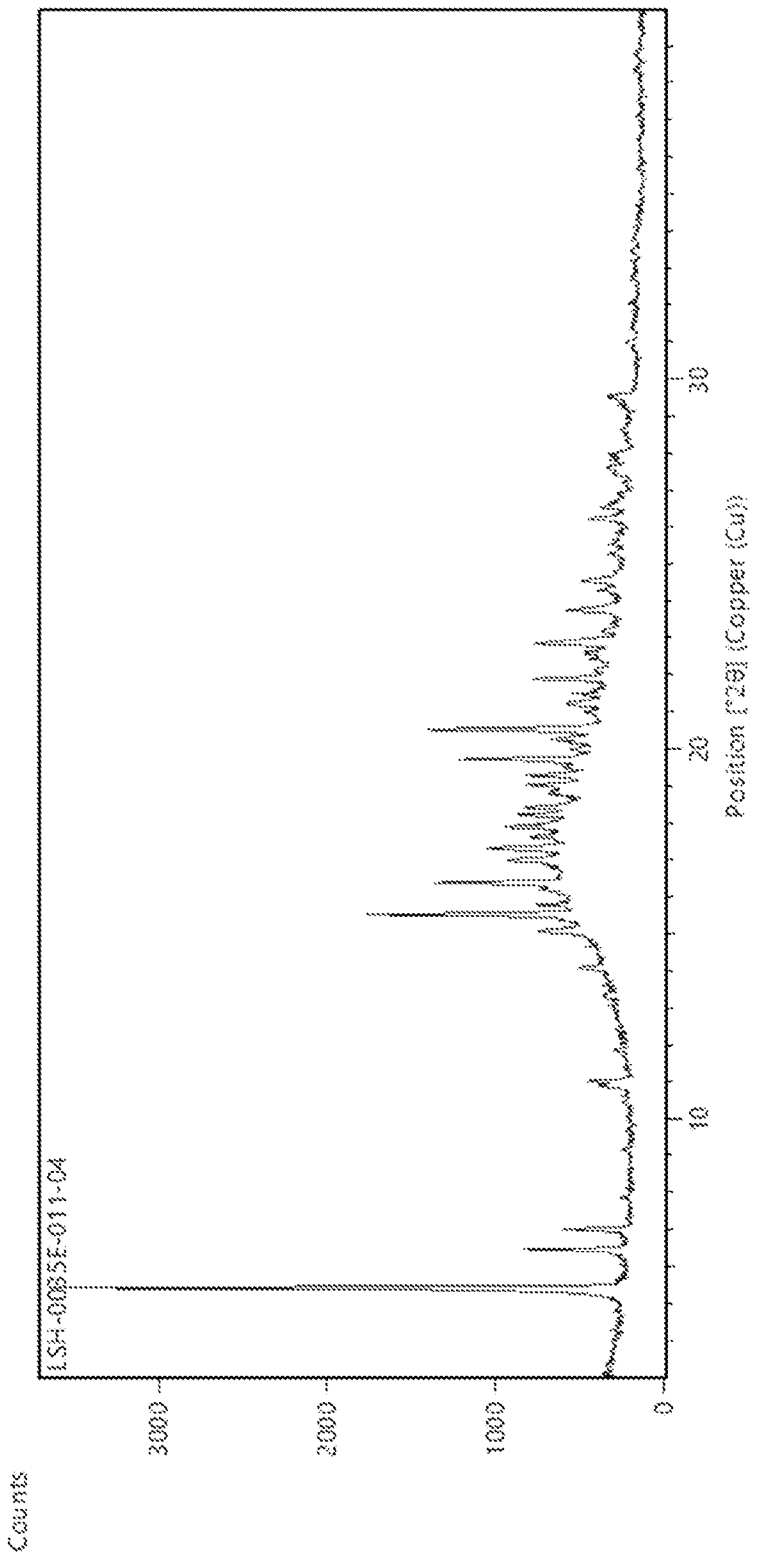
FIG. 7 shows the XRPD 2θ diffractogram of Pattern 1 of a co-crystal comprising psilocin and p-coumaric acid.

The XRPD pattern of Pattern 1 of the co-crystal comprising psilocin and p-coumaric acid may be substantially as shown in FIG. 7.

The co-crystal comprising psilocin and propyl gallate may be in the form of the crystalline form designated as Pattern 1. Pattern 1 of the co-crystal comprising psilocin and propyl gallate typically has an x-ray powder diffraction (XRPD) pattern comprising peaks at 12.6°, 14.7° and 22.6°±0.2°2θ.

The XRPD pattern of Pattern 1 of the co-crystal comprising psilocin and propyl gallate typically further comprises one or more peaks selected from 8.8°, 15.8° and 18.6°±0.2°2θ. Pattern 1 of the co-crystal comprising psilocin and propyl gallate may further comprise peaks at 8.8°, 15.8° and 18.6°±0.2°2θ.

The XRPD pattern of Pattern 1 of the co-crystal comprising psilocin and propyl gallate may comprise five or more peaks selected from 8.8°, 12.6°, 14.3°, 14.7°, 15.8°, 18.6°, 19.2°, 22.0° and 22.6°±0.2°2θ. The XRPD pattern may comprise seven or more of these peaks. The XRPD pattern may comprise all of these peaks. The XRPD pattern of Pattern 1 of the co-crystal comprising psilocin and propyl gallate may comprise the following peaks.

| Pattern 1 of the co-crystal of psilocin and propyl gallate | |
|---|---|
| Angle [°2θ] | Rel. Int. [%] |
| 8.8 | 61 |
| 11.4 | 33 |
| 11.8 | 21 |
| 12.6 | 100 |
| 13.2 | 29 |
| 14.3 | 36 |
| 14.7 | 74 |
| 15.8 | 64 |
| 18.6 | 69 |
| 18.7 | 21 |
| 19.2 | 59 |
| 19.8 | 34 |
| 22.0 | 40 |
| 22.4 | 22 |
| 22.6 | 72 |
| 22.9 | 21 |
| 23.0 | 26 |
| 24.0 | 33 |
| 24.3 | 22 |
| 26.9 | 33 |

Figure 8:
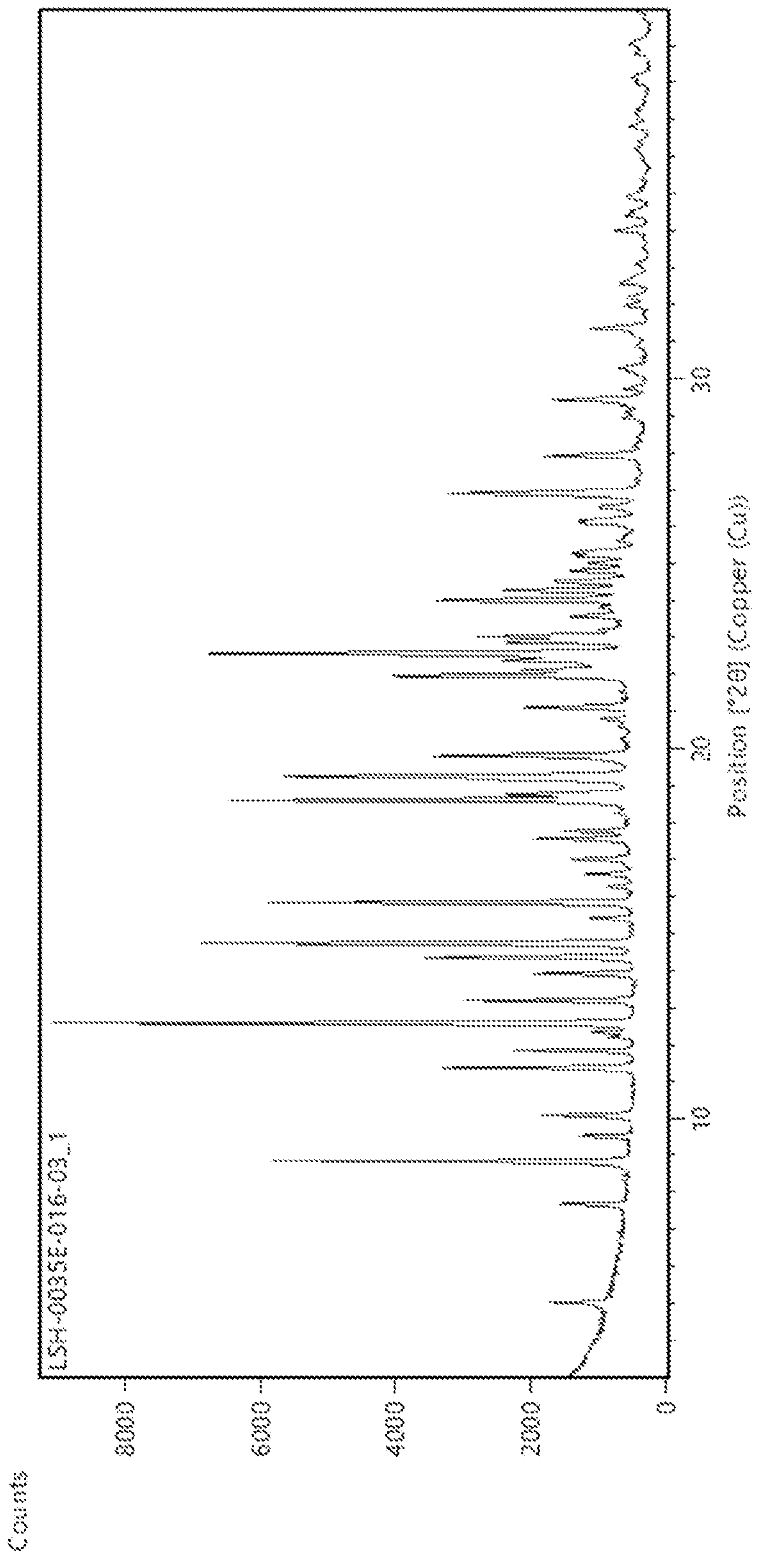
FIG. 8 shows the XRPD 2θ diffractogram of Pattern 1 of a co-crystal comprising psilocin and propyl gallate.

The XRPD pattern of Pattern 1 of the co-crystal comprising psilocin and propyl gallate may be substantially as shown in FIG. 8.

The co-crystal comprising psilocin and stearic acid may be in the form of the crystalline form designated as Pattern 1. Pattern 1 of the co-crystal comprising psilocin and stearic acid typically has an x-ray powder diffraction (XRPD) pattern comprising peaks at 21.4°, 21.6° and 23.5°±0.2°2θ.

The XRPD pattern of Pattern 1 of the co-crystal comprising psilocin and stearic acid typically further comprises one or more peaks selected from 5.4°, 16.0° and 18.8°±0.2°2θ. Pattern 1 of the co-crystal comprising psilocin and stearic acid may further comprise peaks at 5.4°, 16.0° and 18.8°±0.2°2θ.

The XRPD pattern of Pattern 1 of the co-crystal comprising psilocin and stearic acid may comprise five or more peaks selected from 5.4°, 16.0°, 16.8°, 18.3°, 18.8°, 21.4°, 21.6°, 23.5° and 23.7°±0.2°2θ. The XRPD pattern may comprise seven or more of these peaks. The XRPD pattern may comprise all of these peaks. The XRPD pattern of Pattern 1 of the co-crystal comprising psilocin and stearic acid may comprise the following peaks.

| Pattern 1 of the co-crystal of psilocin and stearic acid | |
|---|---|
| Angle [°2θ] | Rel. Int. [%] |
| 5.4 | 21 |
| 13.4 | 10 |
| 16.0 | 18 |
| 16.8 | 14 |
| 18.0 | 12 |
| 18.3 | 16 |
| 18.8 | 19 |
| 19.6 | 11 |
| 21.4 | 100 |
| 21.6 | 51 |

-continued

| Pattern 1 of the co-crystal of psilocin and stearic acid | |
|---|---|
| Angle [°2θ] | Rel. Int. [%] |
| 22.9 | 10 |
| 23.5 | 42 |
| 23.7 | 17 |
| 24.0 | 13 |

Figure 9:
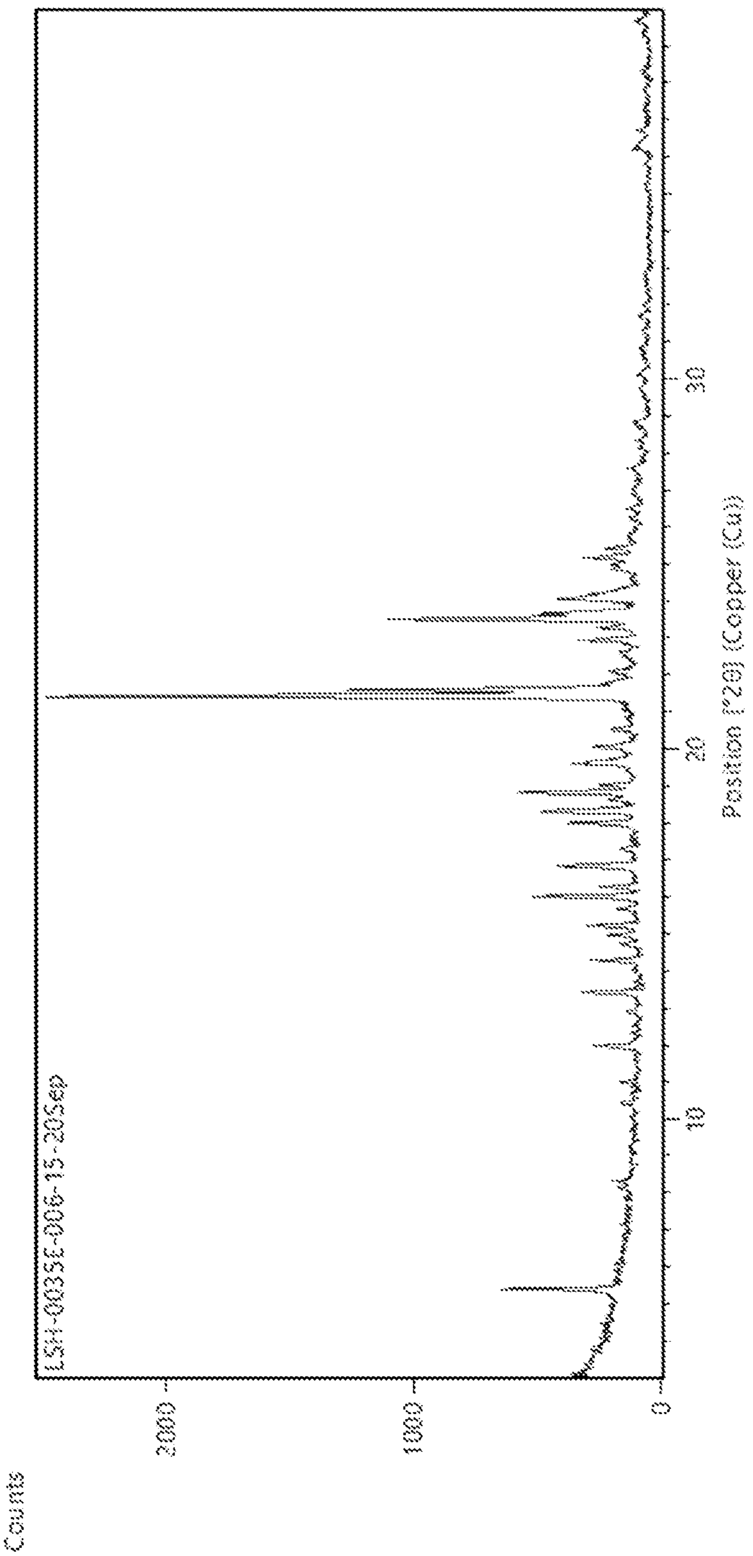
FIG. 9 shows the XRPD 2θ diffractogram of Pattern 1 of a co-crystal comprising psilocin and stearic acid.

The XRPD pattern of Pattern 1 of the co-crystal comprising psilocin and stearic acid may be substantially as shown in FIG. 9.

The co-crystal comprising psilocin and stearic acid may be in the form of the crystalline form designated as Pattern 2. Pattern 2 of the co-crystal comprising psilocin and stearic acid typically has an x-ray powder diffraction (XRPD) pattern comprising peaks at 4.5°, 14.3° and 24.0°±0.2°2θ.

The XRPD pattern of Pattern 2 of the co-crystal comprising psilocin and stearic acid typically further comprises one or more peaks selected from 16.7°, 20.0° and 23.3°±0.2°2θ. Pattern 2 of the co-crystal comprising psilocin and stearic acid may further comprise peaks at 16.7°, 20.0° and 23.3°±0.2°2θ.

The XRPD pattern of Pattern 2 of the co-crystal comprising psilocin and stearic acid may comprise five or more peaks selected from 4.5°, 14.3°, 16.3°, 16.7°, 20.0°, 20.1°, 20.8°, 23.3° and 24.0°±0.2°2θ. The XRPD pattern may comprise seven or more of these peaks. The XRPD pattern may comprise all of these peaks. The XRPD pattern of Pattern 2 of the co-crystal comprising psilocin and stearic acid may comprise the following peaks.

| Pattern 2 of the co-crystal of psilocin and stearic acid | |
|---|---|
| Angle [°2θ] | Rel. Int. [%] |
| 4.5 | 100 |
| 8.9 | 14 |
| 13.6 | 14 |
| 14.3 | 43 |
| 15.6 | 16 |
| 16.3 | 30 |
| 16.7 | 33 |
| 18.0 | 13 |
| 18.7 | 15 |
| 19.2 | 10 |
| 20.0 | 37 |
| 20.1 | 30 |
| 20.8 | 30 |
| 22.6 | 29 |
| 23.3 | 40 |
| 24.0 | 64 |
| 26.4 | 28 |

Figure 10:
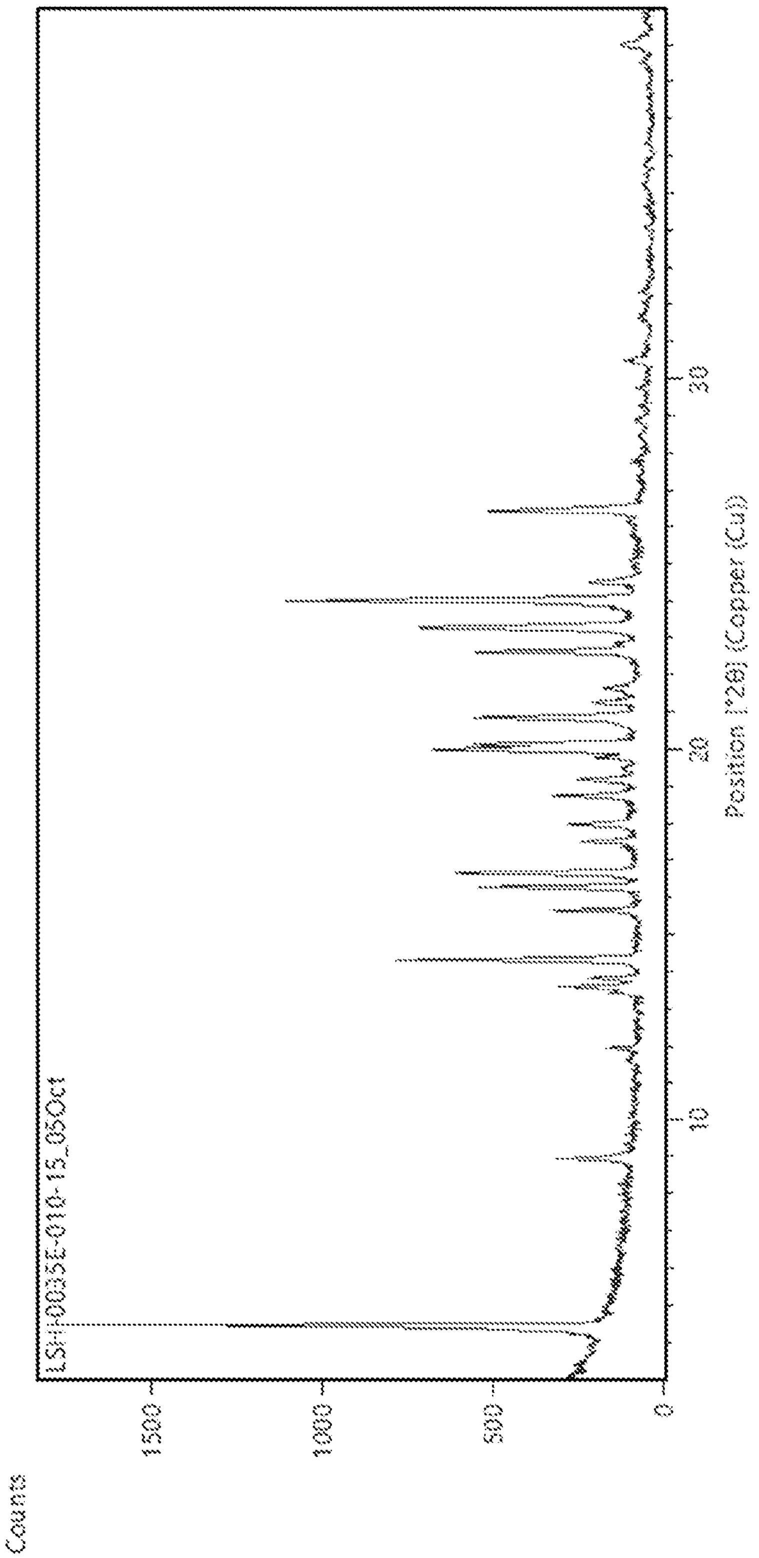
FIG. 10 shows the XRPD 2θ diffractogram of Pattern 2 of a co-crystal comprising psilocin and stearic acid.

The XRPD pattern of Pattern 2 of the co-crystal comprising psilocin and stearic acid may be substantially as shown in FIG. 10.

The invention also provides a composition comprising the co-crystal, where at least 50 wt %, at least 80 wt % or at least 90 wt % of the co-crystal is in the form of a crystalline form of that co-crystal defined herein.

Co-Crystals with Acid

Also disclosed herein is a co-crystal comprising psilocin and a co-former, wherein the co-former is an acid. An acid may be any substance which can act as a proton donor. Alternatively, an acid may be any substance which can act as an electron pair acceptor. Alternatively, an acid may be any substance which increases the concentration of $H_3O^+$ ions in an aqueous solution.

The co-former may be an organic acid or an inorganic acid. Typically, the co-former is an organic acid.

Typically, the co-former is a compound which comprises one or more acidic functional groups. The acidic functional group may be selected from, for example, a carboxylic acid moiety, a sulfonic acid moiety, a squaric acid moiety, a sulphonamide moiety, a carboxylic sulfonimide moiety, and a sulfimide moiety. Thus, the co-former may be a compound which comprises one or more of a carboxylic acid moiety, a sulfonic acid moiety, a squaric acid moiety, a sulphonamide moiety, a carboxylic sulfonimide moiety, and a sulfimide moiety. Typically, the co-former is a compound which comprises a carboxylic acid moiety. The co-former may be a compound which comprises a sulfonic acid moiety. The co-former may be a compound which comprises a squaric acid moiety. The co-former may be a compound which comprises a sulphonamide moiety. The co-former may be a compound which comprises a carboxylic sulfonimide moiety. The co-former may be a compound which comprises a sulfimide moiety.

A strongly acidic co-former may protonate the tertiary amine group in psilocin, and thus form a simple salt with psilocin. Typically, a co-crystal will form where the $pK_a$ of the acid is not sufficiently low enough to facilitate complete transfer a proton to the tertiary amine group in psilocin. Therefore, the co-former typically has a $pK_a$ of greater than or equal to 1.3, for example greater than or equal to 1.5, 1.75, 2.0, 2.25, 2.5, 2.75, 3.0, 3.5, 4.0, or 4.5. Typically, the co-former typically has a $pK_a$ of greater than or equal to 1.5, 2.0, or 2.5. The co-former may have a $pK_a$ of greater than or equal to 1.5. The co-former may have a $pK_a$ of greater than or equal to 2.0. The co-former may have a $pK_a$ of greater than or equal to 2.5.

The co-former may have a $pK_a$ of less than or equal to 7.0, for example less than or equal to 6.5, 6.0, 5.5, or 5.0. Typically, the co-former has a $pK_a$ of less than or equal to 7.0, 6.0 or 5.0. The co-former may have a $pK_a$ of less than or equal to 7.0. The co-former may have a $pK_a$ of less than or equal to 6.0. The co-former may have a $pK_a$ of less than or equal to 5.0.

The co-former may have a $pK_a$ of from 1.5 to 7.0. For example, the co-former may have a $pK_a$ of from 1.5 to 6.0, or from 1.5 to 5.0, or from 1.5 to 4.5, or from 1.5 to 4.0. The co-former may have a $pK_a$ of from 2.0 to 6.0, or from 2.0 to 5.0, or from 2.0 to 4.5, or from 2.0 to 4.0. The co-former may have a $pK_a$ of from 2.5 to 6.0, or from 2.5 to 5.0, or from 2.5 to 4.5, or from 2.5 to 4.0. Typically, the co-former has a $pK_a$ of from 1.5 to 5.0.

The co-former may be selected from: sulfurous acid, sulfuric acid, sulfoxylic acid, persulfuric acid, disulfuric acid, disulfurous acid, dithionous acid, tetrathionic acid, hydrosulfuric acid, peroxydisulfuric acid, perchloric acid, hydrochloric acid, hypochlorous acid, chlorous acid, chloric acid, hyponitrous acid, nitrous acid, nitric acid, pernitric acid, formic acid, 2-hydroxyethanoic acid, oxoacetic acid, carbonic acid, oxalic acid, acetic acid, fluoroacetic acid, trifluoroacetic acid, chloroacetic acid, dichloroacetic acid, trichloroacetic acid, phosphoric acid, phosphinic acid, perphosphoric acid, hypophosphoric acid, diphosphoric acid, hydrobromic acid, bromous acid, bromic acid, hypobromous acid, perbromic acid, hypoiodous acid, iodous acid, iodic acid, periodic acid, hydroiodic acid, hypofluorous acid, hydrofluoric acid, methanesulfonic acid, ethanesulfonic acid, benzenesulfonic acid, squaric acid, chromic acid, selenic acid, selenous acid, boric acid, telluric acid, citric acid, pyrocitric acid, isocitric acid, sorbic acid, permanganic acid, silicic acid, dichromic acid, cyanic acid, malonic acid, tartronic acid, glycidic acid, tartaric acid (including L-tartaric acid, D-tartaric acid, or a mixture thereof), phthalic acid, barbituric acid, benzilic acid, cinnamic acid, fumaric acid, glutaric acid, gluconic acid, hexanoic acid, heptanoic acid, lactic acid (including L-lactic acid, D-lactic acid, or a mixture thereof), malic acid (including L-malic acid, D-malic acid, or a mixture thereof), oleic acid, linoleic acid, folic acid, propiolic acid, propanoic acid, 2-hydroxypropanoic acid, 3-hydroxypropanoic acid, 2,3-dihydroxypropanoic acid, propenoic acid, pyruvic acid, butyric acid, isobutyric acid, tetrolic acid, valeric acid, pivalic acid, caproic acid, capric acid, fulvic acid, mellitic acid, palmitic acid, adipic acid, phthalic acid, stearic acid, ascorbic acid (including L-ascorbic acid, D-ascorbic acid, or a mixture thereof), gallic acid, N-acetyl glycine, alginic acid, tannic acid, benzoic acid, salicylic acid, 2-(4-hydroxybenzoyl) benzoic acid, 2-(3-hydroxybenzoyl)benzoic acid, 2-(2-hydroxybenzoyl)benzoic acid, 3-(2-hydroxybenzoyl)benzoic acid, 3-(3-hydroxybenzoyl)benzoic acid, 3-(4-hydroxybenzoyl)benzoic acid 4-(2-hydroxybenzoyl)benzoic acid, 4-(3-hydroxybenzoyl)benzoic acid, 4-(4-hydroxybenzoyl)benzoic acid, glucoheptonic acid, 1-naphthoic acid, 2-naphthoic acid, 1-hydroxy-2-naphthoic acid, 3-hydroxy-2-naphthoic acid, 2-hydroxy-1-naphthoic acid, 3-hydroxy-1-naphthoic acid, orotic acid, acetoacetic acid, succinic acid, ketosuccinic acid, methylmalonic acid, ferulic acid, fumaric acid, gentisic acid, p-coumaric acid, m-coumaric acid, o-coumaric acid, disodium EDTA, EDTA, nicotinic acid, glutaric acid, 2-ketoglutaric acid, 3-ketoglutaric acid, 2-furoic acid, tetrahydrofuroic acid, 4-hydroxyphenyl acetic acid, 3-hydroxyphenyl acetic acid, 2-hydroxyphenyl acetic acid, maleic acid, oxalic acid, saccharin, phosphonic acid, ethyl phosphonic acid, propyl phosphonic acid, hippuric acid, sebacic acid, camphoric acid, aconitic acid, and thiodipropionic acid.

The co-former may be selected from: N-acetyl glycine, alginic acid, 2-(4-hydroxybenzoyl)benzoic acid, gluconic acid, glucoheptonic acid, 2-naphthoic acid, orotic acid, succinic acid, L-ascorbic acid, L-tartaric acid, cinnamic acid, ferulic acid, fumaric acid, gentisic acid, gallic acid, citric acid, p-coumaric acid, L-lactic acid, disodium EDTA, nicotinic acid, 1-hydroxy-2-naphthoic acid, 2-ketoglutaric acid, 4-hydroxyphenyl acetic acid, L-malic acid, maleic acid, oxalic acid and saccharin.

Typically, the co-former is selected from citric acid, succinic acid, fumaric acid, gluconic acid, L-tartaric acid, L-ascorbic acid, L-lactic acid, saccharin, disodium EDTA and nicotinic acid.

The co-crystal may comprise psilocin and a co-former which is N-acetyl glycine. The co-crystal may comprise psilocin and a co-former which is alginic acid. The co-crystal may comprise psilocin and a co-former which is 2-(4-hydroxybenzoyl)benzoic acid. The co-crystal may comprise psilocin and a co-former which is gluconic acid. The co-crystal may comprise psilocin and a co-former which is glucoheptonic acid. The co-crystal may comprise psilocin and a co-former which is 2-naphthoic acid. The co-crystal may comprise psilocin and a co-former which is orotic acid. The co-crystal may comprise psilocin and a co-former which is succinic acid. The co-crystal may comprise psilocin and a co-former which is L-ascorbic acid. The co-crystal may comprise psilocin and a co-former which is L-tartaric acid. The co-crystal may comprise psilocin and a co-former which is cinnamic acid. The co-crystal may comprise psilocin and a co-former which is ferulic acid. The co-crystal may comprise psilocin and a co-former which is fumaric acid. The co-crystal may comprise psilocin and a co-former which is gentisic acid. The co-crystal may comprise psilocin and a co-former which is gallic acid. The co-crystal may comprise psilocin and a co-former which is citric acid. The co-crystal may comprise psilocin and a co-former which is p-coumaric acid. The co-crystal may comprise psilocin and a co-former which is L-lactic acid. The co-crystal may comprise psilocin and a co-former which is disodium EDTA. The co-crystal may comprise psilocin and a co-former which is nicotinic acid.

The co-crystal may comprise psilocin and a co-former which is 1-hydroxy naphthoic acid. The co-crystal may comprise psilocin and a co-former which is 2-ketoglutaric acid. The co-crystal may comprise psilocin and a co-former which is 4-hydroxyphenyl acetic acid. The co-crystal may comprise psilocin and a co-former which is L-malic acid. The co-crystal may comprise psilocin and a co-former which is maleic acid. The co-crystal may comprise psilocin and a co-former which is oxalic acid. The co-crystal may comprise psilocin and a co-former which is saccharin.

Co-Crystals with a Base

Also disclosed herein is a co-crystal comprising psilocin and a co-former, wherein the co-former is a base. A base may be any substance which can act as a proton acceptor. Alternatively, a base may be any substance which can act as an electron pair donor. Alternatively, a base may be any substance which increases the concentration of $OH^-$ ions in an aqueous solution.

The co-former may be an organic base or an inorganic base. Typically, the co-former is an organic base.

Typically, the co-former is a compound which comprises one or more basic functional groups. The basic functional group may be selected from, for example, an amine moiety, a pyridine moiety, a piperazine moiety, an amide moiety, a xanthine moiety and a morpholine moiety. Thus, the co-former may be a compound which comprises one or more of an amine moiety, a pyridine moiety, a piperazine moiety, an amide moiety, a xanthine moiety and a morpholine moiety. Typically, the co-former is a compound which comprises an amine moiety. The co-former may be a compound which comprises a pyridine moiety. The co-former may be a compound which comprises a piperazine moiety. The co-former may be a compound which comprises an amide moiety. The co-former may be a compound which comprises a xanthine moiety. The co-former may be a compound which comprises a morpholine moiety.

A co-former which is a strong base may deprotonate the hydroxyl group in psilocin, and thus form a simple salt with psilocin. Typically, a co-crystal will form where the $pK_b$ of the base is not sufficiently low enough to facilitate complete transfer of a proton from the hydroxyl residue in psilocin.

Therefore, the co-former typically has a $pK_b$ of greater than or equal to 3.5, for example greater than or equal to 4.0, 4.5, 5.0, 5.5, 6.0, 6.5, 7.0 or 7.5. Typically, the co-former typically has a $pK_b$ of greater than or equal to 3.5, 4.5, or 5.5. The co-former may have a $pK_b$ of greater than or equal to 3.5. The co-former may have a $pK_b$ of greater than or equal to 4.5. The co-former may have a $pK_b$ of greater than or equal to 5.5.

The co-former may have a $pK_b$ of less than or equal to 11.0, for example less than or equal to 10.5, 10.0, 9.5, 9.0, 8.5, or 8.0. Typically, the co-former has a $pK_b$ of less than or equal to 11.0, 10.0 or 9.0. The co-former may have a $pK_b$ of less than or equal to 11.0. The co-former may have a $pK_b$ of less than or equal to 10.0. The co-former may have a $pK_b$ of less than or equal to 9.0.

The co-former may have a $pK_b$ of from 3.5 to 11.0. For example, the co-former may have a $pK_b$ of from 3.5 to 10.5, or from 3.5 to 10.0, or from 3.5 to 9.5, or from 3.5 to 9.0. The co-former may have a $pK_b$ of from 4.5 to 11.0, or from 4.5 to 10.5, or from 4.5 to 10.0, or from 4.5 to 9.5, or from 4.5 to 9.0. The co-former may have a $pK_b$ of from 5.5 to 11.0, or from 5.5 to 10.5, or from 5.5 to 10.0, or from 5.5 to 9.5, or from 5.5 to 9.0. Typically, the co-former has a $pK_b$ of from 5.5 to 11.0.

The co-former may be selected from: 1-aminopentane, 3-aminopentane, N-butylamine, sec-butylamine, tert-butylamine, propylhexedrine, cyclopentamine, cypenamine, cyclopentamine, dibutylamine, diethylamine, diisopropylamine, N,N-diisopropylethylamine, dimethylamine, 1,3-dimethylbutylamine, N,N-dimethylethylamine, dipropylamine, ethylamine, ethylmethylamine, hexylamine, isobutylamine, isopropylamine, methylamine, methylhexanamine, N,N-diethylmethylamine, octodrine, tert-octylamine, propylamine, tributylamine, triethylamine, triisopropylamine, trimethylamine, trioctylamine, 2-aminoheptane, tromethamine, 1,2-diaminocyclohexane, trans-1,2-diaminocyclohexane, 4,4-diaminodicyclohexylmethane, diaminomaleonitrile, 1,8-diaminonaphthalene, 1,5-diaminonaphthalene, diaminopropane, 1,2-diaminopropane, 1,3-diaminopropane, 2,4-diaminotoluene, 2,5-diaminotoluene, 1,4-diazacycloheptane, 1,5-diazacyclooctane, diazinane, N,N-dimethyl-1,3-propanediamine, dimethyl phenylenediamine, dimethylaminopropylamine, dimethylethylenediamine, 1,1-dimethylethylenediamine, 1,2-dimethylethylenediamine, diphenylethylenediamine, ethylenediamine, diethanolamine, N,N-diethylethanolamine, N,N-dimethylethanolamine (deanol), N,N-diisopropylaminoethanol, ethanolamine, methanolamine, pyridine, 1-methylpyridine, 2-methylpyridine, 3-methylpyridine, 4-methylpyridine, 2,4-dimethylpyridine, 2,6-dimethylpyridine, 1-ethylpyridine, 2-ethylpyridine, 3-ethylpyridine, 4-ethylpyridine, 2,4-diethylpyridine, 2,6-diethylpyridine, 2,2-bipyridine, 2,3-bipyridine, 2,4-bipyridine, 3,3-bipyridine, 3,4-bipyridine, 4,4-bipyridine, pyridoxine, pyridoxal, pyridoxamine, piperazine, 1-benzylpiperazine, 1-methyl-4-benzylpiperazine, 1,4-dibenzylpiperazine, 3,4-methylenedioxy-1-benzylpiperazine, methoxypiperamide, 1-phenylpiperazine, 2-methylphenylpiperazine, 2-methoxyphenylpiperazine, 3-methylphenylpiperazine, 3-methoxyphenylpiperazine, 4-methylphenylpiperazine, 4-methoxyphenylpiperazine, 2,3-methylphenylpiperazine, acetamide, benzamide, N-methylbenzamide, 4-methylbenzamide, 3-methylbenzamide, dimethylformamide, dimethylacetamide, diethylacetamide, butanamide, N-methylbutanamide, formamide, N-methylformamide, propanamide, 2-methylpropanamide, N-methylpropanamide, nicotinamide, isonicotinamide, morpholine, N-methylmorpholine, 2-methylmorpholine, 3-methylmorpholine, N-ethylmorpholine, 2-ethylmorpholine, 3-ethylmorpholine, N-propylmorpholine, 2-propylmorpholine, 3-propylmorpholine, N-methylmorpholine N-oxide, 4-(2-hydroxyethyl)-morpholine, 4-(1-hydroxyethyl)-morpholine, 4-(3-hydroxypropyl)-morpholine, 4-(2-hydroxypropyl)-morpholine, 1,3-dimethylxanthine (theophylline), 1-methylxanthine, 3-methylxanthine, 1,3-diethylxanthine, 1-ethylxanthine, 2-ethylxanthine, xanthine, indole, purine, isoindole, carbazole, quinoline, and isoquinoline.

The co-former may be selected from: 4,4-bipyridine, pyridoxine, deanol, 4-(2-hydroxyethyl)-morpholine, piperazine, theophylline, nicotinamide, isonicotinamide, tromethamine, tert-butyl amine and diethylamine.

Typically, the co-former is selected from theophylline, nicotinamide, isonicotinamide, and tromethamine.

The co-crystal may comprise psilocin and a co-former which is 4,4-bipyridine. The co-crystal may comprise psilocin and a co-former which is pyridoxine. The co-crystal may comprise psilocin and a co-former which is deanol. The co-crystal may comprise psilocin and a co-former which is 4-(2-hydroxyethyl)-morpholine. The co-crystal may comprise psilocin and a co-former which is piperazine. The co-crystal may comprise psilocin and a co-former which is theophylline. The co-crystal may comprise psilocin and a co-former which is nicotinamide. The co-crystal may comprise psilocin and a co-former which is isonicotinamide. The co-crystal may comprise psilocin and a co-former which is tromethamine. The co-crystal may comprise psilocin and a co-former which is tert-butyl amine. The co-crystal may comprise psilocin and a co-former which is diethylamine.

Co-Crystals with a Neutral Compound

Also disclosed herein is a co-crystal comprising psilocin and a co-former, wherein the co-former is a neutral compound. A neutral compound is: (i) a compound which is amphoteric; (ii) a compound which is zwitterionic; (iii) a compound which comprises neither an acidic moiety nor a basic moiety; or (iv) a compound which is an inorganic salt.

The co-former may be a compound which is amphoteric. The co-former may be a compound which is zwitterionic. Typically, the co-former is an amino acid or amino acid derivative.

The co-former may be selected from: DL-alanine, D-alanine, L-alanine, DL-arginine, D-arginine, L-arginine, DL-asparagine, D-asparagine, L-asparagine, DL-aspartic acid, D-aspartic acid, L-aspartic acid, DL-cysteine, D-cysteine, L-cysteine, DL-glutamine, D-glutamine, L-glutamine, DL-glutamic acid, D-glutamic acid, L-glutamic acid, glycine, DL-histidine, D-histidine, L-histidine, DL-isoleucine, D-isoleucine, L-isoleucine, DL-leucine, D-leucine, L-leucine, DL-lysine, D-lysine, L-lysine, DL-methionine, D-methionine, L-methionine, DL-phenylalanine, D-phenylalanine, L-phenylalanine, DL-proline, D-proline, L-proline, DL-serine, D-serine, L-serine, DL-threonine, D-threonine, L-threonine, DL-tryptophan, D-tryptophan, L-tryptophan, DL-tyrosine, D-tyrosine, L-tyrosine, DL-valine, D-valine, L-valine, DL-pyroglutamic acid, D-pyroglutamic acid, L-pyroglutamic acid, DL-selenocysteine, D-selenocysteine, L-selenocysteine, DL-pyrrolysine, D-pyrrolysine, L-pyrrolysine, N-formylmethionine, hydroxyproline, selenomethionine, carnitine, gamma-aminobutyric acid, levothyroxine, 2-aminoisobutyric acid, ornithine, citrulline and beta-alanine.

The co-former may be selected from: L-lysine, L-histidine, L-tyrosine, L-pyroglutamic acid, DL-cysteine, and L-glutamic acid.

Typically, the co-crystal is selected from L-pyroglutamic acid, DL-cysteine, and L-glutamic acid.

The co-former may be a compound which comprises neither an acidic moiety nor a basic moiety. Typically, the co-former is a compound which comprises one or more functional groups selected from: an ester moiety, an ether moiety, an alcohol moiety a phenol moiety, and a carboxamide moiety. Typically, the co-former is a compound which comprises an alcohol moiety and/or a phenol moiety. The co-former may be a compound which comprises an alcohol moiety. The co-former may be a compound which comprises a phenol moiety. The co-former may be a compound which comprises an ester moiety. The co-former may be a compound which comprises an ether moiety. The co-former may be a compound which comprises a carboxamide moiety.

The co-former may be selected from methyl nitrate, methyl formate, methyl acetate, methyl acrylate, methyl propionate, methyl butyrate, methyl pentanoate, methyl benzoate, methyl anthranilate, methyl salicylate, methyl phenylacetate, methyl cinnamate, ethyl formate, ethyl acetate, ethyl propionate, ethyl lactate, ethyl butyrate, ethyl pentanoate, ethyl isovalerate, ethyl hexanoate, ethyl heptanoate, ethyl benzoate, ethyl salicylate, ethyl octanoate, ethyl cinnamate, ethyl decanoate, propyl acetate, propyl propanoate, propyl hexanoate, allyl hexanoate, isopropyl acetate, isopropyl salicylate, isopropyl palmitate, butyl formate, butyl acetate, isobutyl formate, isobutyl acetate, sec-butyl formate, sec-butyl acetate, tert-butyl formate, tert-butyl acetate, butyl butyrate, amyl acetate, pentyl butyrate, pentyl propanoate, pentyl hexanoate, sec-amyl acetate, benzyl acetate, aspartame, ascorbyl palmitate, (ascorbic acid 6-hexadecanoate, including L-ascorbic acid 6-hexadecanoate and D-ascorbic acid 6-hexadecanoate), dimethyl ether, diethyl ether, dimethoxyethane, dioxane, tetrahydrofuran, anisole, crown ethers, polyethylene glycol, polypropylene glycol, maltol, ethyl maltol, meso-erythritol, threitol, mannitol (including D-mannitol, L-mannitol), sorbitol (including D-sorbitol, L-sorbitol, maltitol, xylitol (including D-xylitol, L-xylitol), inosine, phenol, 2-methylphenol, 3-methylphenol, 4-methylphenol, 2-ethylphenol, 3-ethylphenol, 4-ethylphenol, 2-propylphenol, 3-propylphenol, 4-propylphenol, 2-butylphenol, 3-butylphenol, 4-butylphenol, 2,6-dimethyl-4-methylphenol, 2,6-diethyl-4-methylphenol, 2,6-dipropyl-4-methylphenol, 2,6-di-tert-butyl-4-methylphenol, 2,6-dimethyl-4-ethylphenol, 2,6-diethyl-4-ethylphenol, 2,6-dipropyl-4-ethylphenol, 2,6-di-tert-butyl-4-ethylphenol, 2-tert-butyl-4-methylphenol, 2-tert-butyl-4-ethylphenol, 2,6-di-tert-butyl-4-ethylphenol, 2-methoxyphenol, 3-methoxyphenol, 4-methoxyphenol, 2-ethoxyphenol, 3-ethoxyphenol, 4-ethoxyphenol, 2-methyl-4-methoxyphenol, 2-methyl-3-methoxyphenol, 2-methyl-4-ethoxyphenol, 2-methyl-3-ethoxyphenol, 2-tert-butyl-4-methoxyphenol, 2-tert-butyl-3-methoxyphenol, 2-tert-butyl-4-ethoxyphenol, 2-tert-butyl-3-ethoxyphenol, 2-sec-butyl-4-methoxyphenol, 2-sec-butyl-3-methoxyphenol, 2-sec-butyl-4-ethoxyphenol, 2-sec-butyl-3-ethoxyphenol, vanillin, ethyl vanillin, methylparaben ($C_1$ paraben), ethylparaben ($C_2$ paraben), propylparaben ($C_3$ paraben), butylparaben ($C_4$ paraben), propyl 3,4,5-trihydroxybenzoate (propyl gallate), ethyl 3,4,5-trihydroxybenzoate, methyl 3,4,5-trihydroxybenzoate and urea.

The co-former may be selected from: ethyl maltol, meso-erythritol, D-mannitol, D-sorbitol, D-xylitol, inosine, and L-ascorbic acid 6-hexadecanoate. The co-former may be selected from: 2,6-di-tert-butyl-4-methylphenol, 2-tert-butyl-4-methoxyphenol, vanillin, ethyl vanillin, C1-4 parabens, propyl gallate and urea.

Typically, the co-former is selected from: ethyl maltol, meso-erythritol, D-mannitol, D-sorbitol, D-xylitol, inosine, L-ascorbic acid 6-hexadecanoate, propyl gallate, 2,6-di-tert-butyl-4-methylphenol, 2-tert-butyl-4-methoxyphenol and urea.

The co-former may be a compound which is an inorganic salt.

The co-former may be selected from: calcium chloride, potassium dichromate, sodium chloride, sodium dihydrogen phosphate, sodium hydrogen phosphate, trisodium phosphate, calcium dihydrogen phosphate, calcium hydrogen phosphate, tricalcium phosphate, magnesium dihydrogen phosphate, magnesium hydrogen phosphate, trimagnesium phosphate, monopotassium phosphate, dipotassium phosphate, tripotassium phosphate, sodium bisulfate, sodium sulfate, calcium sulfate, magnesium sulfate, potassium sulfate, potassium bisulfate, sodium sulphite, calcium sulphite, magnesium sulphite, potassium sulphite, sodium bisulfite, calcium bisulfite, magnesium bisulfite, potassium bisulfite, acesulfame potassium, acesulfame sodium, and sodium formaldehyde sulfoxylate.

The co-former may be selected from: sodium dihydrogen phosphate, sodium bisulfite, acesulfame potassium and sodium formaldehyde sulfoxylate.

Typically the co-former is selected from: sodium bisulfite, acesulfame potassium, and sodium formaldehyde sulfoxylate.

The co-crystal may comprise psilocin and a co-former which is L-lysine. The co-crystal may comprise psilocin and a co-former which is L-histidine. The co-crystal may comprise psilocin and a co-former which is L-tyrosine. The co-crystal may comprise psilocin and a co-former which is L-pyroglutamic acid. The co-crystal may comprise psilocin and a co-former which is DL-cysteine. The co-crystal may comprise psilocin and a co-former which is L-glutamic acid. The co-crystal may comprise psilocin and a co-former which is ethyl maltol. The co-crystal may comprise psilocin and a co-former which is meso-erythritol. The co-crystal may comprise psilocin and a co-former which is D-mannitol. The co-crystal may comprise psilocin and a co-former which is D-sorbitol. The co-crystal may comprise psilocin and a co-former which is D-xylitol. The co-crystal may comprise psilocin and a co-former which is inosine. The co-crystal may comprise psilocin and a co-former which is L-ascorbic acid 6-hexadecanoate. The co-crystal may comprise psilocin and a co-former which is 2,6-di-tert-butyl-4-methylphenol. The co-crystal may comprise psilocin and a co-former which is 2-tert-butyl-4-methoxyphenol. The co-crystal may comprise psilocin and a co-former which is vanillin. The co-crystal may comprise psilocin and a co-former which is ethyl vanillin. The co-crystal may comprise psilocin and a co-former which is C1-4 parabens. The co-crystal may comprise psilocin and a co-former which is propyl gallate. The co-crystal may comprise psilocin and a co-former which is urea. The co-crystal may comprise psilocin and a co-former which is sodium dihydrogen phosphate. The co-crystal may comprise psilocin and a co-former which is sodium bisulfite. The co-crystal may comprise psilocin and a co-former which is acesulfame potassium. The co-crystal may comprise psilocin and a co-former which is sodium formaldehyde sulfoxylate.

The co-crystal may comprise one or more additional co-formers. Typically, however, the co-crystal comprises a single co-former.

The co-former typically is a compound having a molar mass of no greater than 500 g/mol, no greater than 350 g/mol or no greater than 200 g/mol. The co-former may have a molar mass of at least 30 g/mol, at least 50 g/mol or at least 100 g/mol.

The co-former may contain one or more chiral centres. Unless otherwise specified, references herein to a co-former encompass all enantiomeric and diastereomeric forms of the co-former, mixtures thereof (e.g. racemic mixtures) and enantiomerically and diastereomerically pure forms thereof.

Stoichiometry

The molar ratio of psilocin:co-former in the co-crystal may be from 1:0.25 to 1:4. The molar ratio of psilocin:co-former may be from 1:0.25 to 1:3, or from 1:0.5 to 1:3, or from 1:0.5 to 1:2, or from 1:0.5 to 1:1.5. Typically, the molar ratio of psilocin:co-former in the co-crystal is from 1:0.5 to 1:3, or from 1:0.5 to 1:2.

The molar ratio of psilocin:co-former in the co-crystal may be about 1:0.25, about 1:0.5, about 1:0.6, about 1:0.7, about 1:0.75, about 1:0.8, about 1:0.9, about 1:1, about 1:1.1, about 1:1.2, about 1:1.25, about 1:1.3, about 1:1.4, about 1:1.5, about 1:1.6, about 1:1.7, about 1:1.75, about 1:1.8, about 1:1.9, about 1:2, about 1:2.5, about 1:3, about 1:3.5, or about 1:4. Typically, the molar ratio of psilocin:co-former in the co-crystal is about 1:0.5, about 1:1, or about 1:2. The molar ratio of psilocin:co-former in the co-crystal may be 1:0.5, for instance 1.0:0.50. The molar ratio of psilocin:co-former in the co-crystal may be 1:1, for instance 1.0:1.0. The molar ratio of psilocin:co-former in the co-crystal may be 1:2, for instance 1.0:2.0.

If the co-crystal comprises more than one co-former, the molar ratio of psilocin to each co-former may be as defined above. Alternatively, the molar ratio of psilocin to the total amount of co-former may be as defined above.

As used herein, the term "about" means any value that the skilled person would appreciate is a reasonable variation of the value that is referred to by the term "about". Typically, "about" means±10% or ±5%.

In one embodiment, the co-crystal is a co-crystal comprising psilocin and citric acid, wherein the molar ratio of psilocin:citric acid is 1:1. Alternatively, the co-crystal may be a co-crystal comprising psilocin and citric acid, wherein the molar ratio of psilocin:citric acid is 1:0.5. Alternatively, the co-crystal may be a co-crystal comprising psilocin and citric acid, wherein the molar ratio of psilocin:citric acid is 1:2.

In one embodiment, the co-crystal is a co-crystal comprising psilocin and fumaric acid, wherein the molar ratio of psilocin:fumaric acid is 1:1. Alternatively, the co-crystal may be a co-crystal comprising psilocin and fumaric acid, wherein the molar ratio of psilocin:fumaric acid is 1:0.5. Alternatively, the co-crystal may be a co-crystal comprising psilocin and fumaric acid, wherein the molar ratio of psilocin:fumaric acid is 1:2.

In one embodiment, the co-crystal is a co-crystal comprising psilocin and succinic acid, wherein the molar ratio of psilocin:succinic acid is 1:1. Alternatively, the co-crystal may be a co-crystal comprising psilocin and succinic acid, wherein the molar ratio of psilocin:succinic acid is 1:0.5. Alternatively, the co-crystal may be a co-crystal comprising psilocin and succinic acid, wherein the molar ratio of psilocin:succinic acid is 1:2.

In one embodiment, the co-crystal is a co-crystal comprising psilocin and gluconic acid, wherein the molar ratio of psilocin:gluconic acid is 1:1. Alternatively, the co-crystal may be a co-crystal comprising psilocin and gluconic acid, wherein the molar ratio of psilocin:gluconic acid is 1:0.5. Alternatively, the co-crystal may be a co-crystal comprising psilocin and gluconic acid, wherein the molar ratio of psilocin:gluconic acid is 1:2.

In one embodiment, the co-crystal is a co-crystal comprising psilocin and L-tartaric acid, wherein the molar ratio of psilocin:L-tartaric acid is 1:1. Alternatively, the co-crystal may be a co-crystal comprising psilocin and L-tartaric acid, wherein the molar ratio of psilocin:L-tartaric acid is 1:0.5. Alternatively, the co-crystal may be a co-crystal comprising psilocin and L-tartaric acid, wherein the molar ratio of psilocin:L-tartaric acid is 1:2.

In one embodiment, the co-crystal is a co-crystal comprising psilocin and L-ascorbic acid, wherein the molar ratio of psilocin:L-ascorbic acid is 1:1. Alternatively, the co-crystal may be a co-crystal comprising psilocin and L-ascorbic acid, wherein the molar ratio of psilocin:L-ascorbic acid is 1:0.5. Alternatively, the co-crystal may be a co-crystal comprising psilocin and L-ascorbic acid, wherein the molar ratio of psilocin:L-ascorbic acid is 1:2.

In one embodiment, the co-crystal is a co-crystal comprising psilocin and L-lactic acid, wherein the molar ratio of psilocin:L-lactic acid is 1:1. Alternatively, the co-crystal may be a co-crystal comprising psilocin and L-lactic acid, wherein the molar ratio of psilocin:L-lactic acid is 1:0.5. Alternatively, the co-crystal may be a co-crystal comprising psilocin and L-lactic acid, wherein the molar ratio of psilocin:L-lactic acid is 1:2.

In one embodiment, the co-crystal is a co-crystal comprising psilocin and saccharin, wherein the molar ratio of psilocin:saccharin is 1:1. Alternatively, the co-crystal may be a co-crystal comprising psilocin and saccharin, wherein the molar ratio of psilocin:saccharin is 1:0.5. Alternatively, the co-crystal may be a co-crystal comprising psilocin and saccharin, wherein the molar ratio of psilocin:saccharin is 1:2.

In one embodiment, the co-crystal is a co-crystal comprising psilocin and disodium EDTA, wherein the molar ratio of psilocin:disodium EDTA is 1:1. Alternatively, the co-crystal may be a co-crystal comprising psilocin and disodium EDTA, wherein the molar ratio of psilocin:disodium EDTA is 1:0.5. Alternatively, the co-crystal may be a co-crystal comprising psilocin and disodium EDTA, wherein the molar ratio of psilocin:disodium EDTA is 1:2.

In one embodiment, the co-crystal is a co-crystal comprising psilocin and nicotinic acid, wherein the molar ratio of psilocin:nicotinic acid is 1:1. Alternatively, the co-crystal may be a co-crystal comprising psilocin and nicotinic acid, wherein the molar ratio of psilocin:nicotinic acid is 1:0.5. Alternatively, the co-crystal may be a co-crystal comprising psilocin and nicotinic acid, wherein the molar ratio of psilocin:nicotinic acid is 1:2.

In one embodiment, the co-crystal is a co-crystal comprising psilocin and theophylline, wherein the molar ratio of psilocin:theophylline is 1:1. Alternatively, the co-crystal may be a co-crystal comprising psilocin and theophylline, wherein the molar ratio of psilocin:theophylline is 1:0.5. Alternatively, the co-crystal may be a co-crystal comprising psilocin and theophylline, wherein the molar ratio of psilocin:theophylline is 1:2.

In one embodiment, the co-crystal is a co-crystal comprising psilocin and nicotinamide, wherein the molar ratio of psilocin:nicotinamide is 1:1. Alternatively, the co-crystal may be a co-crystal comprising psilocin and nicotinamide, wherein the molar ratio of psilocin:nicotinamide is 1:0.5. Alternatively, the co-crystal may be a co-crystal comprising psilocin and nicotinamide, wherein the molar ratio of psilocin:nicotinamide is 1:2.

In one embodiment, the co-crystal is a co-crystal comprising psilocin and isonicotinamide, wherein the molar ratio of psilocin:isonicotinamide is 1:1. Alternatively, the co-crystal may be a co-crystal comprising psilocin and isonicotinamide, wherein the molar ratio of psilocin:isonicotinamide is 1:0.5. Alternatively, the co-crystal may be a co-crystal comprising psilocin and isonicotinamide, wherein the molar ratio of psilocin:isonicotinamide is 1:2.

In one embodiment, the co-crystal is a co-crystal comprising psilocin and tromethamine, wherein the molar ratio of psilocin:tromethamine is 1:1. Alternatively, the co-crystal may be a co-crystal comprising psilocin and tromethamine, wherein the molar ratio of psilocin:tromethamine is 1:0.5. Alternatively, the co-crystal may be a co-crystal comprising psilocin and tromethamine, wherein the molar ratio of psilocin:tromethamine is 1:2.

In one embodiment, the co-crystal is a co-crystal comprising psilocin and L-pyroglutamic acid, wherein the molar ratio of psilocin:L-pyroglutamic acid is 1:1. Alternatively, the co-crystal may be a co-crystal comprising psilocin and L-pyroglutamic acid, wherein the molar ratio of psilocin:L-pyroglutamic acid is 1:0.5. Alternatively, the co-crystal may be a co-crystal comprising psilocin and L-pyroglutamic acid, wherein the molar ratio of psilocin:L-pyroglutamic acid is 1:2.

In one embodiment, the co-crystal is a co-crystal comprising psilocin and DL-cysteine, wherein the molar ratio of psilocin:DL-cysteine is 1:1. Alternatively, the co-crystal may be a co-crystal comprising psilocin and DL-cysteine, wherein the molar ratio of psilocin:DL-cysteine is 1:0.5. Alternatively, the co-crystal may be a co-crystal comprising psilocin and DL-cysteine, wherein the molar ratio of psilocin: DL-cysteine is 1:2.

In one embodiment, the co-crystal is a co-crystal comprising psilocin and L-glutamic acid, wherein the molar ratio of psilocin:L-glutamic acid is 1:1. Alternatively, the co-crystal may be a co-crystal comprising psilocin and L-glutamic acid, wherein the molar ratio of psilocin:L-glutamic acid is 1:0.5. Alternatively, the co-crystal may be a co-crystal comprising psilocin and L-glutamic acid, wherein the molar ratio of psilocin:L-glutamic acid is 1:2.

In one embodiment, the co-crystal is a co-crystal comprising psilocin and ethyl maltol, wherein the molar ratio of psilocin:ethyl maltol is 1:1. Alternatively, the co-crystal may be a co-crystal comprising psilocin and ethyl maltol, wherein the molar ratio of psilocin:ethyl maltol is 1:0.5. Alternatively, the co-crystal may be a co-crystal comprising psilocin and ethyl maltol, wherein the molar ratio of psilocin:ethyl maltol is 1:2.

In one embodiment, the co-crystal is a co-crystal comprising psilocin and meso-erythritol, wherein the molar ratio of psilocin:meso-erythritol is 1:1. Alternatively, the co-crystal may be a co-crystal comprising psilocin and meso-erythritol, wherein the molar ratio of psilocin:meso-erythritol is 1:0.5. Alternatively, the co-crystal may be a co-crystal comprising psilocin and meso-erythritol, wherein the molar ratio of psilocin:meso-erythritol is 1:2.

In one embodiment, the co-crystal is a co-crystal comprising psilocin and D-mannitol, wherein the molar ratio of psilocin:D-mannitol is 1:1. Alternatively, the co-crystal may be a co-crystal comprising psilocin and D-mannitol, wherein the molar ratio of psilocin:D-mannitol is 1:0.5. Alternatively, the co-crystal may be a co-crystal comprising psilocin and D-mannitol, wherein the molar ratio of psilocin:D-mannitol is 1:2.

In one embodiment, the co-crystal is a co-crystal comprising psilocin and D-sorbitol, wherein the molar ratio of psilocin:D-sorbitol is 1:1. Alternatively, the co-crystal may be a co-crystal comprising psilocin and D-sorbitol, wherein the molar ratio of psilocin:D-sorbitol is 1:0.5. Alternatively, the co-crystal may be a co-crystal comprising psilocin and D-sorbitol, wherein the molar ratio of psilocin:D-sorbitol is 1:2.

In one embodiment, the co-crystal is a co-crystal comprising psilocin and D-xylitol, wherein the molar ratio of psilocin:D-xylitol is 1:1. Alternatively, the co-crystal may be a co-crystal comprising psilocin and D-xylitol, wherein the molar ratio of psilocin:D-xylitol is 1:0.5. Alternatively, the co-crystal may be a co-crystal comprising psilocin and D-xylitol, wherein the molar ratio of psilocin:D-xylitol is 1:2.

In one embodiment, the co-crystal is a co-crystal comprising psilocin and inosine, wherein the molar ratio of psilocin:inosine is 1:1. Alternatively, the co-crystal may be a co-crystal comprising psilocin and inosine, wherein the molar ratio of psilocin:inosine is 1:0.5. Alternatively, the co-crystal may be a co-crystal comprising psilocin and inosine, wherein the molar ratio of psilocin:inosine is 1:2.

In one embodiment, the co-crystal is a co-crystal comprising psilocin and L-ascorbic acid 6-hexadecanoate, wherein the molar ratio of psilocin:L-ascorbic acid 6-hexadecanoate is 1:1. Alternatively, the co-crystal may be a co-crystal comprising psilocin and L-ascorbic acid 6-hexadecanoate, wherein the molar ratio of psilocin:L-ascorbic acid 6-hexadecanoate is 1:0.5. Alternatively, the co-crystal may be a co-crystal comprising psilocin and L-ascorbic acid 6-hexadecanoate, wherein the molar ratio of psilocin:L-ascorbic acid 6-hexadecanoate is 1:2.

In one embodiment, the co-crystal is a co-crystal comprising psilocin and propyl gallate, wherein the molar ratio of psilocin:propyl gallate is 1:1. Alternatively, the co-crystal may be a co-crystal comprising psilocin and propyl gallate, wherein the molar ratio of psilocin:propyl gallate is 1:0.5. Alternatively, the co-crystal may be a co-crystal comprising psilocin and propyl gallate, wherein the molar ratio of psilocin:propyl gallate is 1:2.

In one embodiment, the co-crystal is a co-crystal comprising psilocin and 2,6-di-tert-butyl-4-methylphenol, wherein the molar ratio of psilocin:2,6-di-tert-butyl-4-methylphenol is 1:1. Alternatively, the co-crystal may be a co-crystal comprising psilocin and 2,6-di-tert-butyl-4-methylphenol, wherein the molar ratio of psilocin:2,6-di-tert-butyl-4-methylphenol is 1:0.5. Alternatively, the co-crystal may be a co-crystal comprising psilocin and 2,6-di-tert-butyl-4-methylphenol, wherein the molar ratio of psilocin: 2,6-di-tert-butyl-4-methylphenol is 1:2.

In one embodiment, the co-crystal is a co-crystal comprising psilocin and 2-tert-butyl-4-methoxyphenol, wherein the molar ratio of psilocin:2-tert-butyl-4-methoxyphenol is 1:1. Alternatively, the co-crystal may be a co-crystal comprising psilocin and 2-tert-butyl-4-methoxyphenol, wherein the molar ratio of psilocin:2-tert-butyl-4-methoxyphenol is 1:0.5. Alternatively, the co-crystal may be a co-crystal comprising psilocin and 2-tert-butyl-4-methoxyphenol, wherein the molar ratio of psilocin:2-tert-butyl-4-methoxyphenol is 1:2.

In one embodiment, the co-crystal is a co-crystal comprising psilocin and urea, wherein the molar ratio of psilocin:urea is 1:1. Alternatively, the co-crystal may be a co-crystal comprising psilocin and urea, wherein the molar ratio of psilocin:urea is 1:0.5. Alternatively, the co-crystal may be a co-crystal comprising psilocin and urea, wherein the molar ratio of psilocin:urea is 1:2.

In one embodiment, the co-crystal is a co-crystal comprising psilocin and sodium bisulfite, wherein the molar ratio of psilocin:sodium bisulfite is 1:1. Alternatively, the co-crystal may be a co-crystal comprising psilocin and sodium bisulfite, wherein the molar ratio of psilocin:sodium bisulfite is 1:0.5. Alternatively, the co-crystal may be a co-crystal comprising psilocin and sodium bisulfite, wherein the molar ratio of psilocin:sodium bisulfite is 1:2.

In one embodiment, the co-crystal is a co-crystal comprising psilocin and acesulfame potassium, wherein the molar ratio of psilocin:acesulfame potassium is 1:1. Alternatively, the co-crystal may be a co-crystal comprising psilocin and acesulfame potassium, wherein the molar ratio of psilocin:acesulfame potassium is 1:0.5. Alternatively, the co-crystal may be a co-crystal comprising psilocin and acesulfame potassium, wherein the molar ratio of psilocin: acesulfame potassium is 1:2.

In one embodiment, the co-crystal is a co-crystal comprising psilocin and sodium formaldehyde sulfoxylate, wherein the molar ratio of psilocin:sodium formaldehyde sulfoxylate is 1:1. Alternatively, the co-crystal may be a co-crystal comprising psilocin and sodium formaldehyde sulfoxylate, wherein the molar ratio of psilocin:sodium formaldehyde sulfoxylate is 1:0.5. Alternatively, the co-crystal may be a co-crystal comprising psilocin and sodium formaldehyde sulfoxylate, wherein the molar ratio of psilocin:sodium formaldehyde sulfoxylate is 1:2.

Solvates and Hydrates

The co-crystal may be in the form of a solvate. The term "solvate" as used herein describes a co-crystals that have solvent molecules (typically organic solvents) incorporated into their co-crystal lattice. As such, the co-crystal solvate comprises the active agent, the co-former and the solvent molecules. A solvate may contain molecules of organic solvent and water. A hydrate is a solvate which contains incorporated water molecules as the only solvent molecules.

The solvate is typically a solvate with an organic solvent. Suitable organic solvents are known to the person skilled in the art. For example, the organic solvent may be carbon tetrachloride, 1,2-dichloroethane, 1,1-dichloroethane, 1,1,1-trichloroethane, acetonitrile, chlorobenzene, chloroform, cumene, cyclohexane, cyclopentyl methyl ether, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, t-butyl alcohol, tetrahydrofuran, tetralin, toluene, 1,1,2-trichloroethene, xylene, acetic acid, acetone, anisole, 1-butanol, 2-butanol, butyl acetate, t-butyl methyl ether, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, 2-methyltetrahydrofuran, pentane, 1-pentanol, 1-propanol, 2-propanol, propyl acetate, triethylamine, 1,1-diethoxypropane, 1,1-dimethoxymethane, 2,2-dimethoxypropane, isooctane, isopropyl ether, methylisopropyl ketone, 2-methyltetrahydrofuran, petroleum ether, trichloroacetic acid, 2,2,2-trifluoroethanol, 1,1,1,3,3,3-hexafluoropropan-2-ol, (trifluoromethyl)benzene or trifluoroacetic acid.

Typically, the organic solvent is selected from: acetonitrile, chlorobenzene, chloroform, cumene, cyclohexane, cyclopentyl methyl ether, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, t-butyl alcohol, tetrahydrofuran, tetralin, toluene, 1,1,2-trichloroethene, xylene, acetic acid, acetone, anisole, 1-butanol, 2-butanol, butyl acetate, t-butyl methyl ether, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, 2-methyltetrahydrofuran, pentane, 1-pentanol, 1-propanol, 2-propanol, propyl acetate, triethylamine, 1,1-diethoxypropane, 1,1-dimethoxymethane, 2,2-dimethoxypropane, isooctane, isopropyl ether, methylisopropyl ketone, 2-methyltetrahydrofuran, petroleum ether, 2,2,2-trifluoroethanol, 1,1,1,3,3,3-hexafluoropropan-2-ol, (trifluoromethyl)benzene, trichloroacetic acid, and trifluoroacetic acid.

Typically, the organic solvent is a pharmaceutically acceptable organic solvent.

The co-crystal may be in the form a hydrate. Alternatively, the co-crystal may be in the form of a non-hydrate. The co-crystal may be anhydrous.

The solvate and/or hydrate may be stoichiometric, i.e. have a molar ratio of co-crystal:solvent of 1:1. Alternatively, the solvate and/or hydrate may be non-stoichiometric, i.e. have a non-integer molar ratio of co-crystal:solvent, for example 1:1.1. A non-stoichiometric solvate and/or hydrate may also be known as a channel solvate and/or hydrate.

Process for Producing Co-Crystals

The process for producing a co-crystal as described herein comprises combining psilocin and a co-former, for example a co-former which is an acid, a base or a neutral compound. Suitable methods are well known to the person skilled in the art.

The process may comprise reactive crystallisation. Reactive crystallisation typically comprises combining a solution of psilocin with a solution of the co-former, stirring, and isolating the resulting co-crystal.

The process may comprise crystallisation. Crystallisation typically comprises dissolving psilocin and the co-former (either directly or via mechanical grinding) in a solvent or solvent system to yield a clear solution, allowing supersaturation, and isolating the resulting co-crystal.

The process may comprise slurry or suspension mediated crystallisation. Slurry or suspension mediated crystallisation typically comprises suspending psilocin and the co-former in a solvent or solvent system such that a small fraction remains in excess, stirring the suspension, and isolating the resulting co-crystal.

The process may comprise solid state grinding. Solid state grinding typically comprises grinding psilocin and the co-former together, and isolating the resulting co-crystal.

The process may comprise liquid assisted grinding. Liquid assisted grinding typically comprises mixing psilocin and the co-former in a small volume (typically, but not confined to, 1:4 volume:weight ratio of total solid) of a solvent/solvent system, grinding the psilocin with the co-former (including grinding using a resonant acoustic mixer), and isolating the resulting co-crystal.

The process may comprise a solid state mediated process. A solid state mediated process typically comprises mixing psilocin and the co-former, and either exposing to laser irradiation or an electrochemical source, then isolating the resulting co-crystal.

The process may comprise melt mediated crystallisation. Melt mediated crystallisation typically comprises simultaneously mixing the psilocin and co-former and melting the psilocin and co-former, and isolating the resulting co-crystal.

Pharmaceutical Compositions

The present invention provides a pharmaceutical composition comprising the co-crystal and a pharmaceutically acceptable excipient or diluent. The co-crystal may be as further defined herein.

An appropriate conventional excipient or diluent will depend on the mode of administration used. Pharmaceutically acceptable excipients and diluents are well known to the skilled person. The pharmaceutical composition may further comprise one or more of a buffer, a lubricant, a diluent, or a carrier.

Methods of Treatment

The co-crystal of the invention may be useful as a medicament. In one embodiment, the invention provides a co-crystal as described herein for use as a medicine.

In one embodiment, the invention provides a method of treating or preventing a disease or condition selected from psychological, neurological and central nervous system disorders.

The disease or condition may be selected from: disruptive mood dysregulation disorder, depression, major depressive disorder (MDD), treatment-resistant depression, persistent depressive disorder (dysthymia), demoralization, hopelessness, premenstrual dysphoric disorder, substance/medication-induced depressive disorder, post-partum depression, depressive disorder due to another medical condition, separation anxiety disorder, selective mutism, specific phobia, social anxiety disorder (social phobia), panic disorder, panic attack, agoraphobia, generalized anxiety disorder, anxiety, death anxiety, substance-medication-induced anxiety disorder, anxiety disorder due to another medical condition, somatic symptom disorder, illness anxiety disorder (hypochondriac), conversion disorder (functional neurological symptom disorder), factitious disorder, post-traumatic stress disorder (PTSD), adjustment disorders, acute distress disorder, obsessive-compulsive disorder, body dysmorphic disorder, hoarding disorder, trichotillomania (hair-pulling) disorder, excoriation (skin-picking) disorder, substance/medication-induced obsessive-compulsive and related disorder, obsessive-compulsive and related disorder due to another medical condition, substance-related disorders, alcohol-related disorders, cannabis-related disorders, hallucinogen-related disorders, inhalant-related disorders, cocaine-related disorders, opioid-related disorders, sedative-, hypnotic-, or anxiolytic-related disorders, stimulant-related disorders, tobacco-related disorders, non-substance-related disorders (gambling or gaming disorder), migraines, cluster headaches (including chronic cluster headaches), cyclical vomiting, tension-type headache, dysphasia, pica, anorexia nervosa, bulimia nervosa, binge-eating disorder, oppositional defiant disorder, intermittent explosive disorder, conduct disorder, antisocial personality disorder, psychopathy, pyromania, kleptomania, autism spectrum disorder, antisocial personality disorder, attention-deficit/hyperactivity disorder, schizotypal (personality) disorder, delusional disorder, schizophrenia, schizoaffective disorder, insomnia disorder, hypersomnolence disorder, narcolepsy, primary central sleep apnea, bipolar I disorder, bipolar II disorder, cyclothymic disorder, pain, phantom pain, chronic pain, myelopathy, traumatic brain injury, intellectual disabilities, mania, neurodegeneration, paraphilic disorders (e.g, paedophilic disorder), suicidal behavior disorder, suicidal ideation, desire for hastened death, non-suicidal self-injury, persistent complex bereavement disorder, epilepsy, locked-in syndrome and restless leg syndrome.

In one embodiment, the method is a method of treating or preventing a disease or condition selected from depression, anxiety, death anxiety, demoralization, adjustment disorders, hopelessness, suicidal ideation and desire for hastened death.

In one embodiment, the method is a method of treating or preventing cocaine-related disorders, opioid-related disorders, or stimulant-related disorders.

The method may be a method of treating or preventing depression in a patient. The method may be a method of treating or preventing anxiety in a patient. As used herein, treating or preventing depression and/or anxiety includes reducing the symptoms of depression and/or anxiety or achieving remission of depression and/or anxiety. In one embodiment, treating or preventing depression and/or anxiety comprises reducing the symptoms of depression and/or anxiety. The patient may report a reduction of symptoms of depression and/or anxiety.

In one embodiment, the patient has been identified as being in need of treatment to alleviate depression and/or anxiety. In one embodiment, the patient has indicated that he or she is suffering from depression and/or anxiety.

The symptoms of depression and/or anxiety may be measured using the Hospital Anxiety and Depression Scale (HADS; Zigmond and Snaith (1983), "The hospital anxiety and depression Scale", Acta Psychiatrica Scand, 67: 361-370). In this test, lower numbers indicate lower levels of depression and/or anxiety. Subscale scores can be calculated for depression (HADS-D) and anxiety (HADS-A). A subscale score equal to or above 8 and a full scale score over 12 indicates the possible presence of a clinical disorder.

Accordingly, in the method of the invention a total Hospital Anxiety and Depression Scale score of the patient may be reduced after administration of the co-crystal. In one embodiment, the total HADS score of the patient is reduced to below about 12 after administration of the co-crystal.

The severity of depression may also be measured using the Beck Depression Inventory-II (BDI-II; Beck et al (1988), "Psychometric properties of the Beck Depression Inventory: Twenty-five years of evaluation", *Clin Psych Rev,* 8: 77-100). Scores above 12 indicate possible clinical depression.

Accordingly, in the method of the invention a Beck Depression Inventory-II score of the patient may be reduced after administration of the co-crystal. In one embodiment, the Beck Depression Inventory-II score of the patient is reduced to below about 12 after administration of the co-crystal.

The method may be a method of treating or preventing death anxiety. The method may be a method of treating or preventing demoralization (i.e. loss of meaning in life). The method may be a method of treating or preventing hopelessness. Death anxiety, demoralization and hopelessness are aspects of existential distress. Thus, the method may also be a method of treating or preventing existential distress in a patient, wherein treating or preventing existential distress includes reducing levels of at least one of death anxiety, hopelessness and demoralization.

In the method of treating or preventing death anxiety in a patient, death anxiety is reduced relative to the death anxiety of the patient before the administration of the co-crystal. Death anxiety is typically measured according to the Death Anxiety Scale (Templer (1970), "The construction and validation of a death anxiety scale", *J Gen Psychol,* 82: 165-177). Scores below 8 are considered normative levels of death anxiety. Accordingly, in the method of the invention a death anxiety score of the patient may be reduced to less than 8 after administration of the co-crystal.

In the method of treating or preventing demoralization in a patient, demoralization is reduced relative to the demoralization of the patient before the administration of the co-crystal. Demoralization is typically measured according to the Demoralization Scale (Kissane et al. (2004), "The demoralization scale: A report of its development and preliminary validation", *J Palliat Care,* 20: 269-276). Scores above 30 are considered indicative of clinical levels of demoralization. Accordingly, in the method of the invention a demoralization score of the patient may be reduced to less than 30 after administration of the co-crystal.

In the method of treating or preventing hopelessness in a patient, hopelessness is reduced relative to the hopelessness of the patient before the administration of the co-crystal. Hopelessness is typically measured according to the Hopelessness Assessment in Illness instrument (Rosenfeld et al. (2011), "Assessing hopelessness in terminally ill cancer patients: Development of the Hopelessness Assessment in Illness Questionnaire", *Psychol Assess,* 23: 325-336), on a scale of 0-16. Higher scores indicate higher levels of hopelessness. Accordingly, in the method of the invention a Hopelessness Assessment in Illness score of the patient may be reduced to less than 8 after administration of the co-crystal.

The method may be a method of treating or preventing suicidal ideation in a patient. As used herein, treating or preventing suicidal ideation includes reducing or preventing suicidal thinking, suicidal planning and/or suicide attempts. The patient may report a reduction in suicidal thinking and/or suicidal planning. The patient may make less frequent suicide attempts.

In one embodiment, the patient has been identified as being in need of treatment to prevent or reduce suicidal ideation. Accordingly, the method of the invention may include a step of assessing the level of suicidal ideation in the patient prior to administering the co-crystal to said patient. In one embodiment, the patient has indicated that he or she is suffering from suicidal ideation.

Suicidal ideation may be measured using a composite test comprising elements from the Beck Depression Inventory-II (BDI-II; Beck et al (1988), "Psychometric properties of the Beck Depression Inventory: Twenty-five years of evaluation", *Clin Psych Rev,* 8: 77-100) and the Brief Symptom Inventory (BSI; Derogatis 1993). In the BDI, Item #9 queries suicidal ideation with the following options: 0=I don't have any thoughts of killing myself; 1=I have thoughts of killing myself, but I would not carry them out; 2=I would like to kill myself; 3=I would kill myself if I had the chance. In the BSI, item #9 ("Thoughts of ending your life") also correlates to suicidal ideation, and is measured on a Likert scale: 0=Not at all; 1=Little; 2=Moderately; 3=Quite a bit; 4=Extremely. The aggregate composite suicidal ideation score is calculated by adding the scores from BDI-II item #9 to BSI Item #9. The composite score may be calculated by computing Z-scores for each item and summing them, and then the composite Z-scores may be transformed into standardized T-scores with a range of 0 to 100 (Song et al., 2013). Higher scores indicate higher suicidal ideation.

Accordingly, in the method of the invention a composite suicidal ideation score of the patient may be reduced after administration of the co-crystal. Typically, a composite suicidal ideation score of the patient is reduced by at least 20%, at least 30%, at least 40%, at least 50% or at least 75% after administration of the co-crystal. In one embodiment, a composite suicidal ideation score of the patient after administration of the co-crystal is less than 50, less than 45 or less than 40.

The method may be a method of treating or preventing desire for hastened death in a patient. As used herein, treating or preventing desire for hastened death includes preventing or reducing the desire for a more rapid death than would naturally occur. The patient may report a reduction in desire for a more rapid death than would naturally occur.

In one embodiment, the patient has been identified as being in need of treatment to prevent or reduce desire for hastened death. Accordingly, the method of the invention may include a step of assessing the level of desire for hastened death in the patient prior to administering the co-crystal to said patient. In one embodiment, the patient has indicated that he or she is suffering from desire for hastened death.

Desire for hastened death may be measured using the schedule of attitudes towards hastened death (SAHD) (Rosenfeld 2000). The SAHD is a 20-item true/false measure of desire for hastened death, which has been validated in patients with cancer. Alternatively, DHD can be measured using the loss of meaning factor from the Demoralization Scale (Kissane et al. (2004)). In particular, a composite desire for hastened death score can be created from the following five items from the loss of meaning factor, as measured on a Likert scale from zero to four: "Life is no longer worth living", "I would rather not be alive", "My life seems to be pointless", "My role in life has been lost", and "There is no purpose to the activities in my life".

Accordingly, in the method of the invention a composite desire for hastened death score of the patient may be reduced after administration of the co-crystal. Typically, a composite desire for hastened death score of the patient is reduced by at least 20%, at least 40%, at least 60% or at least 80% after administration of the co-crystal.

The method of the invention comprises administering a therapeutically effective amount of a co-crystal as defined herein to the patient. The therapeutically effective amount may be any amount of co-crystal which contains an amount of psilocin that is effective in treating and/or preventing a disease or condition as described herein. An effective amount of psilocin may be from about 0.001 mg/kg to about 10 mg/kg, for instance from about 0.01 mg/kg to about 1 mg/kg, where mg/kg is mg per kg of the patient's body weight at the time of the administration of the co-crystal. Typically, an effective amount of psilocin may be a dose of from about 0.1 mg/kg to about 0.5 mg/kg, or from about 0.2 mg/kg to about 0.4 mg/kg. In one embodiment, the effective amount of psilocin is about 0.3 mg/kg.

In the method of the invention, the therapeutically effective amount of the co-crystal may be administered as a single dose or as multiple doses. Typically, the therapeutically effective amount of the co-crystal is administered as a single dose.

A single dose of the co-crystal may contain from about 0.1 to about 100 mg of psilocin. In one embodiment, the psilocin is administered in a single effective dose of from about 10 mg to about 40 mg. Typically, the single dose may be from about 10 mg to about 35 mg, or from about 15 mg to about 30 mg, or from about 20 mg to about 30 mg. In one embodiment, the single dose is about 25 mg. In one embodiment, the single dose is from about 1 mg to about 10 mg.

The co-crystal may be administered to the patient by any acceptable route of administration including, but not limited to, inhaled, oral, nasal, topical (including transdermal) and parenteral modes of administration. The co-crystal may be administered as, for example: a tablet, capsule, powder, solution or suspension for oral administration; a solution or suspension for injection; or a solution, suspension or powder for inhalation.

The patient to be treated may be suffering from a life-threatening disease. The life-threatening disease may be any chronic disease which has the potential to reduce the normal life expectancy of a patient suffering from the disease. The life-threatening disease may be selected from cancer, heart disease, chronic obstructive pulmonary disease (COPD), diabetes mellitus, Alzheimer's, dementia, motor neurone disease, amyotrophic lateral sclerosis (ALS), Parkinson's disease, epilepsy, multiple sclerosis, and myalgic encephalopathy (ME). In one embodiment, the life-threatening disease is cancer.

Also provided by the invention is a co-crystal as described herein for use in the treatment or prevention of a disease or condition as described herein. In one embodiment, the invention provides a co-crystal as described herein for use in the treatment or prevention of a disease or condition selected from depression, anxiety, death anxiety, demoralization, adjustment disorders, hopelessness, suicidal ideation and desire for hastened death. In one embodiment, the disease or condition is selected from cocaine-related disorders, opioid-related disorders and stimulant-related disorders.

The invention further provides use of a co-crystal as described herein in the manufacture of a medicament for the treatment or prevention of a disease or condition as described herein. In one embodiment, the invention provides use of a co-crystal as described herein in the manufacture of a medicament for the treatment or prevention of a disease or condition selected from depression, anxiety, death anxiety, demoralization, adjustment disorders, hopelessness, suicidal ideation and desire for hastened death. In one embodiment, the disease or condition is selected from cocaine-related disorders, opioid-related disorders and stimulant-related disorders. The treatment or prevention of the disease or condition may be as described herein.

Kits

The kit of the invention comprises a co-crystal or a pharmaceutical composition as described herein, and instructions for use of the co-crystal or pharmaceutical composition in a method of treating or preventing a disease or condition selected from depression, anxiety, death anxiety, demoralization, adjustment disorders, hopelessness, suicidal ideation and desire for hastened death. The kit may comprise instructions for use of the co-crystal or pharmaceutical composition in a method of treating or preventing a disease or condition selected from cocaine-related disorders, opioid-related disorders and stimulant-related disorders.

Salts

The invention also provides a salt comprising psilocin and a co-former as described herein. Typically, if psilocin and the co-former have a $\Delta pK_a$ ($pK_a$ (conjugate acid of base)$-pK_a$ (acid)$\geq 1$, there will be substantial proton transfer between psilocin and the co-former, leading to potential formation of a salt.

For instance, the invention provides a salt of psilocin and decanoic acid. The salt of psilocin and decanoic acid may be in the crystalline form designated as decanoic acid Pattern 1 or Pattern 2. The invention also provides a salt of psilocin and ethyl maltol. The salt of psilocin and ethyl maltol may be in the crystalline form designated as ethyl maltol Pattern 1. The invention also provides a salt of psilocin and L-lactic acid. The salt of psilocin and L-lactic acid may be in the crystalline form designated as L-lactic acid Pattern 1. The invention also provides a salt of psilocin and oleic acid. The salt of psilocin and oleic acid may be in the crystalline form designated as oleic acid Pattern 1. The invention also provides a salt of psilocin and palmitic acid. The salt of psilocin and palmitic acid may be in the crystalline form designated as palmitic acid Pattern 1. The invention also provides a salt of psilocin and p-coumaric acid. The salt of psilocin and p-coumaric acid may be in the crystalline form designated as p-coumaric acid Pattern 1. The invention also provides a salt of psilocin and propyl gallate. The salt of psilocin and propyl gallate may be in the crystalline form designated as propyl gallate Pattern 1. The invention also provides a salt of psilocin and stearic acid. The salt of psilocin and stearic acid may be in the crystalline form designated as stearic acid Pattern 1 or Pattern 2.

The salt of psilocin and decanoic acid may be in the crystalline form designated as decanoic acid Pattern 1, wherein Pattern 1 has an x-ray powder diffraction (XRPD) pattern comprising peaks at 5.9°, 14.2° and 15.9°±0.2°2θ. The XRPD pattern of Pattern 1 of the salt of psilocin and decanoic acid typically further comprises one or more peaks selected from 16.7°, 24.0°, and 24.7°±0.2°2θ. Pattern 1 of the salt of psilocin and decanoic acid may further comprise peaks at 16.7°, 24.0° and 24.7°±0.2°2θ. The XRPD pattern of Pattern 1 of salt of psilocin and decanoic acid may comprise five or more peaks selected from 5.9°, 14.2°, 15.9°, 16.7°, 18.3°, 20.7°, 22.6°, 24.0° and 24.7°±0.2°2θ. The XRPD pattern may comprise seven or more of these peaks. The XRPD pattern may comprise all of these peaks.

The salt of psilocin and decanoic acid may be in the crystalline form designated as decanoic acid Pattern 2, wherein Pattern 2 has an x-ray powder diffraction (XRPD) pattern comprising peaks at 6.4°, 16.9° and 25.2°±0.2°2θ. The XRPD pattern of Pattern 2 of the salt of psilocin and decanoic acid typically further comprises one or more peaks selected from 22.3°, 23.6° and 23.7°±0.2°2θ. Pattern 2 of the salt of psilocin and decanoic acid may further comprise peaks at 22.3°, 23.6°, and 23.7°±0.2°2θ. The XRPD pattern of Pattern 2 of the salt of psilocin and decanoic acid may comprise five or more peaks selected from 6.4°, 16.9°, 17.8°, 19.2°, 19.6°, 22.3°, 23.6°, 23.7° and 25.2°±0.2°2θ. The XRPD pattern may comprise seven or more of these peaks. The XRPD pattern may comprise all of these peaks.

The salt of psilocin and L-lactic acid may be in the crystalline form designated as L-lactic acid Pattern 1, wherein Pattern 1 has an x-ray powder diffraction (XRPD) pattern comprising peaks at 13.4°, 16.8° and 19.5°±0.2°2θ. The XRPD pattern of Pattern 1 of the salt of psilocin and L-lactic acid typically further comprises one or more peaks selected from 16.7°, 23.0° and 24.3°±0.2°2θ. Pattern 1 of the salt of psilocin and L-lactic acid may further comprise peaks at 16.7°, 23.0° and 24.3°±0.2°2θ. The XRPD pattern of Pattern 1 of the salt of psilocin and L-lactic acid may comprise five or more peaks selected from 13.4°, 14.9°, 16.7°, 16.8°, 19.5°, 20.6°, 23.0°, 24.3° and 26.3°±0.2°2θ. The XRPD pattern may comprise seven or more of these peaks. The XRPD pattern may comprise all of these peaks.

The invention is described in more detail by the following Examples. Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

The texts of references cited in this disclosure are herein incorporated by reference in their entireties.

EXAMPLES

Example 1

Preparation Methods

Co-crystals are prepared according to the methods below.

(a) Reactive Crystallisation

Feed solutions, at predefined molar equivalents, each containing psilocin or the co-former in a solvent/solvent system are mixed together and stirred either manually, mechanically or with the use of ultrasound (ultrasonication). Supersaturation is achieved either by evaporation, cooling, anti-solvent addition, spray-drying or freeze drying. The resulting co-crystal is isolated and dried.

(b) Crystallisation

A predefined molar equivalent ratio of psilocin and co-former is either dissolved directly or via mechanical grinding (for example using a pestle and mortar), at a defined temperature, in a solvent/solvent system to yield a clear solution. Supersaturation is achieved either by evaporation, cooling, anti-solvent addition, spray-drying or freeze drying. The resulting co-crystal is isolated and dried.

(c) Slurry or Suspension Mediated Crystallisation

Predefined molar equivalents of psilocin and co-former are suspended in a solvent/solvent system such that a solid fraction remains in excess. The suspension is then stirred either manually, by mechanical means or via the use of ultrasound, or with the use of a shear granulation process. The experiment is either performed isothermally or with a temperature gradient or thermal cycling. The resulting co-crystal is isolated and dried.

(d) Solid State Grinding

Predefined molar equivalents of psilocin and co-former are mixed and ground either manually or mechanically (for example with a ball mill or an extruder). The resultant co-crystal is isolated.

(e) Liquid Assisted Grinding

Predefined molar equivalents of psilocin and co-former are mixed along with a small volume (typically 1:4 volume: weight ratio of total solid) of a solvent/solvent system and ground either manually, mechanically (for example with the use of a ball mill) or with the use of a resonant acoustic mixer. The resultant co-crystal is isolated and dried.

(f) Solid State Mediated

Predefined molar equivalents of psilocin and co-former are mixed together and either exposed to high power laser irradiation or an electrochemical source. The resultant co-crystal is isolated.

(g) Melt Mediated Crystallisation

Predefined molar equivalents of psilocin and co-former are mixed together and simultaneously melted and mixed either directly or mechanically (for example via a hot melt extruder). The resultant molten mixture is then cooled to obtain the resultant co-crystal.

Example 2

Screening

A salt/cocrystal screen of psilocin was performed, with over 140 solvent and non-solvent based experiments carried out using twenty three coformers, namely adenine, ascorbic acid, citric acid, decanoic acid, ethyl maltol, glutathione, isonicotinamide, L-alanine, L-lactic acid, L-phenylalanine, L-proline, L-tryptamine, L-tryptophan, nicotinamide, oleic acid, palmitic acid, propyl gallate, p-coumaric acid, saccharin, stearic acid, theophylline, tyrosine and urea. The experiments were carried out at a scale of approx. 25 mg over a range of stoichiometries from 1:1 to 1:1.1 psilocin:co-former.

A 0.2M stock solution of psilocin was prepared by measuring psilocin (~612.8 mg) into a vial. Acetone (15 mL) was added and the solution was mixed thoroughly prior to use. 0.2 M stock solutions of some of the coformers were prepared in ethanol (decanoic acid, p-coumaric acid, palmitic acid, nicotinamide, propyl gallate, L-tryptamine), acetone (citric acid) or water (L-lactic acid, L-alanine, isonicotinamide, urea). All other coformers were weighed directly into vials as solids.

Precipitation Experiments 0.2 M psilocin stock solution (490 μL) was added to a vial and mixed with the selected coformers (1 eq) either as a solid or as a stock solution (~490 μL) in selected solvents. If precipitation occurred, the solids were isolated via centrifugation, and decantation prior to analysis by XRPD. If no precipitation occurred, the solutions were left to sit overnight prior to addition of cyclohexanone (400 μL) and were left to sit for three days at 20° C.

Slurry Experiments

Psilocin and coformer (either as stock solutions or weighed directly) were mixed in a 1:1.05 Psilocin:coformer ratio and were stirred at 5° C. or 20° C. for 2-6 days. Solids were isolated by filtration/centrifugation and air dried for ~2-5 minutes prior to analysis by XRPD.

Planetary Milling 0.2 M psilocin stock solution (490 μL) was pipetted into HPLC vials and evaporated to dryness. Coformer (either as a stock solution or weighed directly) was added to the vial with three 3 mm steel milling balls. The vials were sealed, and contents milled using a Fritsch planetary mill (Pulverisette 5 classic line). Initially the vials were milled for 30 minutes at a speed of 200 rpm followed a 30 minute resting period. This sequence was repeated 99 times. The resulting milled material was analysed by XRPD.

Solvent (10 μL) was added to samples which did not form unique solids. The vials were milled for a further 40 cycles using the same programme as above (30 minutes at a speed of 200 rpm followed a 30 minute resting period). The resulting milled material was analysed by XRPD.

Based on the outcome of these experiments, co-formers were taken forward for further investigation and analysis. In particular, it was found that the co-formers L-lactic acid, decanoic acid, ethyl maltol, oleic acid, palmitic acid, p-coumaric acid, propyl gallate and stearic acid were able to form crystalline co-crystals with psilocin.

Example 3

Analytical Methods

In the following examples, the following analytical methods were used.

X-Ray Powder Diffraction (XRPD)

XRPD analyses were performed using a Panalytical Empyrean diffractometer equipped with a Cu X-ray tube and a PIXcel 1 D-Medipix3 detector system. The samples were analysed at ambient temperature in transmission mode and held between low density PVC films. The Almac default XRPD program was used (range 3-40°2θ, step size 0.01313°, counting time 20 sec, ~5 min run time), counting time 48 sec, ~10 min run time and counting time 98 sec, ~20 min run time). Samples were spun at 60 rpm during data collection. XRPD patterns were sorted and manipulated using HighScore Plus v4.9 software.

Differential Scanning Calorimetry (DSC)

DSC analyses were carried out on a Perkin Elmer DSC8500 Differential Scanning calorimeter. Accurately weighed samples were placed in crimped aluminium pans (i.e. closed but not gas tight). Each sample was heated under nitrogen at a rate of 10° C./minute to a maximum of 220° C. Indium metal was used as the calibration standard. Temperatures were reported at the transition onset to the nearest 0.01 degree.

Some DSC analyses were carried out on a Mettler Toledo DSC 3+STARe system. The instrument was calibrated for temperature and enthalpy using indium. Nitrogen was used as the protective gas (20 mL/min). Accurately weighed samples were placed in crimped aluminium pans (i.e. closed but not gas tight). Each sample was heated under nitrogen at a rate of 10° C./minute to a maximum of 200° C.

Thermogravimetric Differential Thermal Analysis (TG/DTA)

Thermogravimetric analyses were carried out on a Mettler Toledo TGA/DSC1 STARe. The calibration standards were indium and tin. Samples were placed in an aluminium sample pan, inserted into the TG furnace and accurately weighed. Under a stream of nitrogen at a rate of 10° C./minute, the heat flow signal was stabilised for one minute at 30° C., prior to heating to 300° C.

NMR

NMR analysis was carried out on a Bruker 500 MHz instrument in d6-DMSO or d4-MeOD. Instrumental parameters are listed on the relevant spectrum plots.

Dynamic Vapour Sorption (DVS)

Dynamic Vapour Sorption (DVS) was performed using a Hiden Analytical Instruments IGAsorp Vapour Sorption Balance. Approximately 20-30 mg of sample was placed into a wire-mesh vapour sorption balance pan, loaded into the IGAsorp vapour sorption balance and held at 25° C.±0.1° C. The sample was subjected to a step profile in 10% increments from 0-90% RH, followed by desorption from 90-0% RH and a second sorption cycle form 0-40% RH. The equilibrium criterion was set to 99.0% step completion with a minimum of 60 minutes and a maximum of 5 hours for each increment. The weight change during the sorption cycle was monitored, allowing for the hygroscopic nature of the sample to be determined. The data collection interval was in seconds.

Solubility in FaSSiF

FaSSIF buffer concentrate (1.04125 g) was weighed into a vial. Water (24 mL) was added, and the buffer solution was mixed. FaSSIF powder (~56 mg) was added to the buffer and mixed well. The sample was stirred for 10 minutes until the powder was dissolved. The sample was left to equilibrate for 2 hours prior to use.

The HPLC method used to determine solubility of Psilocin in FaSSIF is outlined below. The retention time of Psilocin was ~6.056 min.

| Parameter | Conditions | | |
|---|---|---|---|
| HPLC System | Waters Alliance 2695 | | |
| Column | Agilent Poroshell eC-C18 120, 4.6 × 100 mm, 2.7 μm | | |
| Oven Temperature | 30° C. | | |
| Flow Rate | 1.0 mL/min | | |
| Injection Volume | 6 μL | | |
| Sample Diluent | 1 mL of 1M HCl in 1000 mL water | | |
| Mobile Phase | Mobile Phase A: 0.05% TFA in water<br>Mobile Phase B: 100% acetonitrile | | |
| | Time (minutes) | Mobile Phase A | Mobile Phase B |
| Gradient | 1.0 | 94 | 6 |
| | 10.00 | 82 | 18 |
| | 15.00 | 25 | 75 |
| | 20.00 | 25 | 75 |
| | 20.10 | 94 | 6 |
| | 25.00 | 94 | 6 |
| Run Time | 25 minutes | | |
| Detector Wavelength | 220 nm | | |

Example 4

Preparation of Co-Crystals (i) Decanoic Acid

An aliquot of Psilocin stock solution (490 μL; 1 mol eq; acetone) was added to a vial and evaporated to dryness under a flow of nitrogen. An aliquot of Decanoic acid stock solution (511 μL; 1.05 mol eq) was added to a vial and evaporated to dryness under a flow of nitrogen. Both solids were mixed and placed in a planetary milling chamber with 3 milling balls. The material was milled for 30 minutes at a speed of 200 rpm followed by a 30 minute resting period for 100 cycles. The sample was analysed by XRPD which indicated a new solid form herein designated decanoic acid Pattern 1, the XRPD characteristics of which are shown in Table 1 below and in FIG. 1.

Separately, decanoic acid (265.62 mg, ~1.05 mol eq) and Psilocin (299.76 mg, 1 mol eq) were charged to a vial. Acetone (2 vols) was added, and a thick white suspension was observed after less than 1 minute. Further acetone (3×1 vol) was added to the mixture (white in colour) and stirred overnight at room temperature. After stirring overnight MTBE (3 vols) was added to aid stirring. Cold MTBE (3 vols) was added to the mixture to aid mobility. The solids were isolated by vacuum filtration and dried for ~2-3 minutes. Liquors were returned to the vial and the solids washed with said liquors. The vial and solids were further washed with cold MTBE (2 vols). The solids were dried for ~15 minutes on the sinter before recovery to a pre weighed vial. A wet weight of ~0.44 g was recorded. Solids were dried in a vacuum oven for 2-3 days after which a dry weight of ~0.44 g was recorded, % recovery=~80%. XRPD analysis revealed the material was composed of a crystalline form herein designated as decanoic acid Pattern 2, the XRPD characteristics of which are shown in Table 2 below and in FIG. 2.

TABLE 1

XRPD peak list for decanoic acid Pattern 1

| Pos. [°2θ] | d-spacing [Å] | Rel. Int. [%] |
|---|---|---|
| 3.4614 | 25.52642 | 1.57 |
| 5.8705 | 15.05518 | 100 |
| 9.1405 | 9.67528 | 4.78 |
| 10.5057 | 8.4208 | 2.02 |
| 11.2462 | 7.868 | 4.28 |
| 11.7688 | 7.51355 | 1.72 |
| 11.9346 | 7.41563 | 9.41 |
| 12.5245 | 7.06764 | 5.22 |
| 14.1598 | 6.2549 | 95.64 |
| 14.3541 | 6.17066 | 22.06 |
| 14.6967 | 6.02758 | 2.3 |
| 15.4919 | 5.71992 | 4.21 |
| 15.9007 | 5.57379 | 79.31 |
| 16.3199 | 5.43156 | 3.3 |
| 16.6989 | 5.3091 | 55.73 |
| 17.2937 | 5.12784 | 1.81 |
| 17.594 | 5.03682 | 3.43 |
| 17.7015 | 5.0106 | 17.98 |
| 18.3109 | 4.8452 | 30.32 |
| 18.8433 | 4.7056 | 2.32 |
| 18.9761 | 4.67683 | 10.56 |
| 19.3191 | 4.59455 | 9.76 |
| 19.7186 | 4.50237 | 8.95 |
| 20.0563 | 4.42732 | 12.1 |
| 20.7056 | 4.28993 | 24.95 |
| 21.0198 | 4.2265 | 17.36 |
| 22.0547 | 4.03047 | 23.4 |
| 22.624 | 3.93031 | 40.52 |

TABLE 1-continued

XRPD peak list for decanoic acid Pattern 1

| Pos. [°2θ] | d-spacing [Å] | Rel. Int. [%] |
|---|---|---|
| 22.9237 | 3.87961 | 14.26 |
| 23.5849 | 3.77232 | 6.1 |
| 23.7546 | 3.74264 | 1.74 |
| 24.017 | 3.70542 | 51.89 |
| 24.5738 | 3.6227 | 12.25 |
| 24.713 | 3.60262 | 71.71 |
| 25.0459 | 3.55253 | 1.82 |
| 25.7654 | 3.4578 | 2.55 |
| 26.1087 | 3.41312 | 7.42 |
| 26.6081 | 3.3474 | 1.95 |
| 26.7461 | 3.33319 | 2.87 |
| 27.7826 | 3.21116 | 0.97 |
| 28.8444 | 3.09532 | 5.73 |
| 29.3005 | 3.04817 | 1.89 |
| 29.703 | 3.00778 | 2.94 |
| 29.8936 | 2.98903 | 9.61 |
| 30.2594 | 2.95373 | 1.24 |
| 30.5447 | 2.92436 | 1.27 |
| 30.805 | 2.90265 | 4.98 |
| 31.1566 | 2.87069 | 1.35 |
| 31.6995 | 2.82041 | 0.54 |
| 32.1086 | 2.78771 | 2.35 |
| 32.6458 | 2.74079 | 0.52 |
| 33.1356 | 2.70138 | 0.92 |
| 33.4144 | 2.6817 | 1.31 |
| 33.9058 | 2.64395 | 4.39 |
| 34.3907 | 2.60777 | 0.54 |
| 34.8881 | 2.56959 | 1.01 |
| 35.191 | 2.55028 | 1.05 |
| 35.8807 | 2.50282 | 1.28 |
| 36.0884 | 2.48683 | 1.08 |
| 36.3488 | 2.46962 | 0.97 |
| 38.2333 | 2.35406 | 7.98 |
| 38.5712 | 2.33228 | 1.91 |
| 39.5194 | 2.28037 | 1.26 |

Further analysis of decanoic acid Pattern 1 revealed the following results.

The sample was analysed by 1H NMR spectroscopy and the spectrum conformed to the molecular structure. The stoichiometry was shown to be 1:~1.2 (Psilocin:decanoic acid).

TABLE 2

XRPD peak list for decanoic acid Pattern 2

| Pos. [°2θ] | d-spacing [Å] | Rel. Int. [%] |
|---|---|---|
| 6.379 | 13.85611 | 100 |
| 9.9895 | 8.85476 | 8.85 |
| 11.7158 | 7.55366 | 6.96 |
| 12.4171 | 7.12267 | 0.45 |
| 12.6615 | 6.99151 | 2.37 |
| 12.7932 | 6.91983 | 2.8 |
| 13.0976 | 6.75409 | 0.35 |
| 13.6801 | 6.47312 | 0.75 |
| 14.0131 | 6.32004 | 3.66 |
| 14.4465 | 6.13139 | 5.73 |
| 14.6246 | 6.05713 | 1.51 |
| 16.2915 | 5.43646 | 0.41 |
| 16.6698 | 5.31831 | 1.98 |
| 16.9125 | 5.24255 | 43.42 |
| 17.3658 | 5.1067 | 11.21 |
| 17.7645 | 4.99297 | 14.42 |
| 18.1207 | 4.89158 | 8.85 |
| 18.2012 | 4.88223 | 6.52 |
| 18.3893 | 4.82073 | 3.2 |
| 19.2353 | 4.61056 | 16.76 |
| 19.6362 | 4.51734 | 15.57 |
| 20.0723 | 4.42017 | 0.89 |
| 20.6023 | 4.30764 | 12.39 |
| 21.1389 | 4.19948 | 1.31 |

TABLE 2-continued

| XRPD peak list for decanoic acid Pattern 2 | | |
|---|---|---|
| Pos. [°2θ] | d-spacing [Å] | Rel. Int. [%] |
| 21.4 | 4.14883 | 3.29 |
| 21.9574 | 4.04475 | 13.8 |
| 22.2857 | 3.98591 | 17.75 |
| 22.4892 | 3.9503 | 12.72 |
| 23.2448 | 3.82356 | 0.78 |
| 23.5557 | 3.77381 | 28.25 |
| 23.6562 | 3.758 | 17.87 |
| 23.671 | 3.765 | 22.53 |
| 24.0086 | 3.70362 | 3.28 |
| 24.7619 | 3.59263 | 11.81 |
| 25.1725 | 3.53495 | 33.06 |
| 25.4876 | 3.49196 | 3.71 |
| 25.7634 | 3.45521 | 12.62 |
| 26.0169 | 3.42211 | 11.53 |
| 26.2073 | 3.39767 | 1.11 |
| 26.4771 | 3.36366 | 5.89 |
| 26.7785 | 3.32648 | 0.32 |
| 27.0303 | 3.29607 | 3.4 |
| 27.5787 | 3.23176 | 0.23 |
| 27.9502 | 3.18964 | 0.67 |
| 28.2349 | 3.15812 | 0.9 |
| 28.5842 | 3.12032 | 2.87 |
| 28.9333 | 3.08346 | 0.32 |
| 29.1376 | 3.0623 | 3.62 |
| 29.4954 | 3.02597 | 1.85 |
| 29.8637 | 2.98948 | 0.87 |
| 30.1698 | 2.95985 | 0.77 |
| 30.3176 | 2.94575 | 0.79 |
| 31.068 | 2.87629 | 0.22 |
| 31.3539 | 2.85071 | 1.58 |
| 32.0428 | 2.79098 | 1.56 |
| 32.3718 | 2.76336 | 0.97 |
| 32.6933 | 2.73691 | 1.51 |
| 32.7657 | 2.73103 | 1.57 |
| 33.0101 | 2.71137 | 1.06 |
| 33.1002 | 2.70419 | 4.71 |
| 33.1923 | 2.7036 | 2.21 |
| 33.8535 | 2.64572 | 0.43 |
| 34.267 | 2.61473 | 0.36 |
| 34.7885 | 2.57672 | 0.69 |
| 35.0526 | 2.55792 | 0.42 |
| 35.7665 | 2.50848 | 1.29 |
| 35.9631 | 2.49522 | 0.51 |
| 36.151 | 2.48267 | 0.53 |
| 36.7362 | 2.44446 | 2.09 |
| 37.2562 | 2.41152 | 1.04 |
| 37.8704 | 2.37381 | 0.5 |
| 38.0588 | 2.3625 | 0.54 |
| 38.2043 | 2.35383 | 1.07 |
| 38.3648 | 2.34435 | 1.59 |
| 38.6457 | 2.32796 | 1.2 |
| 38.7929 | 2.31946 | 1.13 |
| 39.1327 | 2.3001 | 0.6 |
| 39.6327 | 2.27222 | 0.91 |
| 39.8478 | 2.26045 | 0.88 |

Further analysis of decanoic acid Pattern 2 revealed the following results:

- The 1H-NMR spectrum conformed to the molecular structure with negligible residual solvents observed. The stoichiometry was determined to be ~1:1 (Psilocin: Decanoic acid).
- DSC analysis showed an endotherm with an onset temperature of ~90° C., concordant with TG/DTA data.
- DVS analysis showed that the total weight change observed between ambient (i.e. 40% RH) and 80% RH was ~0.02% w/w. XRPD analysis of the material post DVS analysis indicated that no change in physical form had occurred.
- The co-crystal was stressed at 40° C./75% RH and 20° C./60% RH for 7 days. No change in form was observed by XRPD.
- HPLC solubility was estimated in FaSSIF at ~37° C. The material had solubility of ~3.18 mg/mL after 15 mins and ~2.99 mg/mL after 22 hours.

(ii) Ethyl Maltol

Psilocin (~100 mg, 1 mol eq) and ethyl maltol (44.344 mg; ~1.01 mol eq) were charged to a vial. Acetone (300 μL) was added, and the suspension was stirred at 20° C. The bulk sample was isolated by centrifugation and decantation. Acetone (100 uL) was added to the isolated solids which were slurried to attempt to remove excess ethyl maltol. The solids were isolated and the material was dried under a flow of nitrogen overnight. The product was analysed by XRPD and was shown to be composed of a new crystalline form herein designated as ethyl maltol Pattern 1, the XRPD characteristics of which are shown in Table 3 below and in FIG. 3.

TABLE 3

| XRPD peak list for ethyl maltol Pattern 1 | | |
|---|---|---|
| Pos. [°2θ] | d-spacing [Å] | Rel. Int. [%] |
| 5.004 | 17.65995 | 100 |
| 6.5111 | 13.57543 | 1.54 |
| 9.2064 | 9.60616 | 20.52 |
| 9.4638 | 9.34546 | 24.03 |
| 10.0364 | 8.81352 | 5.7 |
| 10.9637 | 8.07008 | 4.49 |
| 11.4096 | 7.74922 | 1.84 |
| 11.6729 | 7.58128 | 3.42 |
| 12.0265 | 7.35918 | 5.48 |
| 12.4571 | 7.10576 | 2.81 |
| 13.1443 | 6.73575 | 12.83 |
| 13.2957 | 6.65391 | 2.46 |
| 13.6039 | 6.50923 | 2.39 |
| 13.8681 | 6.38579 | 12.02 |
| 14.2498 | 6.2156 | 7.39 |
| 14.8361 | 5.97127 | 25.36 |
| 15.065 | 5.88106 | 72.99 |
| 15.5357 | 5.70389 | 12.54 |
| 15.7431 | 5.62457 | 2.68 |
| 15.9745 | 5.5482 | 3.81 |
| 16.4074 | 5.40278 | 15.89 |
| 17.0009 | 5.21546 | 4.16 |
| 17.3478 | 5.10772 | 0.66 |
| 17.8772 | 4.95763 | 4.9 |
| 18.0427 | 4.9166 | 63.32 |
| 18.4795 | 4.80138 | 32.89 |
| 18.9912 | 4.66927 | 2.34 |
| 19.3314 | 4.59167 | 3.96 |
| 20.2186 | 4.39215 | 24.73 |
| 20.672 | 4.29327 | 1.87 |
| 21.1402 | 4.2027 | 22.13 |
| 21.3721 | 4.15763 | 22.1 |
| 21.7205 | 4.09172 | 35.91 |
| 22.196 | 4.00513 | 16.91 |
| 22.3316 | 3.98111 | 12.19 |
| 22.6084 | 3.93299 | 9.16 |
| 23.1506 | 3.84208 | 2.09 |
| 23.8433 | 3.73202 | 4.9 |
| 24.142 | 3.68652 | 5.05 |
| 24.4855 | 3.63257 | 1.56 |
| 24.808 | 3.58904 | 4 |
| 25.1348 | 3.54017 | 2.9 |
| 25.2854 | 3.52234 | 4.79 |
| 25.5002 | 3.49027 | 1.4 |
| 25.7263 | 3.46011 | 2.86 |
| 26.1157 | 3.41222 | 52.19 |
| 26.4864 | 3.36529 | 10.31 |
| 26.7275 | 3.33548 | 37.69 |
| 27.4468 | 3.24698 | 1.97 |
| 27.8085 | 3.20823 | 16.44 |
| 28.2556 | 3.15847 | 5.98 |
| 28.6453 | 3.11638 | 1.87 |
| 29.0717 | 3.07164 | 2.2 |
| 29.4878 | 3.02672 | 2.43 |
| 29.6451 | 3.01352 | 5.67 |

TABLE 3-continued

| XRPD peak list for ethyl maltol Pattern 1 | | |
|---|---|---|
| Pos. [°2θ] | d-spacing [Å] | Rel. Int. [%] |
| 29.9676 | 2.98182 | 3.43 |
| 30.5251 | 2.92862 | 3.82 |
| 30.7756 | 2.90535 | 4.43 |
| 31.7711 | 2.81655 | 1.63 |
| 32.2859 | 2.77051 | 1.56 |
| 32.5396 | 2.74949 | 0.52 |
| 33.6214 | 2.66566 | 1.49 |
| 34.4225 | 2.60544 | 0.99 |
| 35.9109 | 2.49872 | 1.44 |
| 36.2328 | 2.47725 | 0.86 |
| 36.6667 | 2.45096 | 2.24 |
| 37.1768 | 2.41849 | 1.37 |
| 37.9165 | 2.373 | 0.97 |
| 38.505 | 2.33614 | 0.83 |
| 39.0157 | 2.30864 | 1.48 |
| 39.6973 | 2.26868 | 2.31 |

Further analysis of ethyl maltol Pattern 1 gave the following results.

The stoichiometry was determined to be 1:~0.8 (psilocin: ethyl maltol) by $^1$H-NMR spectroscopy.

DSC analysis (FIG. 68) showed two endotherms with onset temperatures of ~86° C. and ~131° C., concordant with the TG/DTA data.

A sample of the material was stressed at 40° C./75% RH for 6 days to ascertain its stability. No change in physical form was observed.

(iii) L-Lactic Acid

L-Lactic acid (23.65 mg, ~1.05 mol eq.) and Psilocin (49.36 mg, 1 mol eq.) were charged to a vial. Acetone (2 vols) was added, and some of the mixture began to dissolve. Further acetone (2×1 vol) was added. After ~10 minutes the mixture began to precipitate. After 30 minutes a thick suspension was observed which was not mobile. MTBE (2×1 vol) was added to aid stirring. The sample was stirred overnight at room temperature. The isolated product was used as a seed crystal in the following experiment.

L-Lactic acid (140.31 mg, ~1.05 mol eq.) and Psilocin (301.26 mg, 1 mol eq.) were charged to a vial. Acetone (2 vols) was added, and immediate precipitation was observed. Further acetone (1 vol) was charged to the mixture (off white in colour) and stirred overnight at room temperature. After stirring overnight, MTBE (4 vols) was added to aid stirring as the suspension was very thick. The suspension was seeded with the product of the experiment above and stirred for 3 days. Cold MTBE (in total 11 vols) was charged to the mixture to aid mobility. The solids were isolated by vacuum filtration and dried for ~10-15 minutes. The vial was washed with some of the MTBE (11 vols) to improve recovery of solids. The solids were dried for ~15 minutes on the sinter before recovery to a pre weighed vial. A wet weight of ~0.35 g was recorded. The solids were dried in a vacuum oven overnight after which a dry weight of ~0.35 g was recorded, % recovery=~81%. XRPD analysis showed that the product was composed of the crystalline form herein designated as L-lactic acid Pattern 1, the XRPD characteristics of which are shown in Table 4 below and FIG. 4.

TABLE 4

| XRPD peak list for L-lactic acid Pattern 1 | | |
|---|---|---|
| Pos. [°2θ] | d-spacing [Å] | Rel. Int. [%] |
| 8.3193 | 10.62835 | 4.19 |
| 8.8375 | 10.00623 | 2.08 |
| 11.0253 | 8.02515 | 29.81 |
| 13.378 | 6.61862 | 96.24 |
| 14.2359 | 6.22162 | 14.26 |
| 14.9154 | 5.93969 | 46.65 |
| 16.6636 | 5.32029 | 54.66 |
| 16.7893 | 5.28073 | 88.58 |
| 17.7347 | 5.00129 | 8.81 |
| 19.5194 | 4.54787 | 100 |
| 20.1353 | 4.40648 | 9.64 |
| 20.281 | 4.37877 | 21.67 |
| 20.5943 | 4.31286 | 37.79 |
| 20.742 | 4.27893 | 7.84 |
| 22.1529 | 4.01282 | 16.97 |
| 22.5459 | 3.94375 | 11.16 |
| 22.8243 | 3.89627 | 17.6 |
| 22.9935 | 3.86798 | 52.25 |
| 23.6429 | 3.7632 | 3.5 |
| 24.2634 | 3.66834 | 76.71 |
| 24.4357 | 3.64286 | 32.75 |
| 26.2592 | 3.39389 | 38.88 |
| 26.5031 | 3.3632 | 7.3 |
| 26.952 | 3.3082 | 2.88 |
| 28.6544 | 3.11541 | 5.22 |
| 29.0552 | 3.07334 | 15.61 |
| 30.0972 | 2.96928 | 9.38 |
| 30.2483 | 2.95234 | 3.07 |
| 30.4482 | 2.93341 | 2.11 |
| 30.7124 | 2.90878 | 0.73 |
| 30.9051 | 2.89108 | 0.71 |
| 31.2834 | 2.85697 | 0.36 |
| 31.8682 | 2.80819 | 6.8 |
| 32.0907 | 2.78692 | 3.47 |
| 32.6444 | 2.74317 | 1.81 |
| 32.9951 | 2.71481 | 3.46 |
| 33.336 | 2.68782 | 5.28 |
| 33.5821 | 2.66648 | 1.38 |
| 33.9591 | 2.63992 | 10.26 |
| 34.5799 | 2.59393 | 1.15 |
| 35.0598 | 2.55741 | 0.9 |
| 35.3693 | 2.53783 | 3.09 |
| 35.5809 | 2.52114 | 1.42 |
| 36.666 | 2.44897 | 1.74 |
| 36.9137 | 2.43512 | 7.92 |
| 37.603 | 2.39206 | 3.39 |
| 37.9295 | 2.37221 | 1.86 |
| 38.9574 | 2.31196 | 4.09 |
| 39.2846 | 2.29345 | 5.17 |
| 39.65 | 2.27128 | 2.5 |

Further analysis of L-lactic acid Pattern 1 gave the following results.

The sample was analysed by 1H NMR spectroscopy and the spectrum conformed to the molecular structure with negligible residual solvents observed. The stoichiometry was determined to be ~1:1 (Psilocin:L-lactic acid).

The sample was analysed by TG/DTA. Weight loss was not observed until temperatures greater than 200° C. which was likely associated with decomposition. An endotherm was observed with an onset temperature of ~151° C., which is concordant with DSC analysis.

DVS analysis showed that the total weight gain observed between ambient (i.e., 40% RH) and 80% RH was ~0.03% w/w. XRPD analysis was performed on the sample post DVS and no change in form was observed.

The co-crystal was stressed at 40° C./75% RH and 20° C./60% RH for 7 days. No change in form was observed.

Solubility was estimated in FaSSIF by aliquot addition at ~20° C. The material had solubility of 90-107 mg/mL. Due to the high solubility of the crystalline form HPLC solubility was not carried out for this sample.

(iv) Oleic Acid

Psilocin stock solution (490 μL; 1 mol eq; acetone) and oleic acid (~36.4 μL; 1.05 mol eq) were added to a vial. The mixture was stirred at 20° C. for 2 days and remained as a solution. Heptane (500 μL) was added to aid crystallisation and the solution was stirred at 5° C. After 8 days no precipitation of solids had occurred. The solution was evaporated under nitrogen to half volume and a suspension formed. The suspension was stirred at 5° C. for a further day prior to isolation by centrifugation and decantation. The recovered solids were used as a seed crystal in the following experiment.

Psilocin (~100 mg, 1 mol eq) and oleic acid (182 μL; 1.05 mol eq) were charged to a vial with acetone (100 μL). The mixture was stirred at 5° C. After 1 day Heptane (100 μL) was added and the sample stirred at 5° C. After 3 days the sample was seeded with the co-crystal obtained in the experiment above and stirred at 5° C. for a further 4 days prior to isolation by centrifugation and decantation. XRPD analysis confirmed the material was composed of a crystalline form herein designated as oleic acid Pattern 1, the XRPD characteristics of which are shown in Table 5 below and in FIG. 5.

TABLE 5

XRPD peak list of oleic acid Pattern 1

| Pos. [°2θ] | d-spacing [Å] | Rel. Int. [%] |
|---|---|---|
| 4.6204 | 19.12541 | 100 |
| 9.2631 | 9.54745 | 6.44 |
| 9.5707 | 9.24128 | 6.28 |
| 11.6013 | 7.62161 | 1.6 |
| 11.6861 | 7.57278 | 4.17 |
| 13.9181 | 6.36298 | 4.78 |
| 14.1343 | 6.26613 | 1.77 |
| 14.3974 | 6.15221 | 3.96 |
| 14.7461 | 6.00252 | 0.62 |
| 15.0453 | 5.88383 | 0.71 |
| 15.6981 | 5.64524 | 4.84 |
| 15.8841 | 5.57956 | 23.34 |
| 17.5509 | 5.04908 | 1.62 |
| 17.6552 | 5.02363 | 5.48 |
| 18.0353 | 4.91861 | 7.33 |
| 18.2183 | 4.86962 | 14.14 |
| 18.475 | 4.80254 | 14.79 |
| 18.5983 | 4.77096 | 8.95 |
| 18.7183 | 4.73672 | 3.46 |
| 18.9477 | 4.68377 | 5.91 |
| 19.1512 | 4.63445 | 5.02 |
| 19.4073 | 4.57388 | 23.49 |
| 19.5631 | 4.53781 | 16.08 |
| 20.3761 | 4.35855 | 17.22 |
| 21.1193 | 4.20681 | 15.62 |
| 21.4545 | 4.13841 | 1.74 |
| 21.615 | 4.10804 | 1.25 |
| 21.7776 | 4.08111 | 4.64 |
| 21.9206 | 4.05481 | 15.53 |
| 22.1442 | 4.01437 | 15.13 |
| 22.7901 | 3.90205 | 3.66 |
| 23.0764 | 3.85428 | 5.12 |
| 23.33 | 3.81295 | 7.01 |
| 23.4971 | 3.78622 | 19.44 |
| 23.6844 | 3.75359 | 1.54 |
| 24.3441 | 3.65333 | 10.44 |
| 24.4574 | 3.63969 | 32 |
| 24.9686 | 3.56337 | 0.89 |
| 25.6633 | 3.47132 | 12.02 |
| 25.9263 | 3.43671 | 5.13 |
| 26.2468 | 3.39547 | 5.81 |
| 26.9941 | 3.30314 | 2.24 |
| 27.2013 | 3.27573 | 0.92 |
| 28.1279 | 3.16989 | 0.72 |
| 28.4198 | 3.13799 | 0.82 |
| 28.5717 | 3.12424 | 3.04 |

TABLE 5-continued

XRPD peak list of oleic acid Pattern 1

| Pos. [°2θ] | d-spacing [Å] | Rel. Int. [%] |
|---|---|---|
| 29.0194 | 3.07706 | 2.91 |
| 29.2934 | 3.0489 | 1.41 |
| 29.7466 | 3.00347 | 0.98 |
| 30.397 | 2.94067 | 1.34 |
| 32.6424 | 2.74107 | 0.62 |
| 32.8512 | 2.72637 | 1.83 |
| 33.0437 | 2.70869 | 0.78 |
| 33.6724 | 2.66174 | 1.06 |
| 33.8755 | 2.64406 | 0.59 |
| 34.4181 | 2.6036 | 0.6 |
| 35.8079 | 2.50774 | 0.99 |
| 36.359 | 2.46895 | 0.54 |
| 36.5493 | 2.45856 | 1.44 |
| 38.8452 | 2.31838 | 0.6 |

Further analysis of oleic acid Pattern 1 revealed the following results.

The sample was analysed by 1H NMR spectroscopy and the spectrum conformed to the molecular structure. The stoichiometry was shown to be 1:~1.1 (Psilocin:oleic acid).

DSC analysis showed an endotherm with an onset temperature of ~56° C. and was concordant with the TG/DTA data.

(v) Palmitic Acid

Psilocin (~60 mg, 1 mol eq) and palmitic acid (75.976 mg; 1.01 mol eq.) were charged to a vial with THF (20 μL) and four milling balls. The material was subjected to a program of planetary milling for 30 minutes at a speed of 400 rpm followed by a 30 minute resting period. This sequence was repeated 19 times. The sample was dried under a flow of nitrogen overnight. XRPD analysis of the product revealed a new crystalline form, herein designated as palmitic acid Pattern 1, the XRPD characteristics of which are shown in Table 6 below and in FIG. 6.

TABLE 6

XRPD peak list for palmitic acid Pattern 1

| Pos. [°2θ] | d-spacing [Å] | Rel. Int. [%] |
|---|---|---|
| 4.6993 | 18.80462 | 100 |
| 9.2813 | 9.52875 | 5.68 |
| 9.4299 | 9.37893 | 6.7 |
| 11.3802 | 7.7756 | 2.09 |
| 11.7 | 7.56384 | 5.98 |
| 13.728 | 6.45063 | 7.87 |
| 14.156 | 6.2514 | 6.56 |
| 14.3664 | 6.16539 | 35.35 |
| 14.6826 | 6.03332 | 24.38 |
| 14.8763 | 5.95521 | 11.05 |
| 15.5367 | 5.70353 | 5.52 |
| 16.0614 | 5.51837 | 29.58 |
| 16.9616 | 5.22746 | 23.94 |
| 17.8681 | 4.96426 | 15.34 |
| 18.5333 | 4.78755 | 5.49 |
| 18.9079 | 4.69354 | 14.44 |
| 19.4105 | 4.57313 | 7.02 |
| 19.7603 | 4.49295 | 13.66 |
| 20.2532 | 4.38472 | 28.07 |
| 21.224 | 4.1863 | 17.67 |
| 21.5213 | 4.12914 | 16.93 |
| 22.8693 | 3.88871 | 25.81 |
| 23.0292 | 3.86207 | 47.1 |
| 23.8387 | 3.73273 | 37.19 |
| 24.0686 | 3.69453 | 4.48 |
| 24.7701 | 3.59146 | 0.67 |
| 25.2512 | 3.52703 | 1.72 |

TABLE 6-continued

| XRPD peak list for palmitic acid Pattern 1 | | |
|---|---|---|
| Pos. [°2θ] | d-spacing [Å] | Rel. Int. [%] |
| 26.0544 | 3.41727 | 3.53 |
| 26.3021 | 3.38845 | 6.03 |
| 27.0601 | 3.29523 | 19.7 |
| 27.3036 | 3.26369 | 1.41 |
| 27.7353 | 3.21386 | 0.91 |
| 28.202 | 3.16435 | 2.11 |
| 28.6123 | 3.11732 | 0.95 |
| 29.1168 | 3.06445 | 0.91 |
| 29.6474 | 3.01329 | 2.25 |
| 29.915 | 2.98695 | 1.9 |
| 30.7572 | 2.90464 | 0.9 |
| 31.3446 | 2.8539 | 2.8 |
| 31.841 | 2.81052 | 2.52 |
| 33.5111 | 2.67418 | 0.77 |
| 34.8605 | 2.5737 | 1.17 |
| 36.8029 | 2.4422 | 0.8 |
| 38.4376 | 2.34202 | 1.38 |
| 38.8113 | 2.32032 | 3.04 |
| 39.4011 | 2.28694 | 1.69 |

Further analysis of palmitic acid Pattern 1 gave the following results.

The sample was analysed by 1H NMR spectroscopy and conformed to the molecular structure. No solvent was detected in the sample. The stoichiometry was estimated to be 1:~1 Psilocin:Palmitic acid.

DSC analysis showed an endotherm with an onset temperature of ~82° C., concordant with the TG/DTA data.

(vi) p-Coumaric Acid

Aliquots of Psilocin stock solution (490 µL; 1 mol eq; acetone) and p-coumaric acid stock solution (518 µL; 1.05 mol eq; ethanol) were added to a vial and the solution was stirred at 20° C. for 2 days. After two days the sample remained as a solution. Heptane (500 µL) was added to aid crystallisation and the solution was stirred at 5° C. for 14 days. The experiment remained as a solution and was evaporated to half volume under nitrogen which resulted in an oil/solution. MTBE (200 µL) was added, and the sample was stirred at 5° C. for a further 3 days prior to isolation by centrifugation and decantation. The sample was analysed by XRPD and was shown to be composed of a new solid form, herein designated p-coumaric acid Pattern 1, the XRPD characteristics of which are shown in Table 7 below and FIG. 7.

TABLE 7

| XRPD peak list for p-coumaric acid Pattern 1 | | |
|---|---|---|
| Pos. [°2θ] | d-spacing [Å] | Rel. Int. [%] |
| 5.4317 | 16.27055 | 100 |
| 6.4709 | 13.65963 | 17.23 |
| 7.0182 | 12.59551 | 11.73 |
| 9.149 | 9.65824 | 1.36 |
| 10.4324 | 8.47284 | 0.9 |
| 10.8721 | 8.13785 | 5.02 |
| 11.0147 | 8.03281 | 7.17 |
| 11.8452 | 7.46523 | 1.5 |
| 13.3205 | 6.64708 | 1.28 |
| 14.0711 | 6.29414 | 4.15 |
| 15.046 | 5.88843 | 8.07 |
| 15.3377 | 5.7723 | 2.62 |
| 15.5094 | 5.7135 | 35.45 |
| 15.7688 | 5.6201 | 5.72 |
| 16.1732 | 5.47593 | 3.09 |
| 16.3708 | 5.41478 | 21.82 |
| 16.9837 | 5.22072 | 8.39 |

TABLE 7-continued

| XRPD peak list for p-coumaric acid Pattern 1 | | |
|---|---|---|
| Pos. [°2θ] | d-spacing [Å] | Rel. Int. [%] |
| 17.3186 | 5.12051 | 11.84 |
| 17.6161 | 5.0347 | 4.83 |
| 17.8763 | 4.962 | 9.39 |
| 18.2141 | 4.87073 | 8.54 |
| 18.3998 | 4.82199 | 7.83 |
| 18.7925 | 4.71819 | 3.93 |
| 19.0122 | 4.66804 | 7.3 |
| 19.2826 | 4.60317 | 8.64 |
| 19.4937 | 4.55003 | 2.45 |
| 19.6999 | 4.50659 | 21.36 |
| 19.9754 | 4.44507 | 2.61 |
| 20.2771 | 4.37959 | 6.25 |
| 20.5183 | 4.32865 | 28.52 |
| 20.9791 | 4.23111 | 1.69 |
| 21.1955 | 4.19186 | 5.49 |
| 21.4696 | 4.13896 | 3.75 |
| 21.8775 | 4.06271 | 12.27 |
| 22.1263 | 4.01426 | 1.49 |
| 22.4379 | 3.9592 | 2.25 |
| 22.5772 | 3.9351 | 3.22 |
| 22.8391 | 3.89378 | 11.43 |
| 23.1904 | 3.83559 | 1.78 |
| 23.7309 | 3.74944 | 8.78 |
| 24.2895 | 3.66446 | 2.75 |
| 24.5481 | 3.62644 | 6.17 |
| 25.2497 | 3.52433 | 1.66 |
| 25.5613 | 3.48206 | 1.72 |
| 26.1822 | 3.40369 | 5.62 |
| 26.5382 | 3.35884 | 3.59 |
| 27.5391 | 3.239 | 2.71 |
| 27.9658 | 3.19054 | 2.99 |
| 28.5903 | 3.11967 | 1.4 |
| 29.2998 | 3.04572 | 2.08 |
| 29.518 | 3.0262 | 4.03 |
| 30.9973 | 2.88508 | 1.44 |
| 33.4545 | 2.67857 | 1.28 |

Further analysis of p-coumaric acid Pattern 1 revealed the following results.

The sample was analysed by 1H NMR spectroscopy and conformed to the molecular structure. The stoichiometry was shown to be 1:~1 (Psilocin: p-coumaric acid).

(vii) Propyl Gallate

Psilocin (303.5 mg, 1 mol eq.) and propyl gallate (327.5 mg, ~1.05 mol eq) were charged to a vial. Acetone (3 vols) was added with some solids dissolving. Precipitation started to occur after <1 minute. Further acetone (2 vol) was added to the mixture (off white in colour) and stirred overnight at room temperature. Cold MTBE (total 10 vols) was charged to the mixture to aid mobility. The bulk sample was isolated by vacuum filtration and dried for ~10-15 minutes. The vial was washed with some of the MTBE (10 vols) to improve recovery of solids. The mixture filtered well, and the solids were dried for ~15 minutes on the sinter before recovery to a pre weighed vial. A wet weight of ~0.38 g was recorded. The solids were dried in a vacuum oven overnight. A dry weight of ~0.39 g was recorded. The % recovery=~63%. XRPD analysis of the product revealed the sample was composed of a crystalline form herein designated as propyl gallate Pattern 1, the XRPD characteristics of which are shown in Table 8 below and in FIG. 8.

TABLE 8

| XRPD peak list for propyl gallate Pattern 1 | | |
|---|---|---|
| Pos. [°2θ] | d-spacing [Å] | Rel. Int. [%] |
| 5.0235 | 17.59156 | 10.27 |
| 7.6788 | 11.51332 | 11.26 |
| 8.8478 | 9.99465 | 61.02 |
| 9.5199 | 9.29045 | 8.85 |
| 10.0839 | 8.77211 | 15.76 |
| 11.3768 | 7.77795 | 33.13 |
| 11.8392 | 7.47522 | 20.55 |
| 12.1878 | 7.26214 | 3.95 |
| 12.3283 | 7.1797 | 7.34 |
| 12.5757 | 7.03901 | 100 |
| 13.1934 | 6.71083 | 29.38 |
| 13.9121 | 6.36572 | 17.47 |
| 14.3475 | 6.17348 | 36.12 |
| 14.7326 | 6.01295 | 74.35 |
| 15.4074 | 5.7511 | 7.53 |
| 15.8306 | 5.59831 | 63.72 |
| 16.2782 | 5.44535 | 4.22 |
| 16.5942 | 5.34237 | 8.2 |
| 17.0028 | 5.2149 | 10.57 |
| 17.5474 | 5.05427 | 16.64 |
| 17.7591 | 4.99449 | 11.75 |
| 18.2465 | 4.86215 | 2.33 |
| 18.5909 | 4.77285 | 68.59 |
| 18.7471 | 4.73344 | 21.24 |
| 19.2445 | 4.6122 | 59.49 |
| 19.7945 | 4.48528 | 33.93 |
| 20.2599 | 4.38327 | 1.15 |
| 20.6014 | 4.31138 | 1.77 |
| 20.7998 | 4.2707 | 5 |
| 21.1005 | 4.21053 | 17.83 |
| 21.9529 | 4.04893 | 40.36 |
| 22.1134 | 4.0199 | 18.54 |
| 22.3755 | 3.9734 | 21.76 |
| 22.5707 | 3.93948 | 72.04 |
| 22.8711 | 3.88841 | 21.22 |
| 23.0217 | 3.86331 | 25.78 |
| 23.2052 | 3.83317 | 5.26 |
| 23.5712 | 3.77448 | 10.23 |
| 23.9976 | 3.70837 | 33.23 |
| 24.2615 | 3.66863 | 21.8 |
| 24.5308 | 3.62895 | 13.31 |
| 24.7985 | 3.59039 | 10.67 |
| 25.0071 | 3.56091 | 7.47 |
| 25.1945 | 3.53192 | 9 |
| 25.31 | 3.51898 | 10.33 |
| 25.6105 | 3.47836 | 2.61 |
| 26.0839 | 3.41347 | 9.21 |
| 26.1793 | 3.40407 | 9.39 |
| 26.5479 | 3.35763 | 6.32 |
| 26.8904 | 3.31565 | 32.66 |
| 27.8996 | 3.19796 | 16.51 |
| 28.1766 | 3.16452 | 1.3 |
| 28.4479 | 3.13496 | 0.82 |
| 28.9159 | 3.08783 | 3.66 |
| 29.0663 | 3.06966 | 3.28 |
| 29.2398 | 3.05183 | 3.6 |
| 29.4091 | 3.03716 | 15.6 |
| 29.713 | 3.00678 | 3.89 |
| 30.0861 | 2.96789 | 1.27 |
| 30.1837 | 2.95851 | 3.39 |
| 30.2815 | 2.95162 | 4.8 |
| 30.897 | 2.89421 | 1.54 |
| 31.1818 | 2.86605 | 2.47 |
| 31.3485 | 2.85355 | 9.44 |
| 31.7459 | 2.81639 | 0.46 |
| 31.9582 | 2.80049 | 3.68 |
| 32.1861 | 2.78118 | 3.24 |
| 32.5778 | 2.74863 | 4.97 |
| 33.1151 | 2.70524 | 2.16 |
| 33.536 | 2.67004 | 0.87 |
| 33.7638 | 2.65254 | 0.87 |
| 33.995 | 2.63722 | 5.95 |
| 34.4002 | 2.60707 | 3.35 |
| 34.8894 | 2.57163 | 3.54 |
| 35.1308 | 2.5524 | 1.29 |
| 35.4129 | 2.53271 | 0.93 |

TABLE 8-continued

| XRPD peak list for propyl gallate Pattern 1 | | |
|---|---|---|
| Pos. [°2θ] | d-spacing [Å] | Rel. Int. [%] |
| 36.0008 | 2.49269 | 1.12 |
| 36.2293 | 2.47954 | 2.1 |
| 36.4225 | 2.46683 | 1.63 |
| 36.8257 | 2.44074 | 3.27 |
| 37.1284 | 2.42154 | 1.84 |
| 37.9861 | 2.36685 | 2.15 |
| 38.1562 | 2.35864 | 2.72 |
| 38.7937 | 2.32134 | 2.13 |
| 39.0605 | 2.30609 | 2.88 |

Further analysis of propyl gallate Pattern 1 gave the following results.

The stoichiometry was determined to be 1:~0.6 (psilocin: propyl gallate) by $^1$H-NMR spectroscopy.

The sample was analysed by TG/DTA and weight loss of ~1.13% was observed between ~40-188° C. which equated to ~0.08 mol eq. of acetone. Weight loss was observed at temperatures greater than 200° C., and was likely associated with decomposition. An endotherm was observed at onset temperature of ~155° C., which is concordant with DSC data.

DVS analysis showed that the total weight gain observed between ambient (i.e., 40% RH) and 80% RH was ~0.66% w/w. XRPD analysis was performed on the sample post DVS and showed that no change in form was observed.

The Psilocin propyl gallate cocrystal was stressed at 40° C./75% RH and 20° C./60% RH for 8 days. No change in form was observed.

HPLC solubility was estimated in FaSSIF at ~37° C. The material had solubility of ~3.39 mg/mL after 15 mins and ~2.65 mg/mL after 22 hours.

(viii) Stearic Acid

Psilocin stock solution (490 μL; 1 mol eq; acetone) and stearic acid (30.2 mg; 1.05 mol eq) were placed into a vial. The suspension was stirred at 20° C. for 2 days prior to isolation of the solids via centrifugation and decantation. XRPD analysis of the solids indicated the material was composed of a new solid form, herein designated stearic acid Pattern 1, the XRPD characteristics of which are shown in Table 9 below and in FIG. 9.

Separately, Psilocin (~60 mg, 1 mol eq) and stearic acid (88.383 mg; ~1.05 mol eq) were charged to a vial with acetone (600 μL). The sample was stirred at 20° C. The sample was seeded with stearic acid Pattern 1 and left to stir at 20° C. for a further 5 days prior to isolation by centrifugation and decantation. The bulk sample was dried under a flow of nitrogen overnight. XRPD analysis confirmed the material was composed of a new solid form, designated stearic acid Pattern 2 the XRPD characteristics of which are shown in Table 10 below and in FIG. 10.

TABLE 9

| XRPD peak list for stearic acid Pattern 1 | | |
|---|---|---|
| Pos. [°2θ] | d-spacing [Å] | Rel. Int. [%] |
| 5.4107 | 16.33357 | 20.53 |
| 8.1133 | 10.8887 | 1.9 |
| 8.2903 | 10.65663 | 2.2 |
| 10.4344 | 8.47825 | 2.84 |
| 10.6657 | 8.28801 | 0.9 |
| 10.9962 | 8.04627 | 2.94 |

TABLE 9-continued

| XRPD peak list for stearic acid Pattern 1 | | |
|---|---|---|
| Pos. [°2θ] | d-spacing [Å] | Rel. Int. [%] |
| 11.9757 | 7.39032 | 8.08 |
| 12.8967 | 6.86453 | 2.3 |
| 13.4219 | 6.59708 | 9.95 |
| 14.2883 | 6.19895 | 8.72 |
| 14.7147 | 6.02024 | 3.22 |
| 14.959 | 5.92247 | 4.65 |
| 15.2238 | 5.82004 | 8.46 |
| 15.6845 | 5.65011 | 3.33 |
| 16.0114 | 5.53548 | 18.3 |
| 16.2683 | 5.44866 | 6.63 |
| 16.8294 | 5.26823 | 14.07 |
| 17.2897 | 5.129 | 2.82 |
| 17.995 | 4.92954 | 12.12 |
| 18.2879 | 4.85125 | 15.57 |
| 18.6229 | 4.76472 | 4.42 |
| 18.8176 | 4.71587 | 19.49 |
| 19.0128 | 4.66789 | 6.47 |
| 19.5954 | 4.5304 | 11.02 |
| 19.7229 | 4.49767 | 2.6 |
| 20.0405 | 4.43078 | 7.64 |
| 20.5414 | 4.32384 | 3.89 |
| 21.4059 | 4.15114 | 100 |
| 21.5849 | 4.11711 | 50.72 |
| 21.7909 | 4.07528 | 1.88 |
| 22.0907 | 4.02397 | 3.82 |
| 22.572 | 3.93925 | 2.05 |
| 22.9203 | 3.88017 | 9.81 |
| 23.2725 | 3.82224 | 6.51 |
| 23.4972 | 3.7862 | 42.34 |
| 23.6565 | 3.76105 | 16.9 |
| 24.0404 | 3.70187 | 13.15 |
| 24.8463 | 3.58063 | 3.68 |
| 24.986 | 3.56092 | 3.93 |
| 25.1704 | 3.53818 | 9.39 |
| 25.4215 | 3.5038 | 5.78 |
| 25.7405 | 3.45822 | 1.69 |
| 26.2338 | 3.39431 | 1.25 |
| 26.5319 | 3.35684 | 1.58 |
| 26.9907 | 3.30355 | 1.53 |
| 27.6091 | 3.23095 | 2.08 |
| 28.838 | 3.096 | 2.08 |
| 30.1577 | 2.96345 | 1.51 |
| 31.6785 | 2.82457 | 1.86 |
| 32.786 | 2.73165 | 0.81 |
| 36.2658 | 2.47713 | 2.26 |
| 36.7249 | 2.44721 | 1.72 |
| 38.277 | 2.35148 | 0.9 |
| 39.6569 | 2.27278 | 1.57 |

Further analysis of stearic acid Pattern 1 gave the following results.

The stoichiometry was determined to be 1:~1.6 (psilocin: stearic acid) by $^{1}$H-NMR spectroscopy.

The XRPD foil was reanalysed after 5 days, and no change in form was observed.

TABLE 10

| XRPD peak list for stearic acid Pattern 2 | | |
|---|---|---|
| Pos. [°2θ] | d-spacing [Å] | Rel. Int. [%] |
| 4.4647 | 19.79191 | 100 |
| 8.9469 | 9.88413 | 14.4 |
| 11.6165 | 7.61166 | 1.45 |
| 11.9395 | 7.4126 | 6.01 |
| 13.4042 | 6.60027 | 4.12 |
| 13.5961 | 6.51291 | 13.97 |
| 13.8123 | 6.41146 | 9.31 |
| 14.3137 | 6.18799 | 42.93 |
| 15.6444 | 5.6645 | 15.73 |
| 16.274 | 5.44677 | 29.72 |
| 16.6574 | 5.32223 | 33.18 |

TABLE 10-continued

| XRPD peak list for stearic acid Pattern 2 | | |
|---|---|---|
| Pos. [°2θ] | d-spacing [Å] | Rel. Int. [%] |
| 17.5123 | 5.06431 | 8.99 |
| 17.9736 | 4.93537 | 12.54 |
| 18.7433 | 4.73438 | 15.01 |
| 19.1684 | 4.63033 | 9.76 |
| 19.4278 | 4.56531 | 1.97 |
| 19.7193 | 4.49848 | 6.95 |
| 19.963 | 4.44778 | 37.38 |
| 20.1253 | 4.4123 | 29.85 |
| 20.847 | 4.26115 | 29.89 |
| 21.2482 | 4.18159 | 7.92 |
| 21.6459 | 4.10565 | 5.97 |
| 22.6209 | 3.93085 | 28.73 |
| 23.2742 | 3.82197 | 39.82 |
| 23.9943 | 3.70887 | 63.63 |
| 24.4715 | 3.63762 | 8.06 |
| 25.1211 | 3.54207 | 1.88 |
| 26.4193 | 3.37368 | 28.15 |
| 27.7529 | 3.21187 | 2.19 |
| 28.433 | 3.13657 | 2.16 |
| 28.8808 | 3.09151 | 1.92 |
| 30.5103 | 2.93 | 3.46 |
| 31.6569 | 2.82645 | 1.75 |
| 32.2803 | 2.77098 | 1.82 |
| 34.0953 | 2.62968 | 1.28 |
| 35.2132 | 2.54872 | 1.48 |
| 35.8075 | 2.50777 | 1.55 |
| 38.5565 | 2.33313 | 2.31 |
| 38.9717 | 2.31114 | 5.05 |

Further analysis of stearic acid Pattern 2 gave the following results.

The stoichiometry was determined to be 1:~1 (psilocin: stearic acid) by $^{1}$H-NMR spectroscopy.

The sample was analysed by TG/DTA and no weight loss was observed. An endotherm with an onset temperature of ~87° C. was observed.

A sample of material was stressed at 40° C./75% RH for 6 days to ascertain its stability. The material was analysed by XRPD after this time. No change in physical form was observed.

SUMMARY

It has been shown that co-crystals form with psilocin and these co-formers. The co-crystals have properties that make them useful in pharmaceutical settings, such as low hygroscopicity and high solubility. In particular, the crystalline form formed with L-lactic acid has extremely high solubility and is non-hygroscopic.

| | Co-former | | |
|---|---|---|---|
| Property | Decanoic acid | L-lactic acid | Propyl gallate |
| XRPD pattern | Pattern 2 | Pattern 1 | Pattern 1 |
| Hygroscopicity | Non-hygroscopic | Non-hygroscopic | Slightly hygroscopic |
| Storage stability at 40° C./75% RH | No physical form change | No physical form change | No physical form change |
| Solubility in FasSiF (mg/ml) | 3 | >100 | 3 |

ASPECTS OF THE INVENTION

In one embodiment, the invention provides the following aspects:

1. A co-crystal comprising psilocin and a co-former, wherein the co-former is an acid.
2. A co-crystal according to aspect 1, wherein the co-former is an organic acid.
3. A co-crystal according to aspect 1 or aspect 2, wherein the co-former is a compound which comprises one or more of a carboxylic acid moiety, a sulfonic acid moiety, a squaric acid moiety, a sulphonamide moiety, a carboxylic sulfonimide moiety, and a sulfimide moiety.
4. A co-crystal according to any one of the preceding aspects, wherein the co-former is a compound which comprises a carboxylic acid moiety.
5. A co-crystal according to any one of the preceding aspects, wherein the co-former has a $pK_a$ of less than or equal to 7.0.
6. A co-crystal according to any one of the preceding aspects, wherein the co-former has a $pK_a$ of less than or equal to 6.0.
7. A co-crystal according to any one of the preceding aspects, wherein the co-former has a $pK_a$ of greater than or equal to 1.5.
8. A co-crystal according to any one of the preceding aspects, wherein the co-former as a $pK_a$ of greater than or equal to 2.5.
9. A co-crystal according to any one of the preceding aspects, wherein the molar ratio of psilocin:co-former is from 1:0.25 to 1:4.
10. A co-crystal according to aspect 9, wherein the molar ratio of psilocin:co-former is about 1:0.5.
11. A co-crystal according to aspect 9, wherein the molar ratio of psilocin:co-former is about 1:1.
12. A co-crystal according to aspect 9, wherein the molar ratio of psilocin:co-former is about 1:2.
13. A co-crystal according to any one of the preceding aspects, wherein the co-crystal is in the form of a solvate or hydrate.
14. A co-crystal according to aspect 13, wherein the solvate or hydrate is stoichiometric or non-stoichiometric.
15. A co-crystal according to any one of the preceding aspects, wherein the co-former is selected from: N-acetyl glycine, alginic acid, 2-(4-hydroxybenzoyl) benzoic acid, gluconic acid, glucoheptonic acid, 2-naphthoic acid, orotic acid, succinic acid, L-ascorbic acid, L-tartaric acid, cinnamic acid, ferulic acid, fumaric acid, gentisic acid, gallic acid, citric acid, p-coumaric acid, L-lactic acid, disodium EDTA, nicotinic acid, 1-hydroxy-2-naphthoic acid, 2-ketoglutaric acid, 4-hydroxyphenyl acetic acid, L-malic acid, maleic acid, oxalic acid and saccharin.
16. A co-crystal according to aspect 15, wherein the co-former is selected from: citric acid, fumaric acid, succinic acid, gluconic acid, L-tartaric acid, L-ascorbic acid, L-lactic acid, saccharin, and nicotinic acid.
17. A pharmaceutical composition comprising:
    (a) a co-crystal as defined in any one of the preceding aspects; and
    (b) a pharmaceutically acceptable excipient or diluent.
18. A process for producing a co-crystal as defined in any one of aspects 1 to 16, the process comprising combining psilocin and a co-former which is an acid.
19. A method of treating or preventing a disease or condition selected from psychological, neurological and central nervous system disorders in a patient, the method comprising administering a therapeutically effective amount of a co-crystal as defined in any one of aspects 1 to 16 to the patient.
20. The method of aspect 19, wherein the disease or condition is selected from depression, anxiety, death anxiety, demoralization, adjustment disorders, hopelessness, suicidal ideation and desire for hastened death.
21. The method of aspect 19, wherein the disease or condition is selected from cocaine-related disorders, opioid-related disorders and stimulant-related disorders.
22. A co-crystal as defined in any one of aspects 1 to 16 for use in the treatment or prevention of a disease or condition as defined in any one of aspects 19 to 21.
23. Use of a co-crystal as defined in any one of aspects 1 to 16 in the manufacture of a medicament for the treatment or prevention of a disease or condition as defined in any one of aspects 19 to 21.
24. A kit comprising:
    a co-crystal as defined in any one of aspects 1 to 16 or a pharmaceutical composition as defined in aspect 17; and
    instructions for use of the co-crystal or pharmaceutical composition in a method of treating or preventing a disease or condition as defined in any one of aspects 19 to 21.

In a second embodiment, the invention provides the following aspects:

1. A co-crystal comprising psilocin and a co-former, wherein the co-former is a base.
2. A co-crystal according to aspect 1, wherein the co-former is an organic base.
3. A co-crystal according to aspect 1 or aspect 2, wherein the co-former is a compound which comprises one or more of an amine moiety, a pyridine moiety, a piperazine moiety, an amide moiety, a xanthine moiety and a morpholine moiety.
4. A co-crystal according to any one of the preceding aspects, wherein the co-former is a compound which comprises an amine moiety.
5. A co-crystal according to any one of the preceding aspects, wherein the co-former has a $pK_b$ of less than or equal to 11.0.
6. A co-crystal according to any one of the preceding aspects, wherein the co-former has a $pK_b$ of less than or equal to 9.0.
7. A co-crystal according to any one of the preceding aspects, wherein the co-former has a $pK_b$ of greater than or equal to 3.5.
8. A co-crystal according to any one of the preceding aspects, wherein the co-former as a $pK_b$ of greater than or equal to 4.5.
9. A co-crystal according to any one of the preceding aspects, wherein the molar ratio of psilocin:co-former is from 1:0.25 to 1:4.
10. A co-crystal according to aspect 9, wherein the molar ratio of psilocin:co-former is about 1:0.5.
11. A co-crystal according to aspect 9, wherein the molar ratio of psilocin:co-former is about 1:1.
12. A co-crystal according to aspect 9, wherein the molar ratio of psilocin:co-former is about 1:2.

13. A co-crystal according to any one of the preceding aspects, wherein the co-crystal is in the form of a solvate or hydrate.
14. A co-crystal according to aspect 13, wherein the solvate or hydrate is stoichiometric or non-stoichiometric.
15. A co-crystal according to any one of the preceding aspects, wherein the co-former is selected from: 4,4-bipyridine, pyridoxine, deanol, 4-(2-hydroxyethyl)-morpholine, piperazine, theophylline, nicotinamide, isonicotinamide, tromethamine, tert-butyl amine and diethylamine.
16. A co-crystal according to aspect 15, wherein the co-former is selected from: theophylline, nicotinamide, isonicotinamide, and tromethamine.
17. A pharmaceutical composition comprising:
(a) a co-crystal as defined in any one of the preceding aspects; and
(b) a pharmaceutically acceptable excipient or diluent.
18. A process for producing a co-crystal as defined in any one of aspects 1 to 16, the process comprising combining psilocin and a co-former which is a base.
19. A method of treating or preventing a disease or condition selected from psychological, neurological and central nervous system disorders in a patient, the method comprising administering a therapeutically effective amount of a co-crystal as defined in any one of aspects 1 to 16 to the patient.
20. The method of aspect 19, wherein the disease or condition is selected from depression, anxiety, death anxiety, demoralization, hopelessness, suicidal ideation and desire for hastened death.
21. The method of aspect 19, wherein the disease or condition is selected from cocaine-related disorders, opioid-related disorders and stimulant-related disorders.
22. A co-crystal as defined in any one of aspects 1 to 16 for use in the treatment or prevention of a disease or condition as defined in any one of aspects 19 to 21.
23. Use of a co-crystal as defined in any one of aspects 1 to 16 in the manufacture of a medicament for the treatment or prevention of a disease or condition as defined in any one of aspects 19 to 21.
24. A kit comprising:
a co-crystal as defined in any one of aspects 1 to 16 or a pharmaceutical composition as defined in aspect 17; and
instructions for use of the co-crystal or pharmaceutical composition in a method of treating or preventing a disease or condition as defined in any one of aspects 19 to 21.

In a third embodiment, the invention provides the following aspects:

1. A co-crystal comprising psilocin and a co-former, wherein the co-former is a neutral compound, which neutral compound is:
(i) a compound which is amphoteric;
(ii) a compound which is zwitterionic;
(iii) a compound which comprises neither an acidic moiety nor a basic moiety; or
(iv) a compound which is an inorganic salt.
2. A co-crystal according to aspect 1, wherein the co-former is a compound which is amphoteric.
3. A co-crystal according to aspect 2, wherein the co-former is an amino acid or amino acid derivative.
4. A co-crystal according to aspect 3, wherein the co-former is selected from: L-lysine, L-histidine, L-tyrosine, L-pyroglutamic acid, DL-cysteine, and L-glutamic acid.
5. A co-crystal according to aspect 4, wherein the co-former is selected from: L-pyroglutamic acid, DL-cysteine, and L-glutamic acid.
6. A co-crystal according to aspect 1, wherein the co-former is a compound which comprises neither an acidic moiety nor a basic moiety.
7. A co-crystal according to aspect 6, wherein the co-former is a compound which comprises an ester moiety.
8. A co-crystal according to aspect 6, wherein the co-former is a compound which comprises an ether moiety.
9. A co-crystal according to aspect 6, wherein the co-former is a compound which comprises an alcohol moiety.
10. A co-crystal according to aspect 6, wherein the co-former is selected from: ethyl maltol, meso-erythritol, D-mannitol, D-sorbitol, D-xylitol, inosine, and L-ascorbic acid 6-hexadecanoate.
11. A co-crystal according to aspect 6, wherein the co-former is a compound which comprises a phenol moiety.
12. A co-crystal according to aspect 11, wherein the co-former is selected from: 2,6-di-tert-butyl-4-methylphenol, 2-tert-butyl-4-methoxyphenol, vanillin, ethyl vanillin, $C_{1-4}$ parabens, propyl gallate.
13. A co-crystal according to aspect 12, wherein the co-former is selected from: propyl gallate, 2,6-di-tert-butyl-4-methylphenol, and 2-tert-butyl-4-methoxyphenol.
14. A co-crystal according to aspect 6, where the co-former is a compound which comprises a carboxamide moiety.
15. A co-crystal according to aspect 14, wherein the co-former is urea.
16. A co-crystal according to aspect 1, wherein the co-former is an inorganic salt.
17. A co-crystal according to aspect 16, wherein the co-former is selected from: sodium dihydrogen phosphate, sodium bisulfite, acesulfame potassium and sodium formaldehyde sulfoxylate.
18. A co-crystal according to aspect 17, wherein the co-former is selected from: sodium bisulfite, acesulfame potassium, and sodium formaldehyde sulfoxylate.
19. A co-crystal according to any one of the preceding aspects, wherein the molar ratio of psilocin:co-former is from 1:0.25 to 1:4.
20. A co-crystal according to aspect 19, wherein the molar ratio of psilocin:co-former is about 1:0.5.
21. A co-crystal according to aspect 19, wherein the molar ratio of psilocin:co-former is about 1:1.
22. A co-crystal according to aspect 19, wherein the molar ratio of psilocin:co-former is about 1:2.
23. A co-crystal according to any one of the preceding aspects, wherein the co-crystal is in the form of a solvate or hydrate.
24. A co-crystal according to aspect 23, wherein the solvate or hydrate is stoichiometric or non-stoichiometric.
25. A pharmaceutical composition comprising:
(a) a co-crystal as defined in any one of the preceding aspects; and
(b) a pharmaceutically acceptable excipient or diluent.

26. A process for producing a co-crystal as defined in any one of aspects 1 to 22, the process comprising combining psilocin and a co-former which is as defined in aspect 1.
27. A method of treating or preventing a disease or condition selected from psychological, neurological and central nervous system disorders in a patient, the method comprising administering a therapeutically effective amount of a co-crystal as defined in any one of aspects 1 to 24 to the patient.
28. The method of aspect 27, wherein the disease or condition is selected from depression, anxiety, death anxiety, demoralization, hopelessness, suicidal ideation and desire for hastened death.
29. The method of aspect 27, wherein the disease or condition is selected from cocaine-related disorders, opioid-related disorders and stimulant-related disorders.
30. A co-crystal as defined in any one of aspects 1 to 24 for use in the treatment or prevention of a disease or condition as defined in any one of aspects 27 to 29.
31. Use of a co-crystal as defined in any one of aspects 1 to 24 in the manufacture of a medicament for the treatment or prevention of a disease or condition as defined in any one of aspects 27 to 29.
32. A kit comprising:
 a co-crystal as defined in any one of aspects 1 to 24 or a pharmaceutical composition as defined in aspect 25; and
 instructions for use of the co-crystal or pharmaceutical composition in a method of treating or preventing a disease or condition as defined in any one of aspects 27 to 29.

The invention claimed is:

1. A co-crystal or salt consisting essentially of psilocin and a co-former, wherein the co-former is L-lactic acid, wherein the molar ratio of psilocin:L-lactic acid is about 1:1, and wherein the co-crystal or salt has an x-ray powder diffraction pattern comprising peaks at 13.4°, 16.8° and 19.5°±0.2° 2θ.

2. The co-crystal or salt according to claim 1, wherein the x-ray powder diffraction pattern further comprises peaks at 16.7°, 23.0° and 24.3°±0.2° 2θ.

3. The co-crystal or salt according to claim 1, wherein the x-ray powder diffraction pattern comprises seven or more peaks selected from 13.4°, 14.9°, 16.7°, 16.8°, 19.5°, 20.6°, 23.0°, 24.3° and 26.3°±0.2° 2θ.

4. The co-crystal or salt according to claim 1, wherein the x-ray powder diffraction pattern comprises the following peaks:

| Angle [°2θ] | Rel. Int. [%] |
|---|---|
| 11.0 | 30 |
| 13.4 | 96 |
| 14.2 | 14 |
| 14.9 | 47 |
| 16.7 | 55 |
| 16.8 | 89 |
| 19.5 | 100 |
| 20.1 | 10 |
| 20.3 | 22 |
| 20.6 | 38 |
| 22.2 | 17 |
| 22.5 | 11 |
| 22.8 | 18 |
| 23.0 | 52 |
| 24.3 | 77 |
| 24.4 | 33 |
| 26.3 | 39 |
| 29.1 | 16 |
| 34.0 | 10 |

5. A kit comprising:
 a co-crystal or salt as defined in claim 1; and
 instructions for use of the co-crystal or salt in a method of treating a disease or condition selected from depression, anxiety and demoralization in a patient, the method comprising administering a therapeutically effective amount of the co-crystal or salt to the patient.

6. A method of treating a disease or condition selected from depression, anxiety and demoralization in a patient, the method comprising administering a therapeutically effective amount of the co-crystal or salt as defined in claim 1 to the patient.

* * * * *